United States Patent
Bohlmann et al.

(10) Patent No.: US 6,780,855 B2
(45) Date of Patent: *Aug. 24, 2004

(54) 11β-HALOGEN-7α-SUBSTITUTED ESTRATRIENES, PROCESS FOR THE PRODUCTION OF PHARMACEUTICAL PREPARATIONS THAT CONTAIN THESE 11β-HALOGEN-7α-SUBSTITUTED ESTRATRIENES AS WELL AS THEIR USE FOR THE PRODUCTION OF PHARMACEUTICAL AGENTS

(75) Inventors: Rolf Bohlmann, Berlin (DE); Nikolaus Heinrich, Berlin (DE); Helmut Hofmeister, Berlin (DE); Jorg Kroll, Berlin (DE); Hermann Kunzer, Berlin (DE); Gerhard Sauer, Berlin (DE); Ludwig Zorn, Berlin (DE); Karl-Heinrich Fritzemeier, Berlin (DE); Monika Lessl, Berlin (DE); Rosemarie Lichtner, Berlin (DE); Yukishige Nishino, Berlin (DE); Karsten Parczyk, Berlin (DE); Martin Schneider, Berlin (DE)

(73) Assignee: Schering Aktiengesellschaft, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/380,413
(22) PCT Filed: Dec. 23, 1998
(86) PCT No.: PCT/EP98/08470
§ 371 (c)(1),
(2), (4) Date: Dec. 2, 1999
(87) PCT Pub. No.: WO99/33855
PCT Pub. Date: Jul. 8, 1999

(65) Prior Publication Data
US 2003/0069434 A1 Apr. 10, 2003

(30) Foreign Application Priority Data
Dec. 23, 1997 (DE) ............... 197 58 390
Feb. 10, 1998 (DE) ............... 198 06 357

(51) Int. Cl.$^7$ ............... C07J 1/00; C07J 43/00; C07J 17/00
(52) U.S. Cl. ............... 514/182; 514/170; 514/176; 514/172; 514/267; 540/47; 540/113; 540/107; 540/114; 540/117; 540/120; 552/626
(58) Field of Search ............... 552/626; 514/169, 514/182, 179, 181; 540/107, 113, 114, 117, 120

(56) References Cited

U.S. PATENT DOCUMENTS

| 5,866,560 A | * | 2/1999 | Bohlmann et al. | 514/182 |
| 5,986,115 A | * | 11/1999 | Bohlmann et al. | 549/416 |
| 6,271,403 B1 | * | 8/2001 | Bohlmann | 552/626 |

* cited by examiner

Primary Examiner—Sabiha Qazi
(74) Attorney, Agent, or Firm—Millen, White, Zelano, Branigan, P.C.

(57) ABSTRACT

This invention describes the new 11β-halogen-7α-substituted estratrienes of general formula I

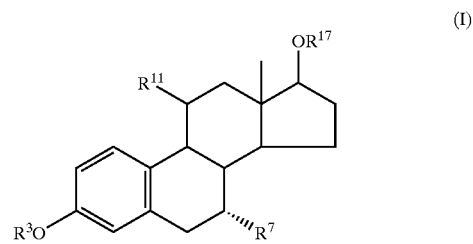

in which $R^{11}$ is a fluorine or chlorine atom, and the other substituents have the meanings that are explained in more detail in the description.

The compounds have antiestrogenic properties or tissue-selective estrogenic properties and are suitable for the production of pharmaceutical agents.

27 Claims, No Drawings

11β-HALOGEN-7α-SUBSTITUTED ESTRATRIENES, PROCESS FOR THE PRODUCTION OF PHARMACEUTICAL PREPARATIONS THAT CONTAIN THESE 11β-HALOGEN-7α-SUBSTITUTED ESTRATRIENES AS WELL AS THEIR USE FOR THE PRODUCTION OF PHARMACEUTICAL AGENTS

This application is a 371 of PCT/EP98/0848 filed on Dec. 23, 1998.

This invention relates to 11β-halogen-7α-substituted estratrienes of general formula I

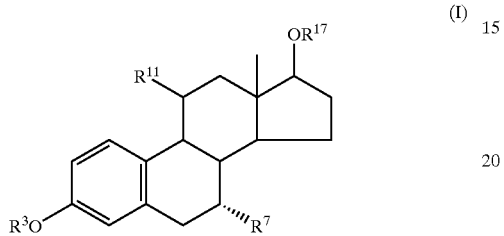

(I)

in which
$R^3$ means a hydrogen atom, a hydrocarbon radical with up to 8 carbon atoms or a radical of partial formula $R^{3'}$—C (O)—, in which $R^{3'}$ means a hydrogen atom or a hydrocarbon radical with up to 8 carbon atoms or a phenyl radical, $R^7$ means a radical of formula —A—B—Z—$R^{20}$,
in which
A stands for a direct bond or a benzylidene radical, whereby the methylene group is bonded to the 7-carbon atom of the steroid, or a phenylene radical,
B stands for a straight-chain or branched-chain alkylene, alkenylene or alkinylene group with 3 to 14 carbon atoms, and
Z stands for —$NR^{21}$— and $R^{21}$ stands for a $C_1$–$C_3$ alkyl group,
whereby then $R^{20}$ means
a hydrogen atom,
a straight-chain or branched-chain alkyl, alkenyl or alkinyl group with up to 10 carbon atoms or one of groupings
—D—$C_nF_{2n+1}$, whereby D is a straight-chain or branched-chain alkylene, alkenylene or alkinylene group with up to 8 carbon atoms and n is an integer from 1 to 8,
—L—CH=CF—$C_pF_{2p+1}$, whereby L is a straight-chain or branched-chain alkylene, alkenylene or alkinylene group with 2 to 7 carbon atoms and p is an integer from 2 to 7,
—D—O—$(CH_2)_q$-aryl, whereby D has the already indicated meaning, q is 0, 1, 2 or 3, and aryl stands for a phenyl radical, 1- or 2-naphthyl radical or a heteroaryl radical that is optionally substituted in one or two places,
—D—O—$(CH_2)_r$—$C_nF_{2n+1}$, whereby D and n have the already indicated meanings and r stands for an integer from 1 to 5, or
$R^{20}$ and $R^{21}$ with the nitrogen atom to which they are bonded form a saturated or unsaturated heterocycle with 5 or 6 chain links, which optionally contains one or two additional heteroatoms, selected from nitrogen, oxygen and sulfur, and optionally is substituted, or Z stands for —$SO_x$ and x stands for 0, 1 or 2,
whereby $R^{20}$ then means
a straight-chain or branched-chain alkyl, alkenyl or alkinyl group with up to 10 carbon atoms, or one of groupings
—D—C $F_{2n+1}$, whereby D is a straight-chain or branched-chain alkylene, alkenylene or alkinylene group with up to 8 carbon atoms and n is an integer from 1 to 8,
—L—CH=CF—$C_pF_{2p+1}$, whereby L is a straight-chain or branched-chain alkylene, alkenylene or alkinylene group with 2 to 7 carbon atoms and p is an integer from 2 to 7,
—D—O—$(CH_2)_q$-aryl, whereby D has the already indicated meaning, q is 0, 1, 2 or 3, and aryl stands for a phenyl radical, 1- or 2-naphthyl radical or a heteroaryl radical that is optionally substituted in one or two places,
—D—O—$(CH_2)_r$—$C_nF_{2n+1}$, whereby D and n have the already indicated meanings and r stands for an integer from 1 to 5, or Z stands for —$NR^{31}$,
whereby then $R^{20}$ is a straight-chain or branched-chain, optionally partially fluorinated alkyl, alkenyl or alkinyl radical with up to 14 carbon atoms, which can be interrupted by one to three heteroatoms —O— and —S— and groupings —$NR^{32}$—, in which $R^{32}$ is a hydrogen atom or a $C_1$–$C_3$ alkyl radical, an aryl or heteroaryl radical that is optionally substituted in one or two places, a $C_3$–$C_{10}$ cycloalkyl radical that is optionally substituted in one or two places, a $C_4$–$C_{15}$ cycloalkylalkyl radical that is optionally substituted in one or two places, a $C_7$–$C_{20}$ aralkyl radical that is optionally substituted in one or two places, a heteroaryl-$C_1$–$C_6$ alkyl radical that is optionally substituted in one or two places or an optionally substituted aminoalkyl radical, and $R^{31}$ is a radical of formula —C(O)$R^{33}$ or —$CH_2$—$R^{33}$, whereby then $R^{33}$ is a straight-chain or branched-chain, optionally partially fluorinated alkyl, alkenyl or alkinyl radical with up to 14 carbon atoms, which can be interrupted by one to three heteroatoms —O— and —S— and groupings —$NR^{32}$—, in which $R^{32}$ is a hydrogen atom or a $C_1$–$C_3$ alkyl radical, an aryl or heteroaryl radical that is optionally substituted in one or two places, a $C_3$–$C_{10}$ cycloalkyl radical that is optionally substituted in one or two places, a $C_4$–$C_{15}$ cycloalkylalkyl radical that is optionally substituted in one or two places, a $C_7$–$C_{20}$ aralkyl radical that is optionally substituted in one or two places, a heteroaryl-$C_1$–$C_6$ alkyl radical that is optionally substituted in one or two places, an optionally substituted aminoalkyl radical or a biphenylene radical,
whereby side chain $R^7$ cannot have the meanings that are indicated there in PCT/EP97/04517 for SK, $R^{11}$ means a fluorine or chlorine atom,
$R^{17}$ means a hydrogen atom or a radical of partial formula $R^{17'}$—C(O)—, in which $R^{17'}$ is a hydrogen atom or a hydrocarbon radical with up to 8 carbon atoms.

$R^7$ can have the meanings that are described in EP 138 504 B1 for the 7α-side chain of the steroid, with the restriction of the above-indicated disclaimer.

As $R^3$, the 7α-substituted estratrienes according to the invention preferably have a hydrogen atom. The hydroxy group, however, can also be etherified with a straight-chain or branched-chain, saturated or unsaturated hydrocarbon radical with up to 8 carbon atoms, such as, e.g., a methyl, ethyl, propyl, isopropyl, butyl, isobutyl, tert-butyl, pentyl, isopentyl, neopentyl, heptyl, hexyl or octyl radical or esterified with an acyl radical $R^{3'}$—C(O)—, in which $R^{3'}$ is a hydrogen atom or a hydrocarbon radical with up to 8 carbon atoms or a phenyl radical.

A fluorine atom is preferred for substituents $R^{11}$.

A hydrogen atom or a radical of partial formula $R^{17'}$—C(O)— can stand for substituents $R^{17}$, in which $R^{17'}$ is a hydrogen atom or a hydrocarbon radical with up to 8 carbon atoms. A hydrogen atom is preferred for $R^{17}$. The hydrocarbon radical can have the meaning of, for example, a methyl, ethyl, propyl, isopropyl, butyl, isobutyl, tert-butyl, pentyl, isopentyl, neopentyl, heptyl, hexyl or octyl radical.

In the compounds of general formula I according to the invention, A stands for a direct bond, a phenylene or benzylidene radical, whereby in the last case, the methylene group is bonded to carbon atom 7 of the steroid skeleton.

An aryl radical within the terms of this invention is preferably a phenyl radical, 1- or 2-naphthyl radical; the phenyl radical is preferred. Unless expressly indicated otherwise, aryl also always includes a heteroaryl radical. Examples of a heteroaryl radical are the 2-, 3- or 4-pyridinyl radical, the 2-or 3-furyl radical, the 2- or 3-thienyl radical, the 2- or 3-pyrrolyl radical, the 2-, 4- or 5-imidazolyl radical, the pyrazinyl radical, the 2-, 4- or 5-pyrimidinyl radical or 3- or 4-pyridazinyl radical.

In the ring, aralkyl groups in R20 and $R^{31}$ can contain up to 14 C atoms, preferably 6 to 10 C atoms, and in the alkyl chain, they can contain 1 to 8, preferably 1 to 4 C atoms. As aralkyl radicals, for example, benzyl, phenylethyl, phenylpropyl, naphthylmethyl, and naphthylethyl are suitable.

As heteroalkylalkyl radicals, for example, furylmethyl, thienylethyl, and pyridylpropyl can be mentioned.

The aralkyl or heteroarylalkyl radical can be substituted.

If $R^{20}$ and $R^{21}$ with the nitrogen atom, to which they are bonded, a saturated or unsaturated heterocycle with 5 or 6 chain links, which optionally contains one or two additional heteroatoms that are selected from nitrogen, oxygen and sulfur, this is especially a pyrrolidine, piperidine, morpholine or piperazine ring.

As substituents for the aryl, heteroaryl, aralkyl and heteroarylalkyl radicals, for example, a trifluoromethyl-, pentafluoroethyl-, trifluoromethylthio-, methoxy-, ethoxy-, nitro-, cyano-, halogen- (fluorine, chlorine, bromine, iodine), hydroxy-, amino-, mono($C_{1-8}$ alkyl)- or di($C_{1-8}$ alkyl)amino, whereby both alkyl groups are identical or different, di(aralkyl)amino, whereby both aralkyl groups are identical or different (for aralkyl, see above at $R^{20}$ and $R^{31}$) or the 1-methoxyacetylamino radical can be mentioned.

The sulfur atom in the side chain can be present as a single sulfur bridge (sulfide), as sulfone or sulfoxide.

According to this invention, for example, the following radicals can stand for side chain $R^7$ (A means a direct bond):
a radical of formula —$(CH_2)_s$—Z—$R^{20}$,
  whereby
  s is an integer from 3 to 8,
  Z stands for —$NR^{21}$ and $R^{21}$ stands for a $C_1$-$C_3$ alkyl group,
  in which $R^{20}$ means
    a hydrogen atom,
    a $C_1$-$C_9$ alkyl group, or
    one of the groupings
      —$(CH_2)_m$—$C_nF_{2n+1}$, whereby m and n, independently of one another, in each case is an integer from 1 to 8,
      —$(CH_2)_o$—CH=CF—$C_pF_{2p+1}$, whereby o is 1, 2 or 3 and p is an integer from 2 to 7,
      —$(CH_2)_m$—O—$(CH_2)_q$-aryl, whereby m has the already indicated meaning, q is 0, 1, 2 or 3 and aryl stands for a phenyl or heteroaryl radical that is optionally substituted in one or two places,
      —$(CH_2)_m$—O—$(CH_2)_r$—$C_nF_{2n+1}$, whereby m and n have the already indicated meanings and r stands for an integer from 1 to 5;
a radical of formula —$(CH_2)_s$—Z—$R^{20}$,
  whereby
  s is an integer from 3 to 8,
  Z stands for —$NR^{21}$ and $R^{21}$ stands for a $C_1$-$C_3$ alkyl group,
  in which $R^{20}$ and $R^{21}$
  with the nitrogen atom, to which they are bonded, form a saturated or unsaturated heterocycle with 5 or 6 chain links, which optionally contains one or two additional heteroatoms, selected from nitrogen, oxygen and sulfur, and optionally is substituted;
a radical of formula —$(CH_2)_s$—Z—$R^{20}$,
  whereby
  s is an integer from 3 to 8,
  Z stands for —$SO_x$— and x stands for 0, 1 or 2,
    whereby $R^{20}$ means
      —$(CH_2)_m$—O—$(CH_2)_r$—$C_nF_{2n+1}$, whereby m and n have the already indicated meanings and r stands for an integer from 1 to 5.

As specific side chains,
—$(CH_2)_5N(CH_3)(CH_2)_3C_2F_5$
—$(CH_2)_5N(CH_3)(CH_2)_6C_2F_5$
—$(CH_2)_5N(CH_3)(CH_2)_7C_2F_5$
—$(CH_2)_5N(CH_3)(CH_2)_8C_2F_5$
—$(CH_2)_6N(CH_3)(CH_2)_6C_2F_5$
—$(CH_2)_6N(CH_3)(CH_2)_7C_2F_5$
—$(CH_2)_6N(CH_3)(CH_2)_8C_2F_5$
—$(CH_2)_5N(CH_3)(CH_2)_2C_4F_9$
—$(CH_2)_5N(CH_3)(CH_2)_3C_6F_{13}$
—$(CH_2)_5N(CH_3)(CH_2)_3C_8F_{17}$
—$(CH_2)_5N(CH_3)(CH_2)_6C_4F_9$
—$(CH_2)_5N(CH_3)(CH_2)_6C_6F_{13}$
—$(CH_2)_5N(CH_3)(CH_2)_6C_8F_{17}$
—$(CH_2)_5N(CH_3)H$
—$(CH_2)_5N(CH_3)(CH_2)_9H$
—$(CH_2)_5N(CH_3)CH_2CH=CF—C_2F_5$
—$(CH_2)_5N(CH_3)CH_2CH=CF—C_3F_{17}$
—$(CH_2)_5N(CH_3)CH_2CH=CF—C_5F_{11}$
—$(CH_2)_5N(CH3)CH_2CH=CF—C_7F_{15}$
—$(CH_2)_5$-1-Pyrrolidinyl
—$(CH_2)_5N(CH_3)(CH_2)_3$OPhenyl
—$(CH_2)_5N(CH_3)(CH_2)_3$OBenzyl
—$(CH_2)_5N(CH_3)(CH_2)_3O(CH_2)_3C_2F_5$
—$(CH_2)_9S(CH_2)_3C_2F_5$
—$(CH_2)_9SO(CH_2)_3C_2F_5$
—$(CH_2)_9SO_2(CH_2)_3C_2F_5$
can be mentioned.

Specific compounds of general formula I are described in the examples.

In addition to these compounds of general formula 1, if a nitrogen atom is contained in $R^7$, this invention also relates to their physiologically compatible addition salts with organic and inorganic acids, pharmaceutical preparations that contain these compounds of general formula I inclusive of the addition salts as well as their use for the production of pharmaceutical agents.

Inorganic and organic acids, as are known to one skilled in the art for the formation of physiologically compatible salts, are suitable for the formation of acid addition salts. As addition salts with acids, especially hydrochlorides, hydrobromides, acetates, citrates, oxalates, tartrates and methanesulfonates can be cited.

The compounds of general formula I represent compounds with strong antiestrogenic action.

The compounds according to the invention are either pure antiestrogens or so-called partial antagonists, i.e., antiestrogens with partial estrogenic action such as tamoxifen or raloxifen. In contrast to the tamoxifen, their agonistic, estrogenic action is expressed in a tissue-selective manner in the case of partial antagonists of general formula I. In particular, the agonistic action occurs in bone, in the cardiovascular system and in the central nervous system. In particular, no action or only slightly agonistic action occurs in the uterus.

Compounds with antiestrogenic properties, i.e., substances with inhibiting actions compared to estrogens have already been described extensively.

As the compounds that come closest structurally to these compounds of general formula I, the steroid derivatives that are known from EP 0 138 504 B1 can be considered. The 7α-[9-(4,4,5,5,5-pentafluoropentylsulfinyl)-n-nonyl]-estra-1,3,5(10)-triene-3,17β-diol (EP-A 0 138 504, page 58, penultimate compound) is currently under clinical development for hormone-dependent tumors (breast cancer) and represents the compound that is best known at this time, i.e., the one with the strongest antiestrogenic activity, of these steroid derivatives.

Pharmaceutical compositions, which contain sex steroid inhibitors, which have a steroidal skeleton that has a 7α-side chain in the case of the simultaneous presence of at least one other substituent in 14-, 15- or 16-position, are the subject of EP-A 0 376 576.

A considerable number of the most widely varied compounds—i.a. those of steroidal origin and those with a 2-phenylindole skeleton—which act as antiestrogens and/or suppress the estrogen biosynthesis, are disclosed in WO 93/10741.

Other steroidal antiestrogens, which carry an 11β-phenyl radical, are described in EP-AS 0 384 842 and 0 629 635.

Compounds according to the invention are antiestrogens with mostly stronger antiestrogenic action than the already mentioned 7α-[9-(4,4,5,5,5-pentafluoropentylsulfinyl)-n-nonyl]-estra-1,3,5(10)-triene-3,17β-diol and/or compounds that are distinguished from 7α-[9-(4,4,5,5,5-pentafluoropentylsulfinyl)-n-nonyl]-estra-1,3,5(10)-triene-3,17β-diol by their partial estrogenic action.

The compounds of general formula I according to this application are distinguished by the additional 11β-fluorine atom in comparison to the already known steroid derivatives according to EP-A 0 138 504 and EP-A 0 367 576.

This structural modification is of decisive importance for the advantageous properties of the compounds according to the invention.

The antiestrogenic action of the compounds according to the invention was determined in transactivation assays [Demirpence, E.; Duchesne, M.-J.; Badia, E.; Gagne, D. and Pons, M.: MVLN Cells: a Bioluminescent MCF-7-Derived cell Line to Study the Modulation of Estrogenic Activity; J. Steroid. Molec. Biol. Vol. 46, No. 3, 355–364 (1993) and Berry, M.; Metzger, D.; Chambon, P.: Role of the Two Activating Domains of the Estrogen Receptor in the Cell-type and Promoter-context Dependent Agonistic Activity of the Anti-estrogen 4-Hydroxytamoxifen; The EMBO Journal Vol. 9, 2811–2818 (1990)].

The MVLN cells are transfixed in a stable manner with reporter gene Vit-TK-LUC. The antiestrogenic active strength was determined in the presence of 0.1 nM of estradiol.

The $IC_{50}$ values for the new compounds are in the nanomolar range. In the MVLN cell line, the following $IC_{50}$ values are produced for the compound of Examples 3 and 8 (execution of test according to the above-indicated bibliographic references):

| Compound | IC50 [nM] MVLN | IC50 [nM] HeLa |
|---|---|---|
| Example 3 | 6.3 | 0.2 |
| Example 8 | 37 | 8 |

The uterus growth test in infantile rats, p.o. (test on antiestrogenic action in vivo) also confirms the antiestrogenic action of the compounds according to the invention. The test was performed as described below:

Uterus Growth Test in Infantile Rats
(Antiestrogenic Action)

Principle of the Method

In rodents, the uterus reacts to the application of estrogens with an increase in weight (both proliferation and water retention). This growth can be inhibited in a dose-dependent manner by simultaneous administration of compounds that have an antiestrogenic action.

Execution of the Test

Animals:

Infantile female rats weighing 35–45 g at the beginning of the test, 5–6 animals per dose.

Formulation and Administration of the Substances:

For the p.o. administration, the substances are dissolved in 1 part ethanol (E) and made up with 9 parts peanut oil (EÖ).

Test Batch

The young rats just dropped by the mothers are delivered for acclimation one day before the beginning of treatment and immediately supplied with food—right in the cage. The treatment is then carried out once daily over 3 days in combination with 0.5 µg of estradiol benzoate (EB). EB is always administered subcutaneously (s.c.), while the test substance is administered p.o. (perorally). 24 hours after the last administration, the animals are weighed, killed and the uteri are removed. The moist weight (less contents) is determined from the prepared uteri.

Controls

Negative control: Vehicle (E/EÖ), 0.2 ml/animal/day
Positive control: 0.5 µg of EB/0.1 ml/animal/day Evaluation The average values are determined with standard deviation (X+SD) and the significance of the differences in the control group (EB) in the Dunnett Test (p<0.05) for each group from the relative organ weights (mg/100 g of body weight). The calculation of the inhibition (in %) compared to the EB-control is carried out with a program. The relative actions of the test substances are determined by co-variance analysis and regression analysis.

Antiuterotrophic Action on Rats

| Compound from Example | Antiuterotrophic action at 0.3 mg [% inhibition] |
| --- | --- |
| 3 | 68 |
| 8 | 0 |

As pure antiestrogens for the purposes of this invention, those compounds of general formula I that show no action or, in the best case, only slightly agonistic action, i.e., an agonistic action up to about 20% of the action of estradiol, in the in-vitro test on estrogenic action that is described below can be considered.

Partial Estrogenic Action

The transition between the pure antiestrogens and the partial agonists, the tissue-selective estrogens, is seamless. Compounds that have a slightly agonistic action can also be used in the indications that are mentioned below for pure antiestrogens.

The partial estrogenic action of compounds according to the invention was determined by transactivation assays. HeLa cells were transfixed with human estrogen receptor expression vector (HEGO) and a reporter gene rPR-TK-CAT. This reporter gene contains the "Estrogen Responsive Element" of the rabbit progesterone receptor gene (+698/+729 region) before a TK-CAT gene (Savouret, J. F.; Bailly, A.; Misrahi, M.; Rauch, C.; Redeuilh, G.; Chauchereau, A.; Milgrom, E., Characterization of the Hormone Responsive Element Involved in the Regulation of the Progesterone Receptor Gene. EMBO J. 10, 1875–1883 (1991).

The estrogenic action was determined at a concentration of 1 μm.

Partial Estrogenic Action

| Compound from Example | Activation of the rPR-TK Promoter [% estradiol]* |
| --- | --- |
| 3 | −25 |
| 8 | 48 |
| 18 | 29 |
| 12 | 34 |
| 22 | 53 |

*A negative value means suppression of reporter gene activity below the value of the controls The compounds according to the invention, especially if they are pure antiestrogens, are suitable for treatment of estrogen-dependent diseases, for example breast cancer (second-line treatement of tamoxifen-resistant breast cancer; for adjuvant treatment of breast cancer instead of tamoxifen), endometrial cancer, prostate cancer, prostatic hyperplasia, anovulatory infertility and elanoma.

In addition, the pure antiestrogens of general formula I can be used as components in the products that are described in EP 346 014 B1 which contain an estrogen and a pure antiestrogen, specifically for simultaneous, sequential or separate use for selective estrogen therapy of peri- or post-menopausal women. The compounds of general formula I, especially if these are pure antiestrogens, can be used together with antigestagens (competitive progesterone antagonists) for the treatment of hormone-dependent tumors (EP 310 542 A).

Other indications in which the compounds of the general formula can be used are male hair loss, diffuse alopecia, alopecia that is caused by chemotherapy as well as hirsutism (Hye-Sun Oh and Robert C. Smart, Proc. Natl. Acad. Sci. USA, 93 (1996) 12525–12530).

In addition, the compounds of general formula I can be used for the production of medications for treating endometriosis and endometrial carcinomas.

The compounds of general formula I can also be used for the production of pharmaceutical compositions for male and female birth control (male birth control: DE-A 195 10 862.0).

The compounds of general formula I with tissue-selective partial estrogenic action can be used primarily for prophylaxis and treatment of osteoporosis and for the production of preparations for substitution therapy in pre-, peri- and post-menopause (HRT=hormone replacement therapy) (Black, L. J.; Sato, M.; Rowley, E. R.; Magee, D. E.; Bekele, A.; Williams, D. C.; Cullinan, G. J.; Bendele, R.; Kauffman, R. F.; Bensch, W. R.; Frolik, C. A.; Termine, J. D. and Bryant, H. U.: Raloxifene [Lyophilizate 139481 HCl] Prevents Bone Loss and Reduces Serum Cholesterol without Causing Uterine Hypertrophy in Ovariectomized Rats; J. Clin. Invest. 93: 63–69, 1994).

The invention also relates to pharmaceutical preparations that contain at least one compound of general formula I (or physiologically compatible addition salts with organic and inorganic acids of them) and the use of these compounds for the production of pharmaceutical agents, especially for treating estrogen-dependent diseases and tumors and pharmaceutical agents for hormone replacement therapy (HRT).

The compounds according to the invention and the acid addition salts are suitable for the production of pharmaceutical compositions and preparations. As active ingredients, the pharmaceutical compositions or pharmaceutical agents contain one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), pages 918 and ff.; issued by Czetsch-Lindenwald, Hilfsstoffe für Pharmazie und angrenzende Gebiete [Adjuvants for Pharmaceutics and Related Fields]; Pharm. Ind. Issue 2, 1961, pages 72 and ff.; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields] Cantor K G, Aulendorf in Württemberg 1971.

The compounds can be administered orally or parenterally, for example intraperitoneally, intramuscularly, subcutaneously or percutaneously. The compounds can also be implanted in the tissue. The amount of the compounds to be administered varies within a wide range and can cover any effective amount. Based on the condition to be treated and the type of administration, the amount of administered compound can be 0.1–25 mg/kg of body weight, preferably 0.5–5 mg/kg of body weight, per day. In humans, this corresponds to a daily dose of 5 to 1250 mg. The preferred daily dosage in humans is 50 to 200 mg. This is true especially for tumor therapy.

For oral administration, capsules, pills, tablets, coated tablets, etc., are suitable. In addition to the active ingredient, the dosage units can contain a physiologically compatible vehicle, such as, for example, starch, sugar, sorbitol, gelatin, lubricant, silicic acid, talc, etc. The individual dosage units for oral administration can contain, for example, 5 to 500 mg of active ingredient.

To achieve better bio-availability of the active ingredient, the compounds can also be formulated as cyclodextrin clathrates. For this purpose, the compounds are reacted with α-, β- or γ-cyclodextrin or derivatives thereof (PCT/EP95/02656).

For parenteral administration, the active ingredients can be dissolved or suspended in a physiologically compatible diluent. As diluent, very frequently oils with or without the addition of a solubilizer, a surfactant, a suspending agent or emulsifier are used. Examples of oils that are used are olive oil, peanut oil, cottonseed oil, soybean oil, castor oil and sesame oil.

The compounds of general formula I can also be formulated in the form of a solution that is determined for oral administration and that in addition to the active compound of general formula I contains
  a) a pharmaceutically compatible oil and/or
  b) a pharmaceutically compatible lipophilic surfactant and/or
  c) a pharmaceutically compatible hydrophilic surfactant and/or
  d) a pharmaceutically compatible water-miscible solvent.

In this respect, reference is made in addition to WO 97/21440.

The compounds can also be used in the form of a depot injection or an implant preparation, which can be formulated in such a way that a delayed release of active ingredient is made possible.

As inert materials, implants can also contain, for example, biodegradable polymers or synthetic silicones such as, for example, silicone gum. In addition, the active ingredients can be embedded in, for example, a patch for percutaneous administration.

For the production of intravaginal systems (e.g., vaginal rings) or intrauterine systems (e.g., pessaries, spirals) that are loaded with active compounds of general formula I, various polymers such as, for example, silicone polymers, ethylene vinyl acetate, polyethylene or polypropylene are suitable.

The compounds according to the invention can be produced as described below. The examples below are used for a more detailed explanation of the invention. Other compounds of general formula I can be obtained by an analogous procedure using analogous reagents in the data contained in the examples.

As processes to create side chain $R^7$ in the compounds according to the invention, especially also the methods of side-chain introduction and side-chain build-up that are described in EP 0 138 504 B1 are suitable, whereby then as a starting compound, instead of $\Delta^6$-nortestosterone, its 17-hydroxy group is acylated, and the 11β-fluorine compound 11β-fluorine-$\Delta^6$-androstenedione can be used. The reduction of the 17-keto group then takes place in a later stage.

The compounds of general formula I, in which $R^{31}$ is a radical of formula —C(O)$R^{33}$, can be converted by complete reduction of the keto group of the carboxylic acid amide with lithium aluminum hydride or similar reducing agents according to the method that is familiar to one skilled in the art into the compounds in which $R^{31}$ is then —CH$_2$—$R^{33}$.

A thio bridge in the side chain can be oxidized with sodium periodate into sulfoxide (Example 24n)); the sulfones are obtained from the sulfides with a peracid as an oxidizing agent, e.g., m-chloroperbenzoic acid.

The saponification of the ester groupings as well as esterification and etherification of free hydroxy groups is carried out in each case according to established processes of organic chemistry. By observing the various reactivity of the esterified and free 3- and 17-hydroxy group, the 3,17-diester can be cleaved selectively in 3-position, and the 3-hydroxy-17-acyloxy compound can then be additionally functionalized specifically in the 3-position; it is equally possible to esterify or to etherify the 3,17-dihydroxy compound selectively only in the 3-position and then to introduce specifically another radical into the 17-position as already in the 3-position.

The acid addition salts of the compounds of general formula I can also be produced from the compounds of general formula I according to standard processes.

The examples below are used for a more detailed explanation of the invention:

EXAMPLES

Example 1

11β-Fluoro-7α-{5-[methyl-(8,8,9,9,9-pentafluoro-nonyl)-amino]-pentyl}-estra-1,3,5(10)-triene-3,17β-diol a) 11β-Fluor-estr-4-ene-3,17-dione 4.6 ml of perfluorobutane-1-sulfonic acid fluoride is added in drops to 5.0 g of 11α-hydroxy-estr-4-ene-3,17-dione in 100 ml of toluene and 7.3 ml of 1,8-diazabicyclo[5,4,0]undec-7-ene at 0° C. After 30 minutes, the solution is diluted with ethyl acetate, washed with saturated sodium chloride solution, dried and concentrated by evaporation in a vacuum. After the crude product is chromatographed on silica gel with a hexane-ethyl acetate gradient, 3.8 g of 11β-fluor-estr-4-ene-3,17-dione with a melting point of 173–174° C. is obtained.

b) 11β-Fluoro-3-methoxy-estra-3,5-dien-17-one 7.8 g of 11β-fluor-estr-4-ene-3,17-dione is stirred in 40 ml of 2,2-dimethoxypropane with 780 mg of pyridinium-toluene-4-sulfonate for 5 hours at 80° C. Then, 1.5 ml of triethylamine is added, diluted with ethyl acetate and washed with saturated sodium chloride solution. After crystallization from methanol, 5.3 g of 11β-fluoro-3-methoxy-estra-3,5-dien-17-one with a melting point of 173° C. is obtained.

c) 11β-Fluor-estra-4,6-diene-3,17-dione 5 ml of a 10% sodium acetate solution and, in portions, 2.5 g of 1,3-dibromo-5,5-dimethylhydantoin are added in succession to 5.0 g of 11β-fluoro-3-methoxy-estra-3,5-dien-17-one in 50 ml of DMF at 0° C. After 30 minutes, 2.3 g of sodium sulfite and then 2.5 g of lithium bromide and 2.0 g of lithium carbonate are added and stirred for 2 hours at 100° C. The reaction mixture is stirred into ice water. The precipitated product is suctioned off, dissolved in ethyl acetate, washed with water, dried and concentrated by evaporation in a vacuum. After recrystallization from ethyl acetate, 3.6 g of 11β-fluor-estra-4,6-diene-3,17-dione with a melting point of 198° C. is obtained.

d) 11β-Fluoro-7α-(5-tert-butyl-dimethylsilyloxypentyl)-estr-4-ene-3,17-dione 7.9 g of magnesium in 40 ml of THF is reacted under nitrogen with a solution of 95.3 g of 1-bromo-5-tert-butyl-dimethylsilyloxypentane [Tetrahedron Letters 1982, 4147–4150] in 260 ml of THF to form the Grignard reagent. At −30° C., 32 g of copper(I) iodide and then, drop by drop, 29 g of 11β-fluor-estra-4,6-diene-3,17-dione in 290 ml of THF are added. After the reaction has been completed, it is mixed with 20.4 ml of glacial acetic acid, and the reaction mixture is stirred into ice water. The precipitated product is suctioned off, dissolved in ethyl acetate, washed neutral with water and dried. After the crude product is chromatographed on silica gel with a hexane-ethyl acetate gradient, 23.9 g of 11β-fluoro-7α-(5-tert-butyl-dimethylsilyloxypentyl)-estr-4-ene-3,17-dione is obtained as a foam.

e) 11β-Fluoro-7α-(5-hydroxypentyl)-estr-4-ene-3,17-dione

A solution of 23.1 g of 11β-fluoro-7α-(5-tert-butyl-dimethylsilyloxypentyl)-estr-4-ene-3,17-dione in 115 ml of THF and 64 ml of water is stirred with 128 ml of glacial acetic acid for 2.5 hours at 50° C. The reaction mixture is concentrated by evaporation in a vacuum, taken up in ethyl acetate, washed with water and dried. 20.4 g of 11β-fluoro-7α-(5-hydroxypentyl)-estr-4-ene-3,17-dione is obtained as a foam.

f) 7α-(5-Bromopentyl)-11β-fluor-estr-4-ene-3,17-dione

A solution of 33 g of 11β-fluoro-7α-(5-hydroxypentyl)-estr-4-ene-3,17-dione in 330 ml of dichloromethane is mixed at −5° C. with 28.9 g of triphenylphosphine and 36.7 g of carbon tetrabromide and stirred for 0.5 hour. Then, dichloromethane is added, and it is washed with water, saturated sodium bicarbonate and common salt solution. The organic phase is dried on sodium sulfate and concentrated by evaporation in a vacuum. Then, the crude product is chromatographed on silica gel with a hexane-ethyl acetate gradient. 28.5 g of 7α-(5-bromopentyl)-11β-fluor-estr-4-ene-3,17-dione with a melting point of 75–76° C. is obtained.

g) 7α-(5-Bromopentyl)-11β-fluoro-3-hydroxy-estra-1,3,5(10)-trien-17-one 17.0 g of copper(II) bromide is added to 27.8 g of 7α-(5-bromopentyl)-11β-fluor-estr-4-ene-3,17-dione in 190 ml of acetonitrile at 80° C. After 8 hours, the reaction mixture is stirred into water, extracted three times with ethyl acetate, and twice with ammonium chloride, washed with sodium bicarbonate and common salt, dried and concentrated by evaporation in a vacuum. After the crude product is chromatographed on silica gel with a hexane-ethyl acetate gradient, 20.4 g of 7α-(5-bromopentyl)-11β-fluoro-3-hydroxy-estra-1,3,5(10)-trien-17-one is obtained as colorless crystals with a melting point of 178° C.

h) 7α-(5-Bromopentyl)-11β-fluor-estra-1,3,5(10)-triene-3,17β-diol

A solution of 16.2 g of 7α-(5-bromopentyl)-11β-fluoro-3-hydroxy-estra-1,3,5(10)-trien-17-one in 162 ml of tetrahydrofuran as well as 90 ml of ethanol and 36 ml of water are mixed in portions at 0° C. with 4.7 g of sodium borohydride and stirred for 2 hours at 0° C. Then, it is added to water, extracted four times with ethyl acetate, washed with water and common salt solution, dried on sodium sulfate and concentrated by evaporation in a vacuum. 17.1 g of crude product is obtained. After chromatography on silica gel with hexane/ethyl acetate, 15.6 g of pure 7α-(5-bromopentyl)-11β-fluor-estra-1,3,5(10)-triene-3,17β-diol is obtained.

i) 11β-Fluoro-7α-[5-(methyl-amino)-pentyl]-estra-1,3,5(10)-triene-3,17β-diol

A solution of 2 g of 7α-(5-bromopentyl)-11β-fluor-estra-1,3,5(10)-triene-3,17β-diol in 20 ml of dimethylformamide is stirred with 8 ml of a 40% aqueous methylamine solution for 3.5 hours at 80° C. Then, it is added to water, extracted three times with ethyl acetate, washed with water and common salt solution, dried on sodium sulfate and concentrated by evaporation in a vacuum. 1.77 g of 11β-fluoro-7α-[5-(methyl-amino)-pentyl]-estra-1,3,5(10)-triene-3,17β-diol is obtained.

j) 11β-Fluoro-7α-{5-[methyl-(8,8,9,9,9-pentafluoro-nonyl)-amino]-pentyl}-estra-1,3,5(10)-triene-3,17β-diol A solution of 1.77 g of 11β-fluoro-7α-[5-(methyl-amino)-pentyl]-estra-1,3,5(10)-triene-3,17β-diol in 18 ml of dimethylformamide is stirred with 1.4 g of 8,8,9,9,9-pentafluoro-nonyltosylate for 1 hour at a bath temperature of 80° C. Then, it is added to water, extracted three times with ethyl acetate, washed with water and common salt solution, dried on sodium sulfate, concentrated by evaporation in a vacuum and chromatographed on silica gel with dichloromethane/methanol. 11β-Fluoro-7α-{5-[methyl-(8,8,9,9,9-pentafluoro-nonyl)-amino]-pentyl}-estra-1,3,5(10)-triene-3,17β-diol is obtained as crystals with a melting point of 110° C.

Production of the Starting Compounds 8,8,9,9,9-Pentafluoro-nonyltosylate a) 4-Benzyloxy-butan-1-ol 42 g of sodium hydride (60%) is introduced at room temperature in portions into 900 ml of absolute DMF. 88.6 ml of 1,4-butanediol in 450 ml of absolute DMF is added in drops to the suspension that is cooled to −20° C. in such a way that the internal temperature does not exceed −15° C. After the addition has been completed, a solution of 121 ml of benzyl bromide in 870 ml of absolute DMF is quickly added in drops, and then the reaction mixture is stirred for 30 minutes at room temperature. The reaction is completed by careful addition of 315 ml of water. For working-up, the reaction mixture is stirred into 1.5 l of water and extracted 3 times with 1 l of ether in each case. The ethereal phases are combined, washed with water, dried on magnesium sulfate and concentrated by evaporation in a vacuum. Chromatography on silica gel with a hexane-ethyl acetate gradient yields 105 g of 4-benzyloxy-butan-1-ol as an oil.

b) 4-Benzyloxy-1-bromo-butane 239 g of tetrabromomethane is added in portions to the solution of 105 g of 4-benzyloxy-butan-1-ol and 191 g of triphenylphosphine in 1 l of methylene chloride that is cooled to −15° C., and after the addition has been completed, it is stirred for 1 hour at 0° C. After the reaction mixture was concentrated by evaporation in a vacuum, the purification by chromatography on silica gel is carried out with a hexane-ethyl acetate gradient. 133 g of 4-benzyloxy-1-bromo-butane is obtained as an oil.

c) 1-Benzyloxy-8,8,9,9,9-pentafluoro-nonane

First at room temperature, 10% of a solution of 20 g of 4-benzyloxy-1-bromo-butane in 20 ml of absolute THF is added to a suspension of 2.23 g of magnesium chips in 58 ml of absolute THF. After the reaction has started, which can be achieved by adding iodine, the residual solution is added in drops in such a way that the internal temperature is kept at 40° C. After the addition has been completed, it is stirred for 1 more hour at room temperature before being decanted off from the excess magnesium, and the solution is moved into a dropping funnel. Now, this solution is added in drops simultaneously with a solution that consists of 21 g of 1,1,1,2,2-pentafluoro-5-iodo-pentane in 97 ml of absolute THF to a solution of 555 mg of copper(II) chloride and 350 mg of lithium chloride in 58 ml of absolute THF at 0° C. It is stirred for 1 more hour at room temperature, and then the reaction mixture is stirred into saturated ammonium chloride solution, extracted 3 times with ether, the organic phase is dried on magnesium sulfate and concentrated by evaporation in a vacuum. Preparative column chromatography on silica gel with a hexane-ethyl acetate gradient yields 22 g of largely purified 1-benzyloxy-8,8,9,9,9-pentafluoro-nonane as an oil.

d) 8,8,9,9,9-Pentafluoro-nonan-1-ol 16 g of 1-benzyloxy-8,8,9,9,9-pentafluoro-nonane is dissolved in 700 ml of absolute methylene chloride, mixed with 18.4 ml of N,N-dimethylaniline at 0° C. and stirred for 5 minutes. Then, 26.4 g of aluminum trichloride is added in portions, and the reaction mixture is heated for 45 minutes to 50° C. For working-up, the batch is allowed to come to room temperature, it is stirred into 2N hydrochloric acid, extracted 3 times with methylene chloride, dried on magnesium sulfate and concentrated by evaporation in a vacuum. The crude product is chromatographed on silica gel with a hexane-ethyl acetate gradient. 8.6 g of 8,8,9,9,9-pentafluoro-nonan-1-ol is obtained as an oil.

e) 8,8,9,9,9-Pentafluoro-nonyltosylate 3.0 g of 8,8,9,9,9-pentafluoro-nonan-1-ol is dissolved in 26 ml of absolute pyridine, 3.1 g of p-toluenesulfonyl chloride is added at 0° C. and stirred for 1.5 hours under cold conditions. Then, the reaction mixture is added to water, extracted 3 times with ether, dried on magnesium sulfate and concentrated by evaporation in a vacuum. Preparative column chromatography on silica gel with a hexane-ethyl acetate gradient results in 4.1 g of 8,8,9,9,9-pentafluoro-nonyltosylate as a clear oil.

9,9,10,10,10-Pentafluoro-decyltosylate a) 5-Benzyloxy-pentan-1-ol 31.5 g of sodium hydride (60%) is introduced at room temperature in portions in 900 ml of absolute DMF. 104.8 ml of 1,5-pentanediol in 450 ml of absolute DMF is added in drops to the suspension that is cooled to −20° C. in such a way that the internal temperature does not exceed −15° C. After the addition has been completed, a solution of 121 ml of benzyl bromide in 870 ml of absolute DMF is quickly added in drops, and then the reaction mixture is stirred for 30 minutes at room temperature. The reaction is completed by careful addition of 315 ml of water. For working-up, the reaction mixture is stirred into 1.5 l of water and extracted 3 times with 1 l of ether in each case. The ethereal phases are combined, washed with water, dried on magnesium sulfate and concentrated by evaporation in a vacuum. Chromatography on silica gel with a hexane-ethyl acetate gradient yields 85 g of 5-benzyloxy-pentan-1-ol as an oil.

b) 5-Benzyloxy-1-bromo-pentane 179 g of tetrabromomethane is added in portions to the solution of 85 g of 5-benzyloxy-pentan-1-ol and 143 g of triphenylphosphine in 720 ml of methylene chloride that is cooled to −15° C., and after the addition has been completed, it is stirred for 3 hours at 0° C. After the reaction mixture was concentrated by evaporation in a vacuum, the purification is carried out by chromatography on silica gel with a hexane-methylene chloride gradient. 71 g of 5-benzyloxy-1-bromo-pentane is obtained as an oil.

c) 1-Benzyloxy-9,9,10,10,10-pentafluoro-decane

First at room temperature, 10% of a solution of 21.1 g of 5-benzyloxy-1-bromo-pentane in 20 ml of absolute THF is added to a suspension of 2.23 g of magnesium chips in 58 ml of absolute THF. After the reaction has started, which can be achieved by adding iodine, the residual solution is added in drops in such a way that the internal temperature is kept at 40° C. After the addition has been completed, it is stirred for 1 more hour at room temperature before being decanted off from the excess magnesium, and the solution is moved into a dropping funnel. Now, this solution is simultaneously added in drops with a solution of 21 g of 1,1,1,2,2-pentafluoro-5-iodo-pentane in 97 ml of absolute THF to a solution of 555 mg of copper(II) chloride and 350 mg of lithium chloride in 58 ml of absolute THF at 0° C. It is stirred for 1 more hour at room temperature, then the reaction mixture is stirred into saturated ammonium chloride solution, extracted 3 times with ether, the organic phase is dried on magnesium sulfate and concentrated by evaporation in a vacuum. 26.8 g of crude product is obtained, which is used without further purification in the next stage.

d) 9,9,10,10,10-Pentafluoro-decan-1-ol 26 g of 1-benzyloxy-9,9,10,10,10-pentafluoro-decane is dissolved in 1000 ml of absolute methylene chloride, mixed with 28.9 ml of N,N-dimethylaniline at 0° C. and stirred for 5 minutes. Then, 41.1 g of aluminum trichloride is added in portions, and the reaction mixture is heated for 45 minutes to 50° C. For working-up, the batch is allowed to come to room temperature, it is stirred into 2N hydrochloric acid, extracted 3 times with methylene chloride, the organic phase is washed with common salt solution, dried on magnesium sulfate and concentrated by evaporation in a vacuum. The crude product is chromatographed on silica gel with a hexane-ethyl acetate gradient. 7.8 g of 9,9,10,10,10-pentafluoro-decan-1-ol is obtained as an oil.

e) 9,9,10,10,10-Pentafluoro-decyltosylate 1.0 g of 9,9,10,10,10-pentafluoro-decan-1-ol is dissolved in 8 ml of absolute pyridine, 985 mg of p-toluenesulfonyl chloride is added at 0° C. and stirred for 2 hours under cold conditions. Then, the reaction mixture is added to water, extracted 3 times with ether, dried on magnesium sulfate and concentrated by evaporation in a vacuum. Preparative column chromatography on silica gel with a hexane-ethyl acetate gradient provides 1.5 g of 9,9,10,10,10-pentafluoro-decyltosylate as an oil.

N-Methyl-[3-(4,4,5,5,5-pentafluoro-pentylthio)-propyl]-amine a) 3-Iodopropyl-4,4,5,5,5-pentafluoro-pentyl Sulfide A solution of 22.8 g of 3-chloropropyl-4,4,5,5,5-pentafluoro-pentylsulfide in 500 ml of ethyl methyl ketone is stirred with 40 g of sodium iodide for 5 hours at a bath temperature of 100° C. under nitrogen. Then, it is evaporated to the dry state in a vacuum, added to water, extracted three times with ethyl acetate, washed neutral and dried on sodium sulfate and concentrated by evaporation in a vacuum. 30.6 g of 3-iodopropyl-4,4,5,5,5-pentafluoro-pentyl sulfide is obtained.

b) N-Methyl-[3-(4,4,5,5,5-pentafluoro-pentylthio)-propyl]-amine 45 g of methylamine is condensed in a solution of 30.6 g of 3-iodopropyl-4,4,5,5,5-pentafluoro-pentylsulfide in 200 ml of absolute tetrahydrofuran at a bath temperature of −78° C., and it is stirred for 1.5 hours at room temperature as well as for 4 hours at 60° C. in a pressurized reactor. To open the reactor, it is allowed to cool overnight to room temperature and then to −78° C. Then, it is allowed to come to room temperature, excess methylamine is evaporated, it is diluted with ethyl acetate, washed neutral, dried on sodium sulfate, concentrated by evaporation in a vacuum and chromatographed on silica gel with dichloromethane/methanol. 15.7 g of N-methyl-[3-(4,4,5,5,5-pentafluoro-pentylthio)-propyl]-amine is obtained as an oil.

N-Methyl-[3-(4,4,5,5,5-pentafluoro-pentanesulfonyl)-propyl]-amine a) 3-Chloropropyl-4,4,5,5,5-pentafluoro-pentanesulfone A solution of 23 g of 3-chloropropyl-4,4,5,5,5-pentafluoro-pentylsulfide in 230 ml of chloroform is mixed in portions at 0° C. with 41.8 g of 70% m-chloroperbenzoic acid and stirred for 1.5 hours at room temperature. Then, it is diluted with dichloromethane, washed with sodium hydrogen sulfite, sodium bicarbonate and common salt solution, dried on sodium sulfate and concentrated by evaporation in a vacuum. 23.8 g of pure 3-chloropropyl-4,4,5,5,5-pentafluoro-pentanesuflone is obtained as crystals with a melting point of 74–76° C.

b) 3-Iodopropyl-4,4,5,5,5-pentafluoro-pentanesulfone

A solution of 23.5 g of 3-chloropropyl-4,4,5,5,5-pentafluoro-pentanesulfone in 500 ml of ethylmethylketone is stirred with 40 g of sodium iodide for 5 hours at a bath temperature of 100° C. under nitrogen. Then, it is evaporated to the dry state in a vacuum, added to water, extracted three times with ethyl acetate, washed neutral and dried on sodium sulfate and concentrated by evaporation in a vacuum. 30.6 g of 3-iodopropyl-4,4,5,5,5-pentafluoro-pentanesulfone is obtained as crystals with a melting point of 88–89° C.

c) N-Methyl-[3-(4,4,5,5,5-pentafluoro-pentanesulfonyl)-propyl]-amine

A solution of 23.5 g of 3-iodopropyl-4,4,5,5,5-pentafluoro-pentanesulfone in 200 ml of absolute tetrahydrofuran is condensed at a bath temperature of –78° C. [with] 44 g of methylamine, and it is stirred for 1.5 hours at room temperature as well as for 4 hours at 60° C. in a pressurized reactor. To open the reactor, it is allowed to cool overnight to room temperature and then to –78° C. Then, it is allowed to come to room temperature, excess methylamine is evaporated, it is diluted with ethyl acetate, washed neutral, dried on sodium sulfate, concentrated by evaporation in a vacuum and chromatographed on silica gel with dichloromethane/methanol. 14.8 g of N-methyl-[3-(4,4,5,5,5-pentafluoro-pentanesulfonyl)-propyl]-amine is obtained as crystals with a melting point of 55–57° C.

1-Bromo-5-tert-butyldimethylsilyloxypentane a) 5-Bromo-1-pentanol 50 ml of concentrated sulfuric acid is added in drops to a solution of 50 g of 5-bromopentylacetate in 1.6 l of methanol, and the mixture is stirred for 30 hours at room temperature. The methanol is drawn off in a vacuum, the residue is taken up in diethyl ether, washed neutral with saturated common salt solution, dried on sodium sulfate and concentrated by evaporation. 28 g of 5-bromo-1-pentanol is obtained as a crude product.

b) 1-Bromo-5-tert-butyldimethylsilyloxypentane

A solution of 28 g of crude 5-bromo-1-pentanol in 144 ml of tetrahydrofuran is mixed with 24 g of imidazole. Then, a solution of 30.3 g of tert-butyldimethylchlorosilane in 46 ml of tetrahydrofuran is added in drops and stirred for 4 hours at room temperature. The reaction mixture is poured into water, shaken out with diethyl ether, the organic phase is washed 4 times with water, dried on sodium sulfate and concentrated by evaporation. The crude product is chromatographed on silica gel with hexane/diethyl ether. 42 g of the title compound is obtained as a colorless liquid.

Example 2

11β-Fluoro-7α-{5-[methyl-nonyl-amino]-pentyl}-estra-1,3,5(10)-triene-3,17β-diol a) 7α-(5-Chloropentyl)-11β-fluor-estr-4-ene-3,17-dione First 20% of a solution of 39 ml of 1-bromo-5-chloropentane in 300 ml of THF is added under nitrogen to a suspension of 7.2 g of magnesium chips in 100 ml of THF. After the reaction has started, which can be achieved by adding iodine and dibromomethane, the residual solution is added in drops in such a way that the internal temperature does not exceed 35° C. In a second flask, 51.2 g of lithium bromide is added to a suspension of 28.1 g of copper(I) iodide in 130 ml of THF at 0° C., whereby the internal temperature climbs to 40° C. Without cooling, 49.4 ml of 1,3-dimethyl-3,4,5,6-tetrahydro-(1H)-pyrimidin-2-one is now added and stirred for 15 minutes at 40° C. A clear solution is obtained, which was added in drops to the Grignard solution that is cooled to –50° C. Then, it is stirred for 15 more minutes at –30° C. and mixed at –70° C. drop by drop with a solution of 25 g of 11β-fluor-estra-4,6-diene-3,17-dione in 260 ml of THF, 26 ml of 1,3-dimethyl-3,4,5,6-tetrahydro-(1H)-pyrimidin-2-one and 59 ml of trimethylchlorosilane in such a way that the internal temperature does not exceed –65° C. It is stirred for 30 minutes under cold conditions, then 34.7 ml of glacial acetic acid is added in drops, the cooling bath is removed and stirred for 1 more hour at room temperature. For working-up, the reaction mixture is added to 1.5 l of water, diluted with the same amount of ethyl acetate, the precipitate is separated on Celite, rewashed with ethyl acetate, the aqueous phase is extracted 3 times with ethyl acetate, washed with sodium bicarbonate and common salt solution, dried on magnesium sulfate and concentrated by evaporation in a vacuum. After the crude product is chromatographed on silica gel with a hexane-ethyl acetate gradient, 22.1 g of 7α-(5-chloropentyl)-11β-fluor-estr-4-ene-3,17-dione is obtained.

b) 7α-(5-Chloropentyl)-11β-fluoro-3-hydroxy-estra-1,3,5(10)-trien-17-one 25.4 g of copper(II) bromide and 4.9 g of lithium bromide in 95 ml of anhydrous acetonitrile are added to 22.1 g of 7α-(5-chloropentyl)-11β-fluor-estr-4-ene-3,17-dione in 160 ml of anhydrous acetonitrile at 80° C. After 20 minutes, the reaction mixture is cooled to 0° C., and 200 ml of saturated sodium bicarbonate solution is added in drops. Then, the solution is stirred into 750 ml of water, brought to pH=6 with 2N hydrochloric acid, extracted 3 times with ethyl acetate, washed with common salt solution, dried on magnesium sulfate and concentrated by evaporation in a vacuum. Chromatography of the crude product on silica gel with a hexane-ethyl acetate gradient yields 14.7 g of 7α-(5-chloropentyl)-11β-fluoro-3-hydroxy-estra-1,3,5(10)-trien-17-one.

c) 11β-Fluoro-3-hydroxy-7α-(5-iodopentyl)-estra-1,3,5(10)-trien-17-one 5.0 g of 7α-(5-chloropentyl)-11β-fluoro-3-hydroxy-estra-1,3,5(10)-trien-17-one is dissolved in 80 ml of ethylmethylketone, mixed with 5.7 g of sodium iodide and stirred overnight at a bath temperature of 90° C. For working-up, the reaction mixture is cooled to room temperature, stirred into water, extracted 3 times with ethyl acetate, washed with common salt solution, dried on magnesium sulfate and concentrated by evaporation in a vacuum. 6.8 g of 11β-fluoro-3-hydroxy-7α-(5-iodopentyl)-estra-1,3,5(10)-trien-1-one is obtained as a crude product, which is used without further purification in the next stage.

c) 11β-Fluoro-3-hydroxy-7α-[5-(methyl-amino)-pentyl]-estra-1,3,5(10)-trien-17-one 5.1 g of methylamine is condensed in a solution of 6.8 g of 11β-fluoro-3-hydroxy-7α-(5-iodopentyl)-estra-1,3,5(10)-trien-17-one in 35 ml of anhydrous tetrahydrofuran at –78° C., and it is stirred overnight at room temperature in a pressurized reactor. After the pressurized reactor was opened at –20° C., it is allowed to come to room temperature to allow excess methylamine to evaporate off. Then, the reaction solution is added to saturated sodium bicarbonate solution, extracted 3 times with ethyl acetate, dried on magnesium sulfate and concentrated by evaporation in a vacuum. 6.7 g of 11β-fluoro-3-hydroxy-7α-[5-(methyl-amino)-pentyl]-estra-1,3,5(10)-trien-17-one is obtained as a crude product.

d) 11β-Fluoro-3-hydroxy-7α-{5-[methyl-nonyl-amino]-pentyl}-estra-1,3,5(10)-trien-17-one 526 mg of 11β-fluoro-3-hydroxy-7α-[5-(methyl-amino)-pentyl]-estra-1,3,5(10)-trien-17-one and 127 mg of iodononane are dissolved in 5 ml of anhydrous DMF and stirred for 4 hours at a bath temperature of 100° C. For working-up, the batch is added to semi-saturated sodium bicarbonate solution, extracted 3 times with methylene chloride, dried on magnesium sulfate and concentrated by evaporation in a vacuum. Preparative column chromatography yields 85 mg of 11β-fluoro-3-hydroxy-7α-{5-[methyl-nonyl-amino]-pentyl}-estra-1,3,5(10)-trien-17-one as a foam.

e) 11β-Fluoro-7α-{5-[methyl-nonyl-amino]-pentyl}-estra-1,3,5(10)-triene-3,17β-diol 85 mg of 11β-fluoro-3-hydroxy-7α-{5-[methyl-nonyl-amino]-pentyl}-estra-1,3,5(10)-trien-17-one is dissolved in 3 ml of methanol and mixed with 25 mg of sodium borohydride. After 30 minutes of stirring at room temperature, the solvent is drawn off in a vacuum for the most part, the residue is mixed with common salt solution, extracted 3 times with methylene chloride, dried on magnesium sulfate and concentrated by evaporation in a vacuum. Preparative thin-layer chromatography with methylene chloride/methanol=9/1+0.5% triethylamine as a mobile solvent provides 33 mg of 11β-fluoro-7α-{5-[methyl-nonyl-amino]-pentyl}-estra-1,3,5(10)-triene-3,17β-diol as a foam.

Example 3

11β-Fluoro-7α-{5-[methyl-(9,9,10,10,10-pentafluoro-decyl)-amino]-pentyl}-estra-1,3,5(10)-triene-3,17β-diol a) 11β-Fluoro-3-hydroxy-7α-{5-[methyl-(9,9,10,10,10-pentafluoro-decyl)-amino]-pentyl}-estra-1,3,5(10)-trien-17-one A solution of 260 mg of 11β-fluoro-3-hydroxy-7α-[5-(methyl-amino)-pentyl]-estra-1,3,5(10)-trien-17-one in 3 ml of dimethylformamide is stirred with 180 mg of 9,9,10,10,10-pentafluorodecyltosylate for 1 hour at a bath temperature of 100° C. Then, it is added to semi-saturated sodium bicarbonate solution, extracted three times with methylene chloride, dried on magnesium sulfate, concentrated by evaporation in a vacuum and chromatographed on silica gel with dichloromethane/methanol/triethylamine. 92 mg of 11β-fluoro-3-hydroxy-7α-{5-[methyl-(9,9,10,10,10-pentafluoro-decyl)-amino]-pentyl}-estra-1,3,5(10)-trien-17-one is obtained as a foam, $[\alpha]_D=+48°$ (c=1.0 in chloroform).

b) 11β-Fluoro-7α-{5-[methyl-(9,9,10,10,10-pentafluoro-decyl)-amino]-pentyl}-estra-1,3,5(10)-triene-3,17β-diol 92 mg of 11β-fluoro-3-hydroxy-7α-{5-[methyl-(9,9,10,10-pentafluoro-decyl)-amino]-pentyl}-estra-1,3,5(10)-trien-17-one is dissolved in 2 ml of methanol and mixed with 23 mg of sodium borohydride. After 1 hour of stirring at room temperature, the solvent is drawn off in a vacuum for the most part, the residue is mixed with common salt solution, extracted 3 times with methylene chloride, dried on magnesium sulfate and concentrated by evaporation in a vacuum. Preparative thin-layer chromatography with methylene chloride/methanol=9/1 as a mobile solvent provides 42 mg of 11β-fluoro-7α-{5-[methyl-(9,9,10,10,10-pentafluoro-decyl)-amino]-pentyl}-estra-1,3,5(10)-triene-3,17β-diol as a foam, $[\alpha]_D=+44°$ (c=1.0 in chloroform).

Example 4

11β-Fluoro-7α-{6-[methyl-(8,8,9,9,9-pentafluoro-nonyl)-amino]-hexyl}-estra-1,3,5(10)-triene-3,17β-diol a) 7α-(6-Chlorohexyl)-11β-fluor-estr-4-ene-3,17-dione First 30 ml of a solution of 41 ml of 1-bromo-6-chlorohexane in 270 ml of THF is added under nitrogen to a suspension of 6.8 g of magnesium chips in 100 ml of THF. After the reaction has started, the residual solution is added in drops in such a way that the internal temperature does not exceed 35° C. In a second flask, 48.1 g of lithium bromide is added to a suspension of 26.4 g of copper(I) iodide in 120 ml of THF at 0° C., whereby the internal temperature climbs to 40° C. Without cooling, 46.4 ml of 1,3-dimethyl-3,4,5,6-tetrahydro-(1H)-pyrimidin-2-one is now added and stirred for 30 minutes at 40° C. A clear solution is obtained, which is added in drops to the Grignard solution that is cooled to −40° C. Then, it is stirred for 30 more minutes at −30° C. and mixed drop by drop at −50° C. with a solution of 23.5 g of 11β-fluor-estra-4,6-diene-3,17-dione in 230 ml of THF, 24.6 ml of 1,3-dimethyl-3,4,5,6-tetrahydro-(1H)-pyrimidin-2-one and 55 ml of trimethylchlorosilane in such a way that the internal temperature does not exceed −40° C. It is stirred for 1 hour under cold conditions, then 32 ml of glacial acetic acid is added in drops, the cooling bath is removed and stirred for 1 more hour at room temperature. For working-up, the reaction mixture is added to 1.5 l of water, diluted with the same amount of ethyl acetate, the precipitate is separated overnight on Celite, rewashed with ethyl acetate, the aqueous phase is extracted 3 times with ethyl acetate, washed with sodium bicarbonate and common salt solution, dried on magnesium sulfate and concentrated by evaporation in a vacuum. After the crude product is chromatographed on silica gel with a hexane-ethyl acetate gradient, 25.2 g of 7α-(6-chlorohexyl)-11β-fluor-estr-4-ene-3,17-dione is obtained.

b) 7α-(6-Chlorohexyl)-11β-fluoro-3-hydroxy-estra-1,3,5(10)-trien-17-one 28.1 g of copper(II) bromide and 5.4 g of lithium bromide in 105 ml of anhydrous acetonitrile are added to 25.2 g of 7α-(6-chlorohexyl)-11β-fluor-estr-4-ene-3,17-dione in 175 ml of anhydrous acetonitrile at 80° C. After 15 minutes, the reaction mixture is cooled to 0° C., and 250 ml of saturated sodium bicarbonate solution is added in drops. Then, the solution is stirred into 1 liter of water, brought to pH=6 with 2N hydrochloric acid, extracted 3 times with ethyl acetate, washed with common salt solution, dried on magnesium sulfate and concentrated by evaporation in a vacuum. Chromatography of the crude product on silica gel with a hexane-ethyl acetate gradient yields 5.7 g of 7α-(6-chlorohexyl)-11β-fluoro-3-hydroxy-estra-1,3,5(10)-trien-17-one as a foam.

c) 11β-Fluoro-3-hydroxy-7α-(6-iodohexyl)-estra-1,3,5(10)-trien-17-one 2.7 g of 7α-(6-chlorohexyl)-11β-fluoro-3-hydroxy-estra-1,3,5(10)-trien-17-one is dissolved in 40 ml of ethylmethylketone, mixed with 3.0 g of sodium iodide and stirred overnight at a bath temperature of 90° C. For working-up, the reaction mixture is cooled to room temperature, stirred into water, extracted 3 times with ethyl acetate, washed with common salt solution, dried on magnesium sulfate and concentrated by evaporation in a vacuum. 3.4 g of 11β-fluoro-3-hydroxy-7α-(6-iodohexyl)-estra-1,3,5(10)-trien-17-one is obtained as a crude product, which is used without further purification in the next stage.

d) 11β-Fluoro-3-hydroxy-7α-[6-(methyl-amino)-hexyl]-estra-1,3,5(10)-trien-17-one 718 mg of methylamine is condensed in a solution of 960 mg of 11β-fluoro-3-hydroxy-7α-(6-iodohexyl)-estra-1,3,5 (10)-trien-17-one in 9 ml of anhydrous tetrahydrofuran at −78° C., and it is stirred overnight at room temperature in a pressurized reactor. After the pressurized reactor was opened at −20° C., it is allowed to come to room temperature to allow excess methylamine to evaporate off. Then, the reaction solution is added to saturated sodium bicarbonate solution, extracted 3 times with ethyl acetate, dried on sodium sulfate and concentrated by evaporation in a vacuum. 763 mg of 11β-fluoro-3-hydroxy-7α-[5-(methyl-amino)-hexyl]-estra-1,3,5(10)-trien-17-one is obtained as a crude product.

e) 11β-Fluoro-3-hydroxy-7α-{6-[methyl-(8,8,9,9,9-pentafluoro-nonyl)-amino]-hexyl}-estra-1,3,5(10)-trien-17-one A solution of 381 mg of 11β-fluoro-3-hydroxy-7α-[6-(methyl-amino)-hexyl]-estra-1,3,5(10)-trien-17-one in 5 ml of dimethylformamide is stirred with 200 mg of 8,8,9,9,9-pentafluorononyltosylate for 2 hours at a bath temperature of 100° C. Then, it is added to semi-saturated sodium bicarbonate solution, extracted three times with methylene chloride, dried on magnesium sulfate, concentrated by evaporation in a vacuum and chromatographed on silica gel with dichloromethane/methanol. 90 mg of 11β-fluoro-3-hydroxy-7α-{6-[methyl-(8,8,9,9,9-pentafluoro-nonyl)-amino]-hexyl}-estra-1,3,5(10)-trien-17-one is obtained as a foam.

f) 11β-Fluoro-7α-{6-[methyl-(8,8,9,9,9-pentafluoro-nonyl)-amino]-hexyl}-estra-1,3,5(10)-triene-3,17β-diol 89 mg of 11β-fluoro-3-hydroxy-7α-{6-[methyl-(8,8,9,9,9-pentafluoro-nonyl)-amino]-hexyl}-estra-1,3,5(10)-trien-17-one is dissolved in 2 ml of methanol and mixed with 22 mg of sodium borohydride. After 1 hour of stirring at room temperature, the solvent is drawn off in a vacuum for the most part, the residue is mixed with common salt solution, extracted 3 times with methylene chloride, dried on magnesium sulfate and concentrated by evaporation in a vacuum. Preparative thin-layer chromatography with methylene chloride/methanol=9/1 as a mobile solvent provides 53 mg of 11β-fluoro-7α-{5-[methyl-(8,8,9,9,9-pentafluoro-nonyl)-amino]-hexyl}-estra-1,3,5(10)-triene-3,17β-diol as a foam, $[\alpha]_D$=+32° (c=1.0 in chloroform).

Example 5

11β-Fluoro-7α-{6-[methyl-(9,9,10,10,10-pentafluoro-decyl)-amino]-hexyl}-estra-1,3,5(10)-triene-3,17β-diol a) 11β-Fluoro-3-hydroxy-7α-{6-[methyl-(9,9,10,10,10-pentafluoro-decyl)-amino]-hexyl}-estra-1,3,5(10)-trien-17-one A solution of 381 mg of 11β-fluoro-3-hydroxy-7α-[6-(methyl-amino)-hexyl]-estra-1,3,5(10)-trien-17-one in 5 ml of dimethylformamide is stirred with 180 mg of 9,9,10,10,10-pentafluoro-decyltosylate for 2 hours at a bath temperature of 100° C. Then, it is added to semi-saturated sodium bicarbonate solution, extracted three times with methylene chloride, dried on magnesium sulfate, concentrated by evaporation in a vacuum and chromatographed on silica gel with dichloromethane/methanol/triethylamine. 121 mg of 11β-fluoro-3-hydroxy-7α-{6-[methyl-(9,9,10,10,10-pentafluoro-decyl)-amino]-hexyl}-estra-1,3,5(10)-trien-17-one is obtained as a foam, $[\alpha]_D$=+59° (c=1.0 in chloroform).

b) 11β-Fluoro-7α-{6-[methyl-(9,9,10,10,10-pentafluoro-decyl)-amino]-hexyl}-estra-1,3,5(10)-triene-3,17β-diol 120 mg of 11β-fluoro-3-hydroxy-7α-{6-[methyl-(9,9,10,10,10-pentafluoro-decyl)-amino]-hexyl}-estra-1,3,5(10)-trien-17-one is dissolved in 2.5 ml of methanol and mixed in portions with 29 mg of sodium borohydride. After 30 minutes of stirring at room temperature, the solvent is drawn off in a vacuum for the most part, the residue is mixed with water, extracted 3 times with methylene chloride, dried on magnesium sulfate and concentrated by evaporation in a vacuum. 106 mg of 11β-fluoro-7α-{5-[methyl-(9,9,10,10,10-pentafluoro-decyl)-amino]-hexyl}-estra-1,3,5(10)-triene-3,17-diol is obtained as a foam, $[\alpha]_D$=+38° (c=0.5 in chloroform).

Example 6

11β-Fluoro-7α-(5-(methyl-amino)-pentyl)-estra-1,3,5(10)-triene-3,17β-diol

11β-Fluoro-7α-(5-(methyl-amino)-pentyl)-estra-1,3,5(10)-triene-3,17β-diol 880 mg of 11β-fluoro-3-hydroxy-7α-(5-(methyl-amino)-pentyl)-estra-1,3,5(10)-trien-17-one is dissolved in 15 ml of methanol, mixed in portions with 252 mg of sodium borohydride and stirred for 15 minutes at room temperature. For working-up, the reaction solution is added to saturated common salt solution, extracted several times with methylene chloride, the organic phases are washed with water, dried on magnesium sulfate and concentrated by evaporation in a vacuum. 540 mg of 11β-fluoro-7α-(5-(methyl-amino)-pentyl)-estra-1,3,5(10)-triene-3,17β-diol is obtained as a foam, $[\alpha]_D$=+63° (c=0.5 in chloroform).

Example 7

11β-Fluoro-7α-(5-pyrrolidin-1-yl-pentyl)-estra-1,3,5(10)-triene-3,17β-diol a) 11β-Fluoro-3-hydroxy-7α-(5-pyrrolidin-1-yl-pentyl)-estra-1,3,5(10)-trien-17-one A solution of 1.0 g of 11β-fluoro-3-hydroxy-7α-(5-iodopentyl)-estra-1,3,5(10)-trien-17-one in 10 ml of dimethylformamide is stirred with 0.24 ml of pyrrolidine for 2 hours at a bath temperature of 100° C. Then, it is added to saturated sodium bicarbonate solution, extracted three times with methylene chloride, dried on magnesium sulfate, concentrated by evaporation in a vacuum and chromatographed on silica gel with dichloromethane/methanol/triethylamine. 367 mg of 11β-fluoro-3-hydroxy-7α-(5-pyrrolidin-1-yl-pentyl)-estra-1,3,5(10)-trien-17-one is obtained as a foam.

b) 11β-Fluoro-7α-(5-pyrrolidin-1-yl-pentyl)-estra-1,3,5(10)-triene-3,17β-diol 324 mg of 11β-fluoro-3-hydroxy-7α-(5-pyrrolidin-1-yl-pentyl)-estra-1,3,5(10)-trien-17-one is dissolved in 10 ml of methanol and mixed with 63 mg of sodium borohydride. After 1.5 hours of stirring at room temperature, the batch is added to semi-saturated common salt solution, extracted 3 times with methylene chloride, dried on magnesium sulfate and concentrated by evaporation in a vacuum. After the crude product is chromatographed on silica gel with a methylene chloride-methanol gradient, 192 mg of 11β-fluoro-7α-(5-pyrrolidin-1-yl)-pentyl)-estra-1,3,5(10)-triene-3,17β-diol with a melting point of 95–118° C. is obtained.

Example 8

11β-Fluoro-7α-{5-[methyl-(4,4,5,5,5-pentafluoro-pentyl)-amino]-pentyl}-estra-1,3,5(10)-triene-3,17β-diol a) 11β-Fluoro-3-hydroxy-7α-{5-[methyl-(4,4,5,5,5-pentafluoro-pentyl)-amino]-pentyl}-estra-1,3,5(10)-trien-17-one 500 mg of 11β-fluoro-3-hydroxy-7α-(5-(methyl-amino)-pentyl)-estra-1,3,5(10)-trien-17-one is dissolved in 15 ml of ethylmethylketone, mixed with 1.1 g of potassium carbonate and 1.5 ml of 1,1,1,2,2-pentafluor-5-iodo-pentane and refluxed for 2.5 hours. For working-up, the reaction mixture is cooled to room temperature, stirred into saturated common salt solution, extracted with ethyl acetate, dried on magnesium sulfate and concentrated by evaporation in a vacuum. Preparative column chromatography on silica gel with a methylene chloride-methanol gradient provides 397 mg of 11β-fluoro-3-hydroxy-7α-{5-[methyl-(4,4,5,5,5-pentafluoro-pentyl)-amino]-pentyl}-estra-1,3,5(10)-trien-17-one.

b) 11β-Fluoro-7α-{5-[methyl-(4,4,5,5,5-pentafluoro-pentyl)-amino]-pentyl}-estra-1,3,5(10)-triene-3,17β-diol 380 mg of 11β-fluoro-3-hydroxy-7α-{5-[methyl-(4,4,5,5,5-pentafluoro-pentyl)-amino]-pentyl}-estra-1,3,5(10)-trien-17-one is dissolved in 25 ml of methanol and mixed with 77 mg of sodium borohydride. After 30 minutes of stirring at room temperature, the batch is added to saturated common salt solution, extracted with methylene chloride, dried on magnesium sulfate and concentrated by evaporation in a vacuum. After the crude product is chromatographed on silica gel with a methylene chloride-methanol gradient, 317 mg of 11β-fluoro-7α-{5-[methyl-(4,4,5,5,5-pentafluoro-pentyl)-amino]-pentyl}-estra-1,3,5(10)-triene-3,17β-diol is obtained as a foam, $[\alpha]_D=+49°$ (c=0.5 in methanol).

Example 9

11β-Fluoro-7α-{5-[methyl-(4,4,5,5,6,6,7,7,8,8,9,9,9-tridecafluoro-nonyl)-amino]-pentyl}-estra-1,3,5(10)-triene-3,17β-diol A solution of 466 mg of 7α-(5-bromopentyl)-11β-fluor-estra-1,3,5(10)-triene-3,17-diol in 10 ml of 1-methyl-2-pyrrolidinone is stirred with 1.17 g of methyl-(4,4,5,5,6,6,7,7,8,8,9,9,9-tridecafluorononyl)-amine for 3 hours at a bath temperature of 80° C. For working-up, the batch is added to saturated sodium chloride solution, extracted with ethyl acetate, dried on sodium sulfate, concentrated by evaporation in a vacuum and chromatographed on silica gel with dichloromethane/methanol. 625 mg of 11β-fluor-7α-{5-[methyl-(4,4,5,5,6,6,7,7,8,8,9,9,9-tridecafluoro-nonyl)-amino]-pentyl}-estra-1,3,5(10)-triene-3,17β-diol is obtained as a foam, $[\alpha]_D=+35°$ (c=0.5 in CHCl$_3$).

Example 10

11β-Fluoro-7α-{5-[(4,4,5,5,6,6,7,7,8,8,9,9,10,10,11,11,11-heptadecafluor-undecyl)-methyl-amino]-pentyl}-estra-1,3,5(10)-triene-3,17β-diol A solution of 466 mg of 7α-(5-bromopentyl)-11β-fluor-estra-1,3,5(10)-triene-3,17-diol in 10 ml of 1-methyl-2-pyrrolidinone is stirred with 1.47 g of (4,4,5,5,6,6,7,7,8,8,9,9,10,10,11,11,11-heptadecafluor-undecyl)-methyl-amine for 3 hours at a bath temperature of 80° C. For working-up, the batch is added to saturated sodium chloride solution, extracted with ether, dried on sodium sulfate, concentrated by evaporation in a vacuum and chromatographed on silica gel with ethyl acetate/methanol. 524 mg of 11β-fluoro-7α-{5-[(4,4,5,5,6,6,7,7,8,8,9,9,10,10,11,11,11-heptadecafluor-undecyl)-methyl-amino]-pentyl}-estra-1,3,5(10)-triene-3,17β-diol is obtained as a foam, $[\alpha]_D=+24°$ (c=0.5 in CHCl$_3$).

Example 11

11β-Fluoro-7α-{5-[methyl-(3,3,4,4,5,5,6,6,6-nonafluoro-hexyl)-amino]-pentyl}-estra-1,3,5(10)-triene-3,17β-diol a) 11β-Fluoro-3-hydroxy-7α-{5-[methyl-(3,3,4,4,5,5,6,6,6-nonafluoro-hexyl)-amino]-pentyl}-estra-1,3,5(10)-trien-17-one 276 mg of 11β-fluoro-3-hydroxy-7α-(5-(methyl-amino)-pentyl)-estra-1,3,5(10)-trien-17-one is dissolved in 3 ml of N-methylpyrrolidone, mixed with 0.6 ml of 1,1,1,2,2,3,3,4,4-nonafluor-5-iodo-hexane and heated for 1.5 hours at a bath temperature of 80° C. For working-up, the reaction mixture is cooled to room temperature, stirred into saturated common salt solution, extracted with ethyl acetate, the organic phases are washed with water, dried on magnesium sulfate and concentrated by evaporation in a vacuum. Preparative column chromatography on silica gel with a methylene chloride-methanol gradient provides 176 mg of 11β-fluoro-3-hydroxy-7α-{5-[methyl-(3,3,4,4,5,5,6,6,6-nonafluoro-hexyl)-amino]-pentyl}-estra-1,3,5(10)-trien-17-one.

b) 11β-Fluoro-7α-{5-[methyl-(3,3,4,4,5,5,6,6,6-nonafluoro-hexyl)-amino]-pentyl}-estra-1,3,5(10)-triene-3,17β-diol 160 mg of 11β-fluoro-3-hydroxy-7α-{5-[methyl-(3,3,4,4,5,5,6,6,6-nonafluoro-hexyl)-amino]-pentyl}-estra-1,3,5(10)-trien-17-one is dissolved in 5 ml of methanol and mixed with 28 mg of sodium borohydride. After 30 minutes of stirring at room temperature, the batch is added to saturated common salt solution, extracted with methylene chloride, dried on magnesium sulfate and concentrated by evaporation in a vacuum. After the crude product is chromatographed on silica gel with a methylene chloride-MTBE gradient and an ethyl acetate-acetone gradient, 105 mg of 11β-fluoro-7α-{5-[methyl-(3,3,4,4,5,5,6,6,6-nonafluoro-hexyl)-amino]-pentyl}-estra-1,3,5(10)-triene-3,17β-diol is obtained as a foam, $[\alpha]_D=+43°$ (c=0.5 in CHCl$_3$).

Example 12

11β-Fluoro-7α-{5-[methyl-(7,7,8,8,8-pentafluor-octyl)-amino]-pentyl}-estra-1,3,5(10)-triene-3,17β-diol A solution of 466 mg of 7α-(5-bromopentyl)-11β-fluor-estra-1,3,5(10)-triene-3,17-diol in 10 ml of 1-methyl-2-pyrrolidinone is stirred with 702 mg of methyl-(7,7,8,8,8-pentafluor-octyl)-amine for 3 hours at a bath temperature of 80° C. For working-up, the batch is added to saturated sodium chloride solution, extracted with ethyl acetate, dried on sodium sulfate, concentrated by evaporation in a vacuum and chromatographed on silica gel with dichloromethane/methanol. 595 mg of 11β-fluoro-7α-{5-[methyl-(7,7,8,8,8-pentafluor-octyl)-amino]-pentyl}-estra-1,3,5(10)-triene-3,17β-diol is obtained as a foam, $[\alpha]_D=+39°$ (c=0.5 in CHCl$_3$).

Example 13

11β-Fluoro-7α-{6-[methyl-(7,7,8,8,8-pentafluor-octyl)-amino]-hexyl}-estra-1,3,5(10)-triene-3,17α-diol a) 7α-(6-Chlorohexyl)-11β-fluor-estra-1,3,5(10)-triene-3,17-diol 611 mg of 7α-(6-chlorohexyl)-11β-fluor-3-hydroxy-estra-1,3,5(10)-trien-17-one is dissolved in 10 ml of methanol and carefully mixed with 166 mg of sodium borohydride. After 15 minutes of stirring at room temperature, the batch is added to saturated common salt solution, extracted with methylene chloride, dried on magnesium sulfate and concentrated by evaporation in a vacuum. 599 mg of 7α-(6-chlorohexyl)-11β-fluor-estra-1,3,5(10)-triene-3,17-diol is obtained as a crude product, which is used without further purification in the next stage.

b) 11β-Fluor-7α-(6-iodohexyl)-estra-1,3,5(10)-triene-3,17-diol 599 mg of 7α-(6-chlorohexyl)-11β-fluor-estra-1,3,5(10)-triene-3,17-diol is dissolved in 10 ml of ethylmethylketone, mixed with 675 mg of sodium iodide and stirred overnight at a bath temperature of 90° C. For working-up, the reaction mixture is cooled to room temperature, taken up in ethyl acetate, extracted once with 10% sodium thiosulfate solution, washed with common salt solution, dried on magnesium sulfate and concentrated by evaporation in a vacuum. 691 mg of 11β-fluor-7α-(6-iodohexyl)-estra-1,3,5 (10)-triene-3,17-diol is obtained as a crude product, which is used without further purification in the next stage.

c) 11β-Fluoro-7α-{6-[methyl-(7,7,8,8,8-pentafluor-octyl)-amino]-hexyl}-estra-1,3,5(10)-triene-3,17β-diol A solution of 690 mg of 11β-fluor-7α-(6-iodohexyl)-estra-1,3,5(10)-triene-3,17-diol in 15 ml of 1-methyl-2-pyrrolidinone is stirred with 810 mg of methyl-(7,7,8,8,8-pentafluor-octyl)-amine for 3 hours at a bath temperature of 80° C. For working-up, the batch is added to saturated sodium chloride solution, extracted with ether, dried on sodium sulfate, concentrated by evaporation in a vacuum and chromatographed on silica gel with dichloromethane/methanol/ammonia (25%). 576 mg of 11β-fluoro-7α-{6-[methyl-(7,7,8,8,8-pentafluor-octyl)-amino]-hexyl}-estra-1, 3,5(10)-triene-3,17β-diol is obtained as a foam, $[\alpha]_D=+42°$ (c=0.5 in CHCl$_3$).

Example 14

11β-Fluoro-7α-{5-(methyl-(7,7,8,8,9,9,10,10,10-nonafluoro-decyl)-amino]-pentyl}-estra-1,3,5(10)-triene-3,17β-diol A solution of 466 mg of 7α-(5-bromopentyl)-11β-fluor-estra-1,3,5(10)-triene-3,17-diol in 10 ml of 1-methyl-2-pyrrolidinone is stirred with 1.0 g of methyl-(7,7,8,8,8,9,9,10,10,10-nonafluoro-decyl)-amine for 3 hours at a bath temperature of 80° C. For working-up, the batch is added to saturated sodium chloride solution, extracted with ether, dried on sodium sulfate, concentrated by evaporation in a vacuum and chromatographed on silica gel with ethyl acetate/methanol. 546 mg of 11β-fluoro-7α-{5-[methyl-(7,7,8,8,8,9,9,10,10,10-nonafluoro-decyl)-amino]-pentyl}-estra-1,3,5(10)-triene-3,17β-diol is obtained as a foam, $[\alpha]_D=+39°$ (c=0.5 in CHCl$_3$).

Example 15

11β-Fluoro-7α-{5-[methyl-(7,7,8,8,9,9,10,10,11,11,12,12,12-tridecafluoro-dodecyl)-amino]-pentyl}-estra-1,3,5(10)-triene-3,17β-diol A solution of 466 mg of 7α-(5-bromopentyl)-11β-fluor-estra-1,3,5(10)-triene-3,17-diol in 10 ml of 1-methyl-2-pyrrolidinone is stirred with 1.3 g of methyl-(7,7,8,8,8,9,9,10,10,11,11,12,12,12-tridecafluoro-dodecyl)-amine for 3 hours at a bath temperature of 80° C. For working-up, the batch is added to saturated sodium chloride solution, extracted with ether, dried on sodium sulfate, concentrated by evaporation in a vacuum and chromatographed on silica gel with ethyl acetate/methanol. 628 mg of 11β-fluoro-7α-{5-[methyl-(7,7,8,8,8,9,9,10,10,11,11,12,12,12-tridecafluoro-dodecyl)-amino]-pentyl}-estra-1,3,5(10)-triene-3,17β-diol is obtained as a foam, $[\alpha]_D=+24°$ (c=0.5 in CHCl$_3$).

Example 16

11β-Fluoro-7α-{5-[(7,7,8,8,9,9,10,10,11,11,12,12,13,13,14,14,14-heptadecafluoro-tetradecyl)-methyl-amino]-pentyl}-estra-1,3,5(10)-triene-3,17β-diol A solution of 431 mg of 7α-(5-bromopentyl)-11β-fluor-estra-1,3,5(10)-triene-3,17-diol in 10 ml of 1-methyl-2-pyrrolidinone is stirred with 1.6 g of (7,7,8,8,8,9,9,10,10,11,11,12,12,13,13,14,14,14-heptadecafluoro-tetradecyl)-methyl-amine for 3 hours at a bath temperature of 80° C. For working-up, the batch is added to saturated sodium chloride solution, extracted with ether, dried on sodium sulfate, concentrated by evaporation in a vacuum and chromatographed on silica gel with ethyl acetate/methanol. 318 mg of 11β-fluoro-7α-{5-[(7,7,8,8,8,9,9,10,10,11,11,12,12,13,13,14,14,14-heptadecylfluoro-tetradecyl)-methyl-amino]-pentyl}-estra-1,3,5(10)-triene-3,17β-diol is obtained as a foam, $[\alpha]_D=+23°$ (c=0.5 in CHCl$_3$).

Example 17

11β-Fluoro-7α-{5-[(3,4,4,5,5,5-hexafluoro-pent-2-enyl)-methyl-amino]-pentyl}-estra-1,3,5(10)-triene-3,17β-diol a) 11β-Fluoro-7α-{5-[(3,4,4,5,5,5-hexafluoro-pent-2-enyl)-methyl-amino]-pentyl}-3-hydroxy-estra-1,3,5(10)-trien-17-one 880 mg of 11β-fluoro-3-hydroxy-7α-(5-iodopentyl)-estra-1,3,5(10)-trien-17-one and 1.26 g of (3,4,4,5,5,5-hexafluoro-pent-2-enyl)-methyl-amine are dissolved in 20 ml of N-methylpyrrolidone and stirred for 3 hours at a bath temperature of 80° C. After the reaction solution is cooled to room temperature, the batch is added to saturated common salt solution, extracted with diethyl ether, dried and concentrated by evaporation in a vacuum. 1.86 g of 11β-fluoro-7α-{5-[(3,4,4,5,5,5-hexafluoro-pent-2-enyl)-methyl-amino]-pentyl}-3-hydroxy-estra-1,3,5(10)-trien-17-one is obtained as a crude product, which is used without purification in the next stage.

b) 11β-Fluoro-7α-{5-[(3,4,4,5,5,5-hexafluoro-pent-2-enyl)-methyl-amino]-pentyl}-estra-1,3,5(10)-triene-3,17β-diol 1.86 g of 11β-fluoro-7α-{5-[(3,4,4,5,5,5-hexafluoro-pent-2-enyl)-methyl-amino]-pentyl}-3-hydroxy-estra-1,3,5 (10)-trien-17-one is dissolved in 15 ml of methanol and carefully mixed with 222 mg of sodium borohydride. After 15 minutes of stirring at room temperature, the batch is added to saturated common salt solution, extracted with methylene chloride, dried on magnesium sulfate and concentrated by evaporation in a vacuum. After the crude product is chromatographed on silica gel with a hexane-ethyl acetate gradient and an ethyl acetate-acetone gradient, 241 mg of 11β-fluoro-7α-{5-[(3,4,4,5,5,5-hexafluoro-pent-2-enyl)-methyl-amino]-pentyl}-estra-1,3,5(10)-triene-3,17β-diol with a melting point of 122° C. is obtained, $[\alpha]_D=+47°$ (c=0.5 in CHCl$_3$).

Example 18

11β-Fluoro-7α-{5-[methyl-(3,4,4,5,5,6,6,6-octafluoro-hex-2-enyl)-amino]-pentyl}-estra-1,3,5 (10)-triene-3,17β-diol a) 11β-Fluoro-3-hydroxy-7α-{5-[methyl-(3,4,4,5,5,6,6,6-octafluoro-hex-2-enyl)-amino]-pentyl}-estra-1,3,5(10)-trien-17-one 880 mg of 11β-fluoro-3-hydroxy-7α-(5-iodopentyl)-estra-1,3,5(10)-trien-17-one and 2.21 g of methyl-(3,4,4,5,5,6,6,6-octafluoro-hex-2-enyl)-amine are dissolved in 20 ml of N-methylpyrrolidone and stirred for 1 hour at a bath temperature of 80° C. After the reaction solution is cooled to room temperature, the batch is added to saturated common salt solution, extracted with diethyl ether, dried and concentrated by evaporation in a vacuum. 1.69 g of 11β-fluoro-3-hydroxy-7α-{5-[methyl-(3,4,4,5,5,6,6,6-octafluoro-hex-2-enyl)-amino]-pentyl}-estra-1,3,5(10)-trien-17-one is obtained as a crude product, which is used without purification in the next stage.

b) 11β-Fluoro-7α-{5[-methyl-(3,4,4,5,5,6,6,6-octafluoro-hex-2-enyl)-amino]-pentyl}-estra-1,3,5(10)-triene-3,17β-diol 1.7 g of 11β-fluoro-3-hydroxy-7α-{5-[methyl-(3,4,4,5,5,6,6,6-octafluoro-hex-2-enyl)-amino]-pentyl}-estra-1,3,5(10)-trien-17-one is dissolved in 15 ml of methanol and carefully mixed with 222 mg of sodium borohydride. After 15 minutes of stirring at room temperature, the batch is added to saturated common salt solution, extracted with methylene chloride, dried on magnesium sulfate and concentrated by evaporation in a vacuum. After the crude product is chromatographed on silica gel with ethyl acetate as an eluent, 84 mg of 11β-fluoro-7α-{5-[methyl-(3,4,4,5,5,6,6,6-octafluoro-hex-2-enyl)-amino]-pentyl}-estra-1,3,5(10)-triene-3,17β-diol with a melting point of 130° C. is obtained.

Example 19

7α-{5-[(3,4,4,5,5,6,6,7,7,8,8,8-Dodecafluor-oct-2-enyl)-methyl-amino]-pentyl}-11β-fluor-estra-1,3,5(10)-triene-3,17β-diol a) 7α-{5-[(3,4,4,5,5,6,6,7,7,8,8,8-Dodecafluor-oct-2-enyl)-methyl-amino]-pentyl}-11β-fluoro-3-hydroxy-estra-1,3,5(10)-trien-17-one 880 mg of 11β-fluoro-3-hydroxy-7α-(5-iodopentyl)-estra-1,3,5(10)-trien-17-one and 2.23 g of (3,4,4,5,5,6,6,7,7,8,8,8-dodecafluor-oct-2-enyl)-methyl-amine are dissolved in 20 ml of N-methylpyrrolidone and stirred for 1 hour at a bath temperature of 80° C. After the reaction solution is cooled to room temperature, the batch is added to saturated common salt solution, extracted with diethyl ether, dried and concentrated by evaporation in a vacuum. 2.47 g of 7α-{5-[(3,4,4,5,5,6,6,7,7,8,8,8-dodecafluor-oct-2-enyl)-methyl-amino]-pentyl}-11β-fluoro-3-hydroxy-estra-1,3,5(10)-trien-17-one is obtained as a crude product, which is used without purification in the next stage.

b) 7α-{5-[(3,4,4,5,5,6,6,7,7,8,8,8-Dodecafluor-oct-2-enyl)-methyl-amino]-pentyl}-11β-fluor-estra-1,3,5(10)-triene-3,17β-diol 2.4 g of 7α-{5-[(3,4,4,5,5,6,6,7,7,8,8,8-dodecafluor-oct-2-enyl)-methyl-amino]-pentyl}-11β-fluoro-3-hydroxy-estra-1,3,5(10)-trien-17-one is dissolved in 15 ml of methanol and carefully mixed with 222 mg of sodium borohydride. After 15 minutes of stirring at room temperature, the batch is added to saturated common salt solution, extracted with methylene chloride, dried on magnesium sulfate and concentrated by evaporation in a vacuum. After the crude product is chromatographed on silica gel with ethyl acetate as an eluent, 319 mg of 7α-{5-[(3,4,4,5,5,6,6,7,7,8,8,8-dodecafluor-oct-2-enyl)-methyl-amino]-pentyl}-11β-fluor-estra-1,3,5(10)-triene-3,17β-diol is obtained as a foam, $[\alpha]_D=+37°$ (c=0.5 in $CHCl_3$).

Example 20

11β-Fluoro-7α-{5-[(3,4,4,5,5,6,6,7,7,8,8,9,9,10,10,10-hexadecafluoro-dec-2-enyl)-methyl-amino]-pentyl}-estra-1,3,5(10)-triene-3,17β-diol a) 11β-Fluoro-7α-{5-[(3,4,4,5,5,6,6,7,7,8,8,9,9,10,10,10-hexadecafluoro-dec-2-enyl)-methyl-amino]-pentyl}-3-hydroxy-estra-1,3,5(10)-trien-17-one 880 mg of 11β-fluoro-3-hydroxy-7α-(5-iodopentyl)-estra-1,3,5(10)-trien-17-one and 1.83 g of (3,4,4,5,5,6,6,7,7,8,8,9,9,10,10,10-hexadecafluoro-dec-2-enyl)-methyl-amine are dissolved in 20 ml of N-methylpyrrolidone and stirred for 1 hour at a bath temperature of 80° C. After the reaction solution is cooled to room temperature, the batch is added to saturated common salt solution, extracted with diethyl ether, dried and concentrated by evaporation in a vacuum. After the crude product is chromatographed on silica gel with ethyl acetate as an eluent, 1.2 g of 11β-fluoro-7α-{5-[(3,4,4,5,5,6,6,7,7,8,8,9,9,10,10,10-hexadecafluoro-dec-2-enyl)-methyl-amino]-pentyl}-3-hydroxy-estra-1,3,5(10)-trien-17-one is obtained.

b) 11β-Fluoro-7α-{5-[(3,4,4,5,5,6,6,7,7,8,8,9,9,10,10,10-hexadecafluoro-dec-2-enyl)-methyl-amino]-pentyl}-estra-1,3,5(10)-triene-3,17β-diol 1.1 g of 11β-fluoro-7α-{5-[(3,4,4,5,5,6,6,7,7,8,8,9,9,10,10,10-hexadecafluoro-dec-2-enyl)-methyl-amino]-pentyl}-3-hydroxy-estra-1,3,5(10)-trien-17-one is dissolved in 10 ml of methanol and carefully mixed with 148 mg of sodium borohydride. After 15 minutes of stirring at room temperature, the batch is added to saturated common salt solution, extracted with methylene chloride, dried on magnesium sulfate and concentrated by evaporation in a vacuum. After the crude product is chromatographed on silica gel with a hexane-ethyl acetate gradient and an ethyl acetate-acetone gradient, 127 mg of 11β-fluoro-7α-{5-[(3,4,4,5,5,6,6,7,7,8,8,9,9,10,10,10-hexadecafluoro-dec-2-enyl)-methyl-amino]-pentyl}-estra-1,3,5(10)-triene-3,17-diol is obtained as a foam, $[\alpha]_D=+35°$ (c=0.5 in $CHCl_3$).

Production of the Starting Compounds (3,4,4,5,5,5-Hexafluoro-pent-2-enyl)-methyl-amine 3.55 g of methylamine is condensed in a solution of 2.6 ml of 1,1,1,2,2,3,3 heptafluor-5-iodo-pentane in 20 ml of anhydrous tetrahydrofuran at −40° C., and it is stirred overnight at room temperature in a pressurized reactor. After the pressurized reactor was opened at −30° C., it is allowed to come to room temperature to allow excess methylamine to evaporate off. Then, the reaction solution is mixed with diethyl ether, washed with saturated common salt solution, dried on magnesium sulfate and concentrated by evaporation in a vacuum. 1.26 g of (3,4,4,5,5,5-hexafluoro-pent-2-enyl)-methyl-amine is obtained as a crude product.

Methyl-(3,4,4,5,5,6,6,6-octafluoro-hex-2-enyl)-amine 2.36 g of methylamine is condensed in a solution of 2.96 ml of 1,1,1,2,2,3,3,4,4 nonafluor-6-iodo-hexane in 20 ml of anhydrous tetrahydrofuran at −40° C., and it is stirred overnight at room temperature in a pressurized reactor. After the pressurized reactor was opened at −30° C., it is allowed to come to room temperature to allow excess methylamine to evaporate off.

Then, the reaction solution is mixed with diethyl ether, washed with saturated common salt solution, dried on magnesium sulfate and concentrated by evaporation in a vacuum. 2.21 g of methyl-(3,4,4,5,5,6,6,6-octafluoro-hex-2-enyl)-amine is obtained as a crude product.

(3,4,4,5,5,6,6,7,7,8,8,8-Dodecafluor-oct-2-enyl)-methyl-amine 2.44 g of methylamine is condensed in a solution of 2.82 ml of 1,1,1,2,2,3,3,4,4,5,5,6,6 tridecafluor-8-iod-octane in 20 ml of anhydrous tetrahydrofuran at −40° C., and it is stirred overnight at room temperature in a pressurized reactor. After the pressurized reactor was opened at −30° C., it is allowed to come to room temperature to allow excess methylamine to evaporate off. Then, the reaction solution is mixed with diethyl ether, washed with saturated common salt solution, dried on magnesium sulfate and concentrated by evaporation in a vacuum. 2.23 g of (3,4,4,5,5,6,6,7,7,8,8,8-dodecafluor-oct-2-enyl)-methyl-amine is obtained as a crude product.

(3,4,4,5,5,6,6,7,7,8,8,9,9,10,10,10-Hexadecafluoro-dec-2-enyl)-methyl-amine 3.84 g of methylamine is condensed in a solution of 2.86 g of 1,1,1,2,2,3,3,4,4,5,5,6,.6,7,7,8,8 heptadecafluor-10-iodo-decane in 20 ml of anhydrous tetrahydrofuran at −40° C., and it is stirred overnight at room temperature in a pressurized reactor. After the pressurized reactor was opened at −30° C., it is allowed to come to room temperature to allow excess methylamine to evaporate off. Then, the reaction solution is mixed with diethyl ether, washed with saturated common salt solution, dried on magnesium sulfate and concentrated by evaporation in a vacuum. 1.83 g of (3,4,4,5,5,6,6,7,7,8,8,9,9,10,10,10-hexadecafluoro-dec-2-enyl)-methyl-amine is obtained as a crude product.

Methyl-(4,4,5,5,6,6,7,7,8,8,9,9,9-tridecafluoro-nonyl)-amine a) 4,4,5,5,6,6,7,7,8,8,9,9,9-Tridecafluoro-nonyltosylate 2.33 ml of 4,4,5,5,6,6,7,7,8,8,9,9,9-tridecafluoro-nonan-1-ol is dissolved in 20 ml of absolute pyridine, mixed at 0° C. with 2.48 g of p-toluenesulfonyl chloride and stirred for 3 hours under cold conditions. Then, the reaction mixture is stirred into water, extracted with dichloromethane, dried on magnesium sulfate and concentrated by evaporation in a vacuum. Column-chromatographic purification on silica gel with a hexane-ethyl acetate gradient yields 3.86 g of 4,4,5,5,6,6,7,7,8,8,9,9,9-tridecafluoro-nonyltosylate as a clear oil.

b) Methyl-(4,4,5,5,6,6,7,7,8,8,9,9,9-tridecafluoro-nonyl)-amine 4.44 g of methylamine is condensed in a solution of 3.86 g of 4,4,5,5,6,6,7,7,8,8,9,9,9-tridecafluoro-nonyltosylate in 10 ml of absolute tetrahydrofuran at −20° C., and it is stirred in a pressure vessel at room temperature. After the pressure vessel was opened at −20° C., it is allowed to come to room temperature to allow excess methylamine to evaporate off. The reaction solution is taken up in dichloromethane, washed with water, dried on magnesium sulfate and concentrated by evaporation in a vacuum. 2.38 g of methyl-(4,4,5,5,6,6,7,7,8,8,9,9,9-tridecafluoro-nonyl)-amine is obtained as a crude product.

(4,4,5,5,6,6,7,7,8,6,9,9,10,10,11,11,11-Heptadecafluor-undecyl)-methyl-amine a) 4,4,5,5,6,6,7,7,8,8,9,9,10,10,11,11,11-Heptadecafluor-undecyltosylate 4.78 g of 4,4,5,5,6,6,7,7,8,8,9,9,10,10,11,11,11-heptadecafluor-undecan-1-ol is dissolved in 20 ml of absolute pyridine, mixed at 0° C. with 2.48 g of p-toluenesulfonyl chloride and stirred for 3 hours under cold conditions. Then, the reaction mixture is stirred into water, extracted with dichloromethane, dried on magnesium sulfate and concentrated by evaporation in a vacuum. Column-chromatographic purification on silica gel with a hexane-ethyl acetate gradient yields 4.3 g of 4,4,5,5,6,6,7,7,8,8,9,9,10,10,11,11,11-heptadecafluor-undecyltosylate as a clear oil.

b) (4,4,5,5,6,6,7,7,8,8,9,9,10,10,11,11,11-Heptadecafluor-undecyl)-methyl-amine 3.95 g of methylamine is condensed in a solution of 4.3 g of 4,4,5,5,6,6,7,7,8,8,9,9,10,10,11,11,11-heptadecafluor-undecyltosylate in 10 ml of absolute tetrahydrofuran at −20° C., and it is stirred overnight at room temperature. After the pressure vessel was opened at −20° C., it is allowed to come to room temperature to allow excess methylamine to evaporate off. The reaction solution is taken up in dichloromethane, washed with water, dried on magnesium sulfate and concentrated by evaporation in a vacuum. 3.1 g of (4,4,5,5,6,6,7,7,8,8,9,9,10,10,11,11,11-heptadecafluor-undecyl)-methyl-amine is obtained as a crude product.

Methyl-(7,7,8,8,8-pentafluor-octyl)-amine a) 7,7,8,8,8-Pentafluor-octyltosylate 1.6 ml of 7,7,8,8,8-pentafluor-octan-1-ol is dissolved in 20 ml of absolute pyridine, mixed at 0° C. with 2.48 g of p-toluenesulfonyl chloride and stirred for 3 hours under cold conditions. Then, the reaction mixture is stirred into water, extracted with dichloromethane, dried on magnesium sulfate and concentrated by evaporation in a vacuum. Column-chromatographic purification on silica gel with a hexane-ethyl acetate gradient yields 2.92 g of 7,7,8,8,8-pentafluor-octyltosylate as a clear oil.

b) Methyl-(7,7,8,8,8-pentafluor-octyl)-amine 4.0 g of methylamine is condensed in a solution of 2.9 g of 7,7,8,8,8-pentafluor-octyltosylate in 10 ml of absolute tetrahydrofuran at −20° C., and it is stirred overnight in a pressure vessel at room temperature. After the pressure vessel was opened at −20° C., it is allowed to come to room temperature to allow excess methylamine to evaporate off. The reaction solution is taken up in dichloromethane, washed with water, dried on magnesium sulfate and concentrated by evaporation in a vacuum. 1.58 g of methyl-(7,7,8,8,8-pentafluor-octyl)-amine is obtained as a crude product.

Methyl-(7,7,8,8,9,9,10,10,10-nonafluoro-decyl)-amine a) 7,7,8,8,9,9,10,10,10-Nonafluoro-decyltosylate 2.27 ml of 7,7,8,8,9,9,10,10,10-nonafluoro-decan-1-ol is dissolved in 20 ml of absolute pyridine, mixed at 0° C. with 2.48 g of p-toluenesulfonyl chloride and stirred for 3 hours under cold conditions. Then, the reaction mixture is stirred into water, extracted with dichloromethane, dried on magnesium sulfate and concentrated by evaporation in a vacuum. Column-chromatographic purification on silica gel with a hexane-ethyl acetate gradient yields 3.89 g of 7,7,8,8,9,9,10,10,10-nonafluoro-decyltosylate as a clear oil.

b) Methyl-(7,7,8,8,9,9,10,10,10-nonafluoro-decyl)-amine 4.12 g of methylamine is condensed in a solution of 3.89 g of 7,7,8,8,9,9,10,10,10-nonafluoro-decyltosylate in 10 ml of absolute tetrahydrofuran at −20° C., and it is stirred overnight in a pressure vessel at room temperature. After the pressure vessel was opened at −20° C., it is allowed to come to room temperature to allow excess methylamine to evaporate off. The reaction solution is taken up in dichloromethane, washed with water, dried on magnesium sulfate and concentrated by evaporation in a vacuum. 2.63 g of methyl-(7,7,8,8,9,9,10,10,10-nonafluoro-decyl)-amine is obtained as a crude product.

Methyl-(7,7,8,8,9,9,10,10,11,11,12,12,12-tridecafluoro-dodecyl)-amine a) 7,7,8,8,9,9,10,10,11,11,12,12,12-Tridecafluoro-dodecyltosylate 2.76 ml of 7,7,8,8,9,9,10,10,11,11,12,12,12-tridecafluoro-dodecan-1-ol is dissolved in 20 ml of absolute pyridine, mixed at 0° C. with 2.48 g of p-toluenesulfonyl chloride and stirred for 3 hours under cold conditions. Then, the reaction mixture is stirred into water, extracted with dichloromethane, dried on magnesium sulfate and concentrated by evaporation in a vacuum. Column-chromatographic purification on silica gel with a hexane-ethyl acetate gradient yields 4.33 g of 7,7,8,8,9,9,10,10,11,11,12,12,12-tridecafluoro-dodecyl tosylate as a clear oil.

b) Methyl-(7,7,8,8,9,9,10,10,11,11,12,12,12-tridecafluoro-dodecyl)-amine 3.23 g of methylamine is condensed in a solution of 4.33 g of 7,7,8,8,9,9,10,10,11,11,12,12,12-tridecafluoro-dodecyl tosylate in 10 ml of absolute tetrahydrofuran at −20° C., and it is stirred overnight in a pressure vessel at room temperature. After the pressure vessel was opened at −20° C., it is allowed to come to room temperature to allow excess methylamine to evaporate off. The reaction solution is taken up in dichloromethane, washed with water, dried on magnesium sulfate and concentrated by evaporation in a vacuum. 3.2 g of methyl-(7,7,8,8,9,9,10,10,11,11,12,12,12-tridecafluoro-dodecyl)-amine is obtained as a crude product.

(7,7,8,8,9,9,10,10,11,11,12,12,13,13,14,14,14-Heptadecafluoro-tetradecyl)-methyl-amine a) 7,7,8,8,9,9,10,10,11,11,12,12,13,13,14,14,14-Heptadecafluoro-tetradecyltosylate 5.2 g of 7,7,8,8,9,9,10,10,11,11,12,12,13,13,14,14,14-heptadecafluoro-tetradecan-1-ol is dissolved in 20 ml of absolute pyridine, mixed at 0° C. with 2.48 g of p-toluenesulfonyl chloride and stirred for 3 hours at room temperature. Then, the reaction mixture is stirred into water, extracted with dichloromethane, dried on magnesium sulfate and concentrated by evaporation in a vacuum. Column-chromatographic purification on silica gel with a hexane-ethyl acetate gradient yields 5.72 g of 7,7,8,8,9,9,10,10,11,11,12,12,13,13,14,14,14-heptadecafluoro-tetradecyltosylate as a clear oil.

b) (7,7,8,8,9,9,10,10,11,11,12,12,13,13,14,14,14-Heptadecafluoro-tetradecyl)-methyl-amine 3.78 g of methylamine is condensed in a solution of 5.72 g of 7,7,8,8,9,9,10,10,11,11,12,12,13,13,14,14,14-heptadecafluoro-tetradecyl-tosylate in 10 ml of absolute tetrahydrofuran at −20° C., and it is stirred overnight in a pressure vessel at room temperature. After the pressure vessel was opened at −20° C., it is allowed to come to room temperature to allow excess methylamine to evaporate off. The reaction solution is taken up in dichloromethane, washed with water, dried on magnesium sulfate and concentrated by evaporation in a vacuum. 4.29 g of (7,7,8,8,9,9,10,10,11,11,12,12,13,13,14,14,14-heptadecafluoro-tetradecyl)-methyl-amine is obtained as a crude product.

Example 21

11β-Fluoro-7α-{5-[methyl-(3-phenoxy-propyl)-amino]-pentyl}-estra-1,3,5(10)-triene-3,17β-diol a) 7α-(5-Chloropentyl)-11β-fluor-estra-1,3,5(10)-triene-3,17β-diol 5.0 g of 7α-(5-chloropentyl)-11β-fluoro-3-hydroxy-estra-1,3,5(10)-trien-17-one is dissolved in 100 ml of methanol and mixed in portions at 0° C. with 0.96 g of sodium borohydride. After 30 minutes of stirring at 0° C., the reaction mixture is added to semi-saturated sodium chloride solution, extracted 3 times with ethyl acetate and washed once with saturated common salt solution. After drying on magnesium sulfate, it is concentrated by evaporation in a vacuum. Preparative column chromatography on silica gel with a hexane-ethyl acetate gradient yields 4.29 g of 7α-(5-chloropentyl)-11β-fluor-estra-1,3,5(10)-triene-3,17β-diol.

b) 11β-Fluor-7α-(5-iodopentyl)-estra-1,3,5(10)-triene-3,17β-diol 4.29 g of 7α-(5-chloropentyl)-11β-fluor-estra-1,3,5(10)-triene-3,17β-diol is dissolved in 60 ml of ethylmethylketone, mixed with 4.91 g of sodium iodide and stirred overnight at 90° C. For working-up, the reaction mixture is cooled to room temperature, stirred into water, extracted 3 times with ethyl acetate, washed with thiosulfate solution, dried on magnesium sulfate and concentrated by evaporation in a vacuum. 5.16 g of 11β-fluor-7α-(5-iodopentyl)-estra-1,3,5(10)-triene-3,17β-diol is obtained as a crude product, which is used without further purification in the next stage.

c) 11β-Fluoro-7α-{5-[methyl-(3-phenoxy-propyl)-amino]-pentyl}-estra-1,3,5(10)-triene-3,17β-diol A solution of 486 mg of 11β-fluor-7α-(5-iodopentyl)-estra-1,3,5(10)-triene-3,17β-diol in 10 ml of 1-methyl-2-pyrrolidinone is stirred with 600 mg of methyl-(3-phenoxy-propyl)-amine for 3 hours at a bath temperature of 80° C. Then, the batch is added to saturated sodium chloride solution, extracted with ether, dried on sodium sulfate, concentrated by evaporation in a vacuum and chromatographed on silica gel with methylene chloride/methanol/ammonia. 443 mg of 11β-fluoro-7α-{5-[methyl-(3-phenoxy-propyl)-amino]-pentyl}-estra-1,3,5(10)-triene-3,17β-diol is obtained as a foam $[\alpha]_D=+47°$ (c=0.5 in $CHCl_3$).

Example 22

7α-{5-[(3-Benzyloxy-propyl)-methyl-amino]-pentyl}-11β-fluor-estra-1,3,5(10)-triene-3,17β-diol A solution of 486 mg of 11β-fluor-7α-(5-iodopentyl)-estra-1,3,5(10)-triene-3,17β-diol in 10 ml of 1-methyl-2-pyrrolidinone is stirred with 540 mg of (3-benzyloxy-propyl)-methyl-amine for 3 hours at a bath temperature of 80° C. Then, the batch is added to saturated sodium chloride solution, extracted with ether, dried on sodium sulfate, concentrated by evaporation in a vacuum and chromatographed on silica gel with methylene chloride/methanol/ammonia. 237 mg of 7α-{5-[(3-benzyloxy-propyl)-methyl-amino]-pentyl}-11β-fluor-estra-1,3,5(10)-triene-3,17β-diol is obtained as a foam $[\alpha]_D=+48°$ (c=0.5 in $CHCl_3$).

Production of the Starting Compounds

Methyl-(3-phenoxy-propyl)-amine 3.57 g of methylamine is condensed in a solution of 1.6 ml of 3-phenoxy-propylbromide in 15 ml of anhydrous tetrahydrofuran at −78° C., and it is stirred overnight at room temperature in a pressurized reactor. After the pressurized reactor was opened at −20° C., it is allowed to come to room temperature to allow excess methylamine to evaporate off. Then, the reaction solution is added to saturated sodium chloride solution, extracted with ether, dried on magnesium sulfate and concentrated by evaporation in a vacuum. 2.01 g of methyl-(3-phenoxy-propyl)-amine is obtained as a crude product, which is used without further purification in the next stage.

(3-Benzyloxy-propyl)-methyl-amine 3.57 g of methylamine is condensed in a solution of 1.8 ml of (3-bromo-propoxymethyl)-benzene in 15 ml of anhydrous tetrahydrofuran at −78° C., and it is stirred overnight at room temperature in a pressurized reactor. After the pressurized reactor was opened at −20° C., it is allowed to come to room temperature to allow excess methylamine to evaporate off. Then, the reaction solution is added to saturated sodium chloride solution, extracted with ether, dried on magnesium sulfate and concentrated by evaporation in a vacuum. 1.91 g of (3-benzyloxy-propyl)-methyl-amine is obtained as a crude product, which is used without further purification in the next stage.

Example 23

11β-Fluoro-7α-{5-[N-methyl-N-3-(4,4,5,5,5-pentafluoropentyloxy)-propylamino]-pentyl}-estra-1,3,5(10)-triene-3,17β-diol a) 11β-Fluoro-7α-(5-bromopentyl)-3-(tetrahydropyran-2-yloxy)-estra-1,3,5(10)-trien-17-one 8.4 g of 11β-fluoro-7α-(5-bromopentyl)-3-hydroxy-estra-1,3,5(10)-trien-17-one in 90 ml of tetrahydrofuran is allowed to react with 9.0 ml of 3,4-dihydropyran and 805 mg of p-toluenesulfonic acid hydrate at room temperature. After 7 hours, 1 ml of triethylamine is added, diluted with ethyl acetate, washed neutral with saturated sodium chloride solution and dried on sodium sulfate. The chromatography on silica gel with a hexane-ethyl acetate gradient yields 7.6 g of 11β-fluoro-7α-(5-bromopentyl)-3-(tetrahydropyran-2-yloxy)-estra-1,3,5(10)-trien-17-one as a foam.

b) 11-β-Fluoro-7α-{5-[(3-tert-butyl-dimethylsilyloxypropyl)-methylamino]-pentyl}-3-(tetrahydropyran-2-yloxy)-estra-1,3,5(10)-trien-17-one 6.0 g of 11β-fluoro-7α-(5-bromopentyl)-3-(tetrahydropyran-2-yloxy)-estra-1,3,5(10)-trien-17-one in 130 ml of dimethylformamide is reacted at 100° C. with 5.7 g of 1-N-methylamino-3-tert-butyl-dimethylsilyloxypropane (produced from 1-bromo-3-hydroxypropane by reaction with tert-butyl-dimethylsilyl chloride to form 1-bromo-3-tert-butyl-dimethylsilyloxypropane and subsequent reaction with methylamine). After 7 hours, it is diluted with ethyl acetate, washed with saturated sodium chloride solution and concentrated by evaporation in a vacuum. After the crude product is chromatographed on silica gel with a methylene chloride-methanol gradient, 4.5 g of 11-β-fluoro-7α-{5-[(3-tert-butyl-dimethylsilyloxypropyl)-methylamino]-pentyl}-3-(tetrahydropyran-2-yloxy)-estra-1,3,5(10)-trien-17-one is obtained as an oil.

c) 11β-Fluoro-7α-{5-[(3-hydroxypropyl)-methylamino]-pentyl}-estra-1,3,5(10)-trien-17-one 2.3 g of 11-β-fluoro-7α-{5-[(3-tert-butyl-dimethylsilyloxypropyl)-methylamino]-pentyl}-3-(tetrahydropyran-2-yloxy)-estra-1,3,5(10)-trien-17-one in 23 ml of tetrahydrofuran is reacted at room temperature with 6 ml of tetrabutylammonium fluoride solution (1M in tetrahydrofuran). After 2 hours, it is diluted with ethyl acetate, washed with saturated sodium chloride solution, dried and concentrated by evaporation in a vacuum. The chromatography of the crude product on silica gel with a methylene chloride-methanol gradient yields 1.5 g of 11β-fluoro-7α-{5-[(3-hydroxypropyl)-methylamino]-pentyl}-estra-1,3,5(10)-trien-17-one as a foam.

d) 11β-Fluoro-3-(tetrahydropyran-2-yloxy)-7α-{5-[N-methyl-N-3-(4,4,5,5,5-pentafluoropentyl-oxy)-propylamino]-pentyl}-estra-1,3,5(10)-trien-17-one 1.8 g of pentafluoropentyliodide, 10 ml of 40% sodium hydroxide solution and 465 mg of tetrabutylammonium hydrogen sulfate are added to 710 mg of 11β-fluoro-7α-{5-[(3-hydroxypropyl)-methylamino]-pentyl}-estra-1,3,5(10)-trien-17-one in 10 ml of toluene at room temperature. After 6 days, the reaction mixture is added to ice/water, extracted with ethyl acetate, washed with saturated sodium chloride solution, dried and concentrated by evaporation in a vacuum. After the crude product is chromatographed on silica gel with a methylene chloride-methanol gradient, 123 mg of 11β-fluoro-3-(tetrahydropyran-2-yloxy)-7α-{5-[N-methyl-N-3-(4,4,5,5,5-pentafluoropentyloxy)-propylamino]-pentyl}-estra-1,3,5(10)-trien-17-one is obtained as an oil.

e) 11β-Fluoro-3-(tetrahydropyran-2-yloxy)-7α-{5-[N-methyl-N-3-(4,4,5,5,5-pentafluoropentyl-oxy)-propylamino]-pentyl}-estra-1,3,5(10)-trien-17β-ol 120 mg of 11β-fluoro-3-(tetrahydropyran-2-yloxy)-7α-{5-[N-methyl-N-3-(4,4,5,5,5-pentafluoropentyloxy)-propylamino]-pentyl}-estra-1,3,5(10)-trien-17-one is reduced at room temperature to a mixture of 1 ml of tetrahydrofuran, 0.6 ml of ethanol, and 0.3 ml of water with 20 mg of sodium borohydride. After 1 hour, it is diluted with ethyl acetate, washed neutral with water, concentrated by evaporation in a vacuum and dried. 76 mg of 11β-fluoro-3-(tetrahydropyran-2-yloxy)-7α-{5-[N-methyl-N-3-(4,4,5,5,5-pentafluoropentyloxy)-propylamino]-pentyl}-estra-1,3,5(10)-trien-17β-ol is obtained as a crude product.

f) 11β-Fluoro-7α-{5-[N-methyl-N-3-(4,4,5,5,5-pentafluoropentyloxy)-propylamino]-pentyl}-estra-1,3,5(10)-triene-3,17β-diol 75 mg of 11β-fluoro-3-(tetrahydropyran-2-yloxy)-7α-{5-[N-methyl-N-3-(4,4,5,5,5-pentafluoropentyloxy)-propylamino]-pentyl}-estra-1,3,5(10)-trien-17β-ol is reacted in 1 ml of methanol and 0.1 ml of water with 50 mg of oxalic acid at room temperature. After 2 hours, it is diluted with methylene chloride, washed neutral with saturated sodium chloride solution, dried and concentrated by evaporation in a vacuum. After chromatography on silica gel with a methylene chloride-methanol gradient, the crude product yields 25 mg of 11β-fluoro-7α-{5-[N-methyl-N-3-(4,4,5,5,5-pentafluoropentyloxy)-propylamino]-pentyl}-estra-1,3,5(10)-triene-3,17β-diol as a foam.

Example 24

11β-Fluoro-7α-[9-(4,4,5,5,5-pentafluoropentylsulfinyl)-nonyl]-estra-1,3,5(10)-triene-3,17β-diol a) 3,11α-Diacetoxy-estra-3,5-dien-17-one 10 g of p-toluenesulfonic acid is added to 100 g of 11α-hydroxy-estr-4-ene-3,17-dione in 1 liter of acetic anhydride at room temperature. After 5 hours, the solution is stirred into pyridine-containing ice/water, the precipitated product is suctioned off and washed neutral with water. The water-moistened crude product that is obtained is mixed with 200 ml of methanol, stirred for 30 minutes at −30° C., the crystallizate is suctioned off, washed with cold methanol and dried in a vacuum at 50° C. 115 g of 3,11α-diacetoxy-estra-3,5-dien-17-one is obtained.

b) 11α-Acetoxy-estra-4,6-diene-3,17-dione 48 ml of a 10% aqueous sodium acetate solution and, in portions, 22.3 g of 1,3-dibromo-5,5-dimethylhydantoin are added to 57 g of 3,11α-diacetoxy-estra-3,5-dien-17-one in 470 ml of N-methyl-2-pyrrolidinone while being cooled with ice. After 30 minutes, 16.7 g of sodium sulfite is added, it is stirred for 15 minutes at 0° C., then mixed with 20 g of lithium bromide and 16 g of lithium carbonate and stirred at 100° C. After 2 hours, the reaction mixture is added to ice/water. The precipitated product is suctioned off, dissolved in methylene chloride, washed neutral with water and dried. The crude product is recrystallized from 200 ml of ethyl acetate. 30 g of 11α-acetoxy-estra-4,6-diene-3,17-dione with a melting point of 246–248° C. is obtained.

c) 11α-Acetoxy-7α-(9-tert-butyldimethylsilyloxynonyl)-estr-4-ene-3,17-dione

The Grignard solution of 2.2 g of magnesium chips and 34.2 g of 1-bromo-9-tert-butyl-dimethyl-silyloxynonane (produced from 9-bromo-1-nonanol and tert-butyl-dimethylsilyl chloride) in 140 ml of tetrahydrofuran is mixed at −30° C. with 8.8 g of copper(I) iodide. After 30 minutes, at the same temperature, the solution of 9 g of 11α-acetoxy-estra-4,6-diene-3,17-dione in a mixture of 64 ml of tetrahydrofuran and 10.6 ml of 1,3-dimethyl-2-oxohexahydropyrimidine (DMPU) is added in drops at −30° C., stirred for 2 hours and then mixed with 6 ml of glacial acetic acid. The reaction mixture is diluted after 15 minutes with ethyl acetate, washed neutral with saturated ammonium chloride solution and water and dried. After the crude product is chromatographed on silica gel with a hexane-ethyl acetate gradient, 6 g of 11α-acetoxy-7α-(9-tert-butyldimethylsilyloxynonyl)-estr-4-ene-3,17-dione with a melting point of 120–122° C. is obtained.

d) 11α-Acetoxy-7α-(9-hydroxynonyl)-estr-4-ene-3,17-dione 19.9 g of 11α-acetoxy-7α-(9-tert-butyldimethylsilyloxynonyl)-estr-4-ene-3,17-dione in 90 ml of methanol is mixed at room temperature with 20 ml of 8% sulfuric acid. After 2.5 hours, it is diluted with ethyl acetate, washed neutral with saturated sodium bicarbonate solution and water and dried. The chromatography of the crude product on silica gel with a methylene chloride-acetone gradient yields 15.8 g of 11α-acetoxy-7α-(9-hydroxynonyl)-estr-4-ene-3,17-dione as a foam.

e) 11α-Acetoxy-7α-(9-chlorononyl)-estr-4-ene-3,17-dione 15.8 g of 11α-acetoxy-7α-(9-hydroxynonyl)-estr-4-ene-3,17-dione is reacted in 65 ml of acetonitrile with 184 ml of tetrachloromethane and 17.9 g of triphenylphosphine at room temperature. After 5 hours, it is diluted with methylene chloride, washed neutral with saturated sodium bicarbonate solution and water and dried. The crude product is chromatographed on silica gel with a hexane-ethyl acetate gradient. Yield: 7.8 g of 11α-acetoxy-7α-(9-chlorononyl)-estr-4-ene-3,17-dione with a melting point of 113–115° C.

f) 7α-(9-Chlorononyl)-11α-hydroxy-estr-4-ene-3,17-dione 6.0 g of 11α-acetoxy-7α-(9-chlorononyl)-estr-4-ene-3,17-dione is saponified at 60° C. in a mixture of 12 ml of tetrahydrofuran and 12 ml of methanol with 17 ml of a 1N potassium hydroxide solution. After 3 hours, it is diluted with ethyl acetate, washed neutral with saturated sodium chloride solution and water and dried. The chromatography of the crude product on silica gel with a methylene chloride-acetone gradient yields 3.2 g of 7α-(9-chlorononyl)-11α-hydroxy-estr-4-ene-3,17-dione as an oil.

g) 7α-(9-Chlorononyl)-11β-fluor-estr-4-ene-3,17-dione 3.3 ml of 1,8-diazabicyclo[5,4,0]undec-7-ene and, drop by drop, 4 ml of perfluorobutane-1-sulfonic acid fluoride are added to 6.7 g of 7α-(9-chlorononyl)-11-hydroxy-estr-4-ene-3,17-dione in 35 ml of ethyl acetate at 0° C. After 2 hours, it is diluted with ethyl acetate, washed several times with 2N hydrochloric acid and neutralized with saturated sodium bicarbonate solution and water. The crude product is chromatographed on silica gel with a hexane-ethyl acetate gradient. Yield: 6.2 g of 7α-(9-chlorononyl)-11β-fluor-estr-4-ene-3,17-dione as an oil.

h) 7α-(9-Chlorononyl)-11β-fluoro-3-hydroxy-estra-1,3,5(10)-triene-17-dione

A solution of 5.5 g of copper(II) bromide and 1.1 g of lithium bromide in 55 ml of acetonitrile is added in drops to 5.6 g of 7α-(9-chlorononyl)-11β-fluor-estr-4-ene-3,17-dione in 55 ml of acetonitrile at 80° C. After 2 hours, it is diluted with ethyl acetate, neutralized with sodium bicarbonate solution, washed with water, dried and concentrated by evaporation in a vacuum. The chromatography on silica gel with a hexane-ether gradient yields 1.1 g of 7α-(9-chlorononyl)-11β-fluoro-3-hydroxy-estra-1,3,5(10)-triene-17-dione as a foam.

i) 7α-(9-Chlorononyl)-11β-fluoro-3-(tetrahydropyran-2-yloxy)-estra-1,3,5(10)-triene-17-dione 3.0 g of 7α-(9-chlorononyl)-11β-fluoro-3-hydroxy-estra-1,3,5(10)-triene-17-dione in 30 ml of tetrahydrofuran is reacted at room temperature with 2.9 ml of 3,4-dihydropyran and 150 mg of p-toluenesulfonic acid hydrate. After 3 hours, it is diluted with ethyl acetate, neutralized with saturated sodium bicarbonate solution and water, dried and concentrated by evaporation in a vacuum. After chromatography on silica gel with a hexane-ethyl acetate gradient, the crude product yields 2.8 g of 7α-(9-chlorononyl)-11β-fluoro-3-(tetrahydropyran-2-yloxy)-estra-1,3,5(10)-triene-17-dione as an oil.

j) 11β-Fluoro-7α-(9-iodononyl)-3-(tetrahydropyran-2-yloxy)-estra-1,3,5(10)-triene-17-dione 2.6 g of 7α-(9-chlorononyl)-11β-fluoro-3-(tetrahydropyran-2-yloxy)-estra-1,3,5(10)-triene-17-dione in 20 ml of ethylmethylketone is stirred at 80° C. with 2.9 g of sodium iodide. After 20 hours, it is diluted with ether, washed with water, dried and concentrated by evaporation in a vacuum. The crude product is chromatographed on silica gel with a hexane-ether gradient. Yield: 1.2 g of 11β-fluor-7α-(9-iodononyl)-3-(tetrahydropyran-2-yloxy)-estra-1,3,5(10)-triene-17-dione as an oil.

k) 11β-Fluoro-[9-(4,4,5,5,5-pentafluoropentylthio)-nonyl]-3-(tetrahydropyran-2-yloxy)-estra-1,3,5(10)-trien-17-one 0.83 ml of 30% methanolic sodium methylate solution is added in drops to 980 mg of 5-(4,4,5,5,5-pentafluoropentyl)thioacetate in 10 ml of methanol while being cooled with ice. It is stirred for 30 minutes at room temperature. Then, the solution of 1.9 g of 11β-fluor-7α-(9-iodononyl)-3-(tetrahydropyran-2-yloxy)-estra-1,3,5(10)-triene-17-dione in 10 ml of dimethylformamide is added and stirred at 50° C. After 18 hours, it is diluted with ether, washed neutral with saturated sodium chloride solution and water, dried and concentrated by evaporation in a vacuum. The crude product is chromatographed on silica gel with a hexane-ether gradient. 1.3 g of 11β-fluorine-[9-(4,4,5,5,5-pentafluoropentylthio)-nonyl]-3-(tetrahydropyran-2-yloxy)-estra-1,3,5(10)-trien-17-one is obtained as an oil.

l) 11β-Fluoro-[9-(4,4,5,5,5-pentafluoropentylthio)-nonyl]-3-(tetrahydropyran-2-yloxy)-estra-1,3,5(10)-trien-17β-ol 2.2 g of 11β-fluoro-[9-(4,4,5,5,5-pentafluoropentylthio)-nonyl]-3-(tetrahydropyran-2-yloxy)-estra-1,3,5(10)-triene-17-one in a mixture of 45 ml of methanol, 7 ml of tetrahydrofuran and 4.5 ml of water is mixed in portions with 450 mg of sodium borohydride at 0° C. After 45 minutes, it is diluted with ethyl acetate, washed with water, dried and concentrated by evaporation. Chromatography of the crude product on silica gel with a hexane-ethyl acetate gradient yields 1.8 g of 11β-fluoro-[9-(4,4,5,5,5-pentafluoropentylthio)-nonyl]-3-(tetrahydropyran-2-yloxy)-estra-1,3,5(10)-trien-17β-ol as an oil.

m) 11β-Fluoro-[9-(4,4,5,5,5-pentafluoropentylthio)-nonyl]-estra-1,3,5(10)-trien-3,17β-ol 1.8 g of 11β-fluoro-[9-(4,4,5,5,5-pentafluoropentylthio)-nonyl]-3-(tetrahydropyran-2-yloxy)-estra-1,3,5(10)-trien-17β-ol in 68 ml of methanol and 6.8 ml of water are allowed to react with 900 mg of oxalic acid at 60° C. After 2 hours, it is diluted with ethyl acetate, neutralized with sodium bicarbonate solution, washed with water, dried and concentrated by evaporation. The chromatography of the crude product on silica gel with a hexane-ethyl acetate gradient yields 1.4 g of 11β-fluoro-[9-(4,4,5,5,5-pentafluoropentylthio)-nonyl]-estra-1,3,5(10)-trien-3,17β-ol as a foam.

n) 11β-Fluoro-[9-(4,4,5,5,5-pentafluoropentylsulfinyl)-nonyl]-estra-1,3,5(10)-trien-3,17β-ol 300 mg of 11β-fluoro-[9-(4,4,5,5,5-pentafluoropentylthio)-nonyl]-estra-1,3,5(10)-trien-3,17β-ol in 12 ml of methanol and 2.4 ml of water are mixed at room temperature with 241 mg of sodium periodate. After 1.5 hours, it is diluted with ethyl acetate, washed neutral with saturated sodium chloride solution and water, dried and concentrated by evaporation in a vacuum. The crude product is chromatographed on silica gel with a methylene chloride-acetone gradient. Yield: 287 mg of 11β-fluoro-[9-(4,4,5,5,5-pentafluoropentylsulfinyl)-nonyl]-estra-1,3,5(10)-trien-3,17β-ol as a foam.

Example 25

N-[4-(11β-Fluoro-3,17-dihydroxy-estra-1,3,5(10)-trien-7α-yl)-butyl]-N-pentyl-benzamide a) 3-Benzyloxy-7α-(4-chlorobutyl)-11β-fluor-estra-1,3,5(10)-trien-17-one A solution of 3.9 g of 7α-(4-chlorobutyl)-11β-fluoro-3-hydroxy-estra-1,3,5(10)-trien-17-one, which was produced analogously to the 6-chlorohexyl compound described in Example 4b), in 100 ml of acetonitrile is stirred with 2.28 g of potassium carbonate and 2.11 g of benzyl bromide for 24 hours at a bath temperature of 80° C. Then, it is evaporated to the dry state, mixed with water, extracted twice with dichloromethane, washed with water and saturated common salt solution, dried on sodium sulfate, concentrated by evaporation in a vacuum and chromatographed on silica gel with dichloromethane/ethyl acetate. 5.14 g of 3-benzyloxy-7α-(4-chlorobutyl)-11β-fluor-estra-1,3,5(10)-trien-17-one is obtained as a foam.

b) 7α-(5-Azadecyl)-3-benzyloxy-11β-fluor-estra-1,3,5(10)-trien-17-one

A solution of 273 mg of 3-benzyloxy-7α-(4-chlorobutyl)-11β-fluor-estra-1,3,5(10)-trien-17-one in 7 ml of dimethylformamide is stirred with 262 mg of sodium iodide and 0.5 ml of n-pentylamine for 24 hours at 80° C. Then, the reaction mixture is added to ice water, extracted with ethyl acetate, washed with saturated sodium chloride solution, dried and concentrated by evaporation in a vacuum. After the crude product is chromatographed on silica gel with a methylene chloride-methanol gradient, 275 mg of 7α-(5-azadecyl)-3-benzyloxy-11β-fluor-estra-1,3,5(10)-trien-17-one is obtained.

c) N-[4-(3-Benzyloxy-11β-fluor-estra-1,3,5(10)-trien-17-on-7α-yl)-butyl]-N-pentyl-benzamide A solution of 275 mg of 7α-(5-azadecyl)-3-benzyloxy-11β-fluor-estra-1,3,5(10)-trien-17-one in 7.8 ml of dimethylformamide is stirred with 175 mg of benzoic acid and 250 mg of 1-hydroxybenzotriazole and 0.2 ml of N,N'-diisopropylcarbodiimide for 24 hours at room temperature. Then, the reaction mixture is added to ice water, extracted with ethyl acetate, washed with saturated sodium chloride solution, dried and concentrated by evaporation in a vacuum. After the crude product is chromatographed on silica gel with a methylene chloride-methanol gradient, 197 mg of N-[4-(3-benzyloxy-11β-fluor-estra-1,3,5(10)-trien-17-on-7α-yl)-butyl]-N-pentyl-benzamide is obtained.

d) N-[4-(11β-Fluoro-3-hydroxy-estra-1,3,5(10)-trien-17-on-7α-yl)-butyl]-N-pentyl-benzamide A solution of 197 mg of N-[4-(3-benzyloxy-11β-fluor-estra-1,3,5(10)-trien-17-on-7α-yl)-butyl]-N-pentyl-benzamide in 4.8 ml of dichloromethane is stirred with 2 ml of thioanisole and 1.2 ml of trifluoroacetic acid for 3 hours at room temperature. Then, it is diluted with dichloromethane, washed with 1 molar sodium hydroxide solution, washed neutral with water, dried on sodium sulfate, concentrated by evaporation in a vacuum and chromatographed on silica gel with dichloromethane/methyl-tert-butylether. 147 mg of N-[4-(11β-fluoro-3-hydroxy-estra-1,3,5(10)-trien-17-on-7α-yl-butyl)-N-pentyl-benzamide is obtained.

e) N-[4-(11β-Fluoro-3,17-dihydroxy-estra-1,3,5(10)-trien-7α-yl)-butyl]-N-pentyl-benzamide A solution of 110 mg of N-[4-(113-fluoro-3-hydroxy-estra-1,3,5(10)-trien-17-on-7α-yl)-butyl]-N-pentyl-benzamide in 1.5 ml of dichloromethane and 4.5 ml of methanol are mixed at room temperature with 110 mg of sodium borohydride and stirred for 0.5 hour. Then, it is diluted with water, extracted with 25 ml of ethyl acetate, washed twice with water, dried on sodium sulfate, concentrated by evaporation in a vacuum and chromatographed on silica gel with hexane/ethyl acetate. 112 mg of pure N-[4-(11β-fluoro-3,17-dihydroxy-estra-1,3,5(10)-trien-7α-yl)-butyl]-N-pentyl-benzamide is obtained as a foam. $[\alpha]^{22}_D$=+42.3° (c=0.51% in chloroform).

By selection of one each of the following ω-chlorides for reaction step a): 7α-(4-chlorobutyl)-11β-fluoro-3-hydroxy-estra-1,3,5(10)-trien-17-one, 7α-(5-chloropentyl)-11β-fluoro-3-hydroxy-estra-1,3,5(10)-trien-17-one (Example 2b)) and 7α-(6-chlorohexyl)-11β-fluoro-3-hydroxy-estra-1,3,5(10)-trien-17-one (Example 4b))

and one each of the following amines for reaction step b): aminomethylcyclohexane, benzylamine, 2-methoxyethylamine, 3-phenylpropylamine, hexylamine and octylamine and one each of the following acids for reaction step c): 4-acetaminobenzoic acid, 4-cyanobenzoic acid, 3-cyclohexylpropionic acid, 3,4-dimethoxyphenylacetic acid, 4-ethoxybenzoic acid, lauric acid, 2-naphthylacetic acid, 4-phenylbutyric acid, propionic acid and 4-biphenylacetic acid, the compounds of the following table are obtained by analogous implementation of reaction steps a–e that are described in Example 25.

Instead of reaction with an activated acid in reaction step c), this reaction can also be carried out with an alkyl halide (halogen=Cl, Br), whereby then instead of the amide, an amine is obtained directly.

In the table, the $[M]^+$+1 peaks of mass spectra (MS) of these compounds are indicated; CI=Chemical Ionization.

| Example | Compound | MS (CI): $[M]^+ + 1$ [m/z] |
|---|---|---|
| 26 | 4-Acetylamino-N-cyclohexylmethyl-N-[4-(11β-fluoro-3,17β-dihydroxy-estra-1,3,5(10)-trien-7α-yl)-butyl]-benzamide | 619 |
| 27 | 4-Acetylamino-N-benzyl-N-[4-(11β-fluoro-3,17β-dihydroxy-estra-1,3,5(10)-trien-7α-yl)-butyl]-benzamide | 613 |
| 28 | 4-Acetylamino-N-[4-(11β-fluoro-3,17β-dihydroxy-estra-1,3,5(10)-trien-7α-yl)-butyl]-N-(2-methoxy-ethyl)-benzamide | 581 |
| 29 | 4-Acetylamino-N-[4-(11β-fluoro-3,17β-dihydroxy-estra-1,3,5(10)-trien-7α-yl)-butyl]-N-(3-phenyl-propyl)-benzamide | 641 |
| 30 | 4-Acetylamino-N-[4-(11β-fluoro-3,17β-dihydroxy-estra-1,3,5(10)-trien-7α-yl)-butyl]-N-hexyl-benzamide | 607 |

| Example | Compound | MS (CI): [M]⁺ + 1 [m/z] |
|---|---|---|
| 31 | 4-Acetylamino-N-[4-(11β-fluoro-3,17β-dihydroxy-estra-1,3,5(10)-trien-7α-yl)-butyl]-N-octyl-benzamide | 635 |
| 32 | 4-Cyano-N-cyclohexylmethyl-N-[4-(11β-fluoro-3,17β-dihydroxy-estra-1,3,5(10)-trien-7α-yl)-butyl]-benzamide | 587 |
| 33 | N-Benzyl-4-cyano-N-[4-(11β-fluoro-3,17β-dihydroxy-estra-1,3,5(10)-trien-7α-yl-butyl]-benzamide | 581 |
| 34 | 4-Cyano-N-[4-(11β-fluoro-3,17β-dihydroxy-estra-1,3,5(10)-trien-7α-yl)-butyl]-N-(2-methoxy-ethyl)-benzamide | 549 |
| 35 | 4-Cyano-N-[4-(11β-fluoro-3,17β-dihydroxy-estra-1,3,5(10)-trien-7α-yl)-butyl]-N-(3-phenyl-propyl)-benzamide | 609 |
| 36 | 4-Cyano-N-[4-(11β-fluoro-3,17β-dihydroxy-estra-1,3,5(10)-trien-7α-yl)-butyl]-N-hexyl-benzamide | 575 |
| 37 | 4-Cyano-N-[4-(11β-fluoro-3,17β-dihydroxy-estra-1,3,5(10)-trien-7α-yl)-butyl)-N-octyl-benzamide | 603 |
| 38 | 3-Cyclohexyl-N-cyclohexylmethyl-N-[4-(11β-fluoro-3,17β-dihydroxy-estra-1,3,5(10)-trien-7α-yl)-butyl]-propionamide | 596 |
| 39 | N-Benzyl-3-cyclohexyl-N-[4-(11β-fluoro-3,17β-dihydroxy-estra-1,3,5(10)-trien-7α-yl)-butyl]-propionamide | 590 |
| 40 | 3-Cyclohexyl-N-[4-(11β-fluoro-3,17β-dihydroxy-estra-1,3,5(10)-trien-7α-yl)-butyl]-N-(2-methoxy-ethyl)-propionamide | 558 |
| 41 | 3-Cyclohexyl-N-[4-(11β-fluoro-3,17β-dihydroxy-estra-1,3,5(10)-trien-7α-yl)-butyl]-N-(3-phenyl-propyl)-propionamide | 618 |
| 42 | 3-Cyclohexyl-N-[4-(11β-fluoro-3,17β-dihydroxy-estra-1,3,5(10)-trien-7α-yl)-butyl]-N-hexyl-propionamide | 584 |
| 43 | 3-Cyclohexyl-N-[4-(11β-fluoro-3,17β-dihydroxy-estra-1,3,5(10)-trien-7α-yl)-butyl)-N-octyl-propionamide | 612 |
| 44 | N-Cyclohexylmethyl-N-[4-(11β-fluoro-3,17β-dihydroxy-estra-1,3,5(10)-trien-7α-yl)-butyl]-(3,4-dimethoxyphenyl)-acetamide | 636 |
| 45 | N-Benzyl-N-[4-(11β-fluoro-3,17β-dihydroxy-estra-1,3,5(10)-trien-7α-yl)-butyl]-(3,4-dimethoxyphenyl)-acetamide | 630 |
| 46 | N-[4-(11β-Fluoro-3,17β-dihydroxy-estra-1,3,5(10)-trien-7α-yl)-butyl]-N-(2-methoxy-ethyl)-(3,4-dimethoxyphenyl)-acetamide | 598 |
| 47 | N-[4-(11β-Fluoro-3,17β-dihydroxy-estra-1,3,5(10)-trien-7α-yl)-butyl]-(3,4-dimethoxyphenyl)-N-(3-phenyl-propyl)-acetamide | 658 |
| 48 | N-[4-(11β-Fluoro-3,17β-dihydroxy-estra-1,3,5(10)-trien-7α-yl)-butyl]-N-hexyl-(3,4-dimethoxyphenyl)-acetamide | 624 |
| 49 | N-[4-(11β-Fluoro-3,17β-dihydroxy-estra-1,3,5(10)-trien-7α-yl)-butyl]-(3,4-dimethoxyphenyl)-N-octyl-acetamide | 652 |
| 50 | N-Cyclohexylmethyl-4-ethoxy-N-[4-(11β-fluoro-3,17β-dihydroxy-estra-1,3,5(10)-trien-7α-yl)-butyl]-benzamide | 606 |
| 51 | N-Benzyl-4-ethoxy-N-[4-(11β-fluoro-3,17β-dihydroxy-estra-1,3,5(10)-trien-7α-yl)-butyl]-benzamide | 600 |
| 52 | 4-Ethoxy-N-[4-(11β-fluoro-3,17β-dihydroxy-estra-1,3,5(10)-trien-7α-yl)-butyl]-N-(2-methoxy-ethyl)-benzamide | 568 |
| 53 | 4-Ethoxy-N-[4-(11β-fluoro-3,17β-dihydroxy-estra-1,3,5(10)-trien-7α-yl)-butyl]-N-(3-phenyl-propyl)-benzamide | 628 |
| 54 | 4-Ethoxy-N-[4-(11β-fluoro-3,17β-dihydroxy-estra-1,3,5(10)-trien-7α-yl)-butyl]-N-hexyl-benzamide | 594 |
| 55 | 4-Ethoxy-N-[4-(11β-fluoro-3,17β-dihydroxy-estra-1,3,5(10)-trien-7α-yl)-butyl]-N-octyl-benzamide | 622 |
| 56 | N-Cyclohexylmethyl-N-[4-(11β-fluoro-3,17β-dihydroxy-estra-1,3,5(10)-trien-7α-yl)-butyl)-dodecanamide | 640 |
| 57 | N-Benzyl-N-[4-(11β-fluoro-3,17β-dihydroxy-estra-1,3,5(10)-trien-7α-yl)-butyl]-dodecanamide | 634 |
| 58 | N-[4-(11β-Fluoro-3,17β-dihydroxy-estra-1,3,5(10)-trien-7α-yl)-butyl]-N-(2-methoxy-ethyl)-dodecanamide | 602 |
| 59 | N-[4-(11β-fluoro-3,17β-dihydroxy-estra-1,3,5(10)-trien-7α-yl)-butyl]-N-(3-phenyl-propyl)-dodecanamide | 662 |
| 60 | N-[4-(11β-Fluoro-3,17β-dihydroxy-estra-1,3,5(10)-trien-7α-yl)-butyl]-N-hexyl-dodecanamide | 628 |
| 61 | N-[4-(11β-Fluoro-3,17β-dihydroxy-estra-1,3,5(10)-trien-7α-yl)-butyl]-N-hexyl-dodecanamide | 657 |
| 62 | N-Cyclohexylmethyl-N-[4-(11β-fluoro-3,17β-dihydroxy-estra-1,3,5(10)-trien-7α-yl)-butyl]-naphth-2-yl-acetamide | 626 |
| 63 | N-Benzyl-N-[4-(11β-fluoro-3,17β-dihydroxy-estra-1,3,5(10)-trien-7α-yl)-butyl]-naphth-2-yl-acetamide | 620 |
| 64 | N-[4-(11β-Fluoro-3,17β-dihydroxy-estra-1,3,5(10)-trien-7α-yl)-butyl]-N-(2-methoxy-ethyl)-naphth-2-yl-acetamide | 588 |
| 65 | N-[4-(11β-Fluoro-3,17β-dihydroxy-estra-1,3,5(10)-trien-7α-yl)-butyl)-naphth-2-yl-N-(3-phenyl-propyl)-acetamide | 648 |
| 66 | N-[4-(11β-Fluoro-3,17β-dihydroxy-estra-1,3,5(10)-trien-7α-yl)-butyl]-N-hexyl-naphth-2-yl-acetamide | 614 |
| 67 | N-[4-(11β-Fluoro-3,17β-dihydroxy-estra-1,3,5(10)-trien-7α-yl)-butyl]-naphth-2-yl-N-octyl-acetamide | 642 |
| 68 | N-cyclohexylmethyl-N-[4-(11β-fluoro-3,17β-dihydroxy-estra-1,3,5(10)-trien-7α-yl)-butyl]-4-phenyl-butyramide | 604 |
| 69 | N-Benzyl-N-[4-(11β-fluoro-3,17β-dihydroxy-estra-1,3,5(10)-trien-7α-yl)-butyl]-4-phenyl-butyramide | 598 |
| 70 | N-[4-(11β-Fluoro-3,17β-dihydroxy-estra-1,3,5(10)-trien-7α-yl)-butyl]-N-(2-methoxy-ethyl)-4-phenyl-butyramide | 566 |
| 71 | N-[4-(11β-Fluoro-3,17β-dihydroxy-estra-1,3,5(10)-trien-7α-yl)-butyl]-4-phenyl-N-(3-phenyl-propyl)-butyramide | 626 |
| 72 | N-[4-(11β-Fluoro-3,17β-dihydroxy-estra-1,3,5(10)-trien-7α-yl)-butyl]-N-hexyl-4-phenyl-butyramide | 592 |
| 73 | N-[4-(11β-Fluoro-3,17β-dihydroxy-estra-1,3,5(10)-trien-7α-yl)-butyl)-N-octyl-4-phenyl-butyramide | 620 |
| 74 | N-Cyclohexylmethyl-N-[4-(11β-fluoro-3,17β-dihydroxy-estra-1,3,5(10)-trien-7α-yl)-butyl]-propionamide | 514 |
| 75 | N-Benzyl-N-[4-(11β-fluoro-3,17β-dihydroxy-estra-1,3,5(10)-trien-7α-yl)-butyl]-propionamide | 508 |
| 76 | N-[4-(11β-Fluoro-3,17β-dihydroxy-estra-1,3,5(10)-trien-7α-yl)-butyl]-N-(2-methoxy-ethyl)-propionamide | 476 |
| 77 | N-[4-(11β-Fluoro-3,17β-dihydroxy-estra-1,3,5(10)-trien-7α-yl)-butyl]-N-(3-phenyl-propyl)-propionamide | 536 |
| 78 | N-[4-(11β-Fluoro-3,17β-dihydroxy-estra-1,3,5(10)-trien-7α-yl)-butyl]-N-hexyl-propionamide | 502 |
| 79 | N-[4-(11β-Fluoro-3,17β-dihydroxy-estra-1,3,5(10)-trien-7α-yl)-butyl]-N-octyl-propionamide | 530 |

| Example | Compound | MS (CI): [M]⁺ + 1 [m/z] |
|---|---|---|
| 80 | 4-Biphenyl-N-cyclohexylmethyl-N-[4-(11β-fluoro-3,17β-dihydroxy-estra-1,3,5(10)-trien-7α-yl)-butyl]-acetamide | 652 |
| 81 | 4-Biphenyl-N-benzyl-N-[4-(11β-fluoro-3,17β-dihydroxy-estra-1,3,5(10)-trien-7α-yl)-butyl]-acetamide | 646 |
| 82 | 4-Biphenyl-N-[4-(11β-fluoro-3,17β-dihydroxy-estra-1,3,5(10)-trien-7α-yl)-butyl]-N-(2-methoxy-ethyl)-acetamide | 614 |
| 83 | 4-Biphenyl-N-[4-(11β-fluoro-3,17β-dihydroxy-estra-1,3,5(10)-trien-7α-yl)-butyl]-N-(3-phenyl-propyl)-acetamide | 674 |
| 84 | 4-Biphenyl-N-[4-(11β-fluoro-3,17β-dihydroxy-estra-1,3,5(10)-trien-7α-yl)-butyl]-N-hexyl-acetamide | 640 |
| 85 | 4-Biphenyl-N-[4-(11β-fluoro-3,17β-dihydroxy-estra-1,3,5(10)-trien-7α-yl)-butyl]-N-octyl-acetamide | 668 |
| 86 | 4-Acetylamino-N-cyclohexylmethyl-N-[5-(11β-fluoro-3,17β-dihydroxy-estra-1,3,5(10)-trien-7α-yl)-pentyl]-benzamide | 633 |
| 87 | 4-Acetylamino-N-benzyl-N-[5-(11β-fluoro-3,17β-dihydroxy-estra-1,3,5(10)-trien-7α-yl)-pentyl]-benzamide | 627 |
| 88 | 4-Acetylamino-N-[5-(11β-fluoro-3,17β-dihydroxy-estra-1,3,5(10)-trien-7α-yl)-pentyl]-N-(2-methoxy-ethyl)-benzamide | 595 |
| 89 | 4-Acetylamino-N-[5-(11β-fluoro-3,17β-dihydroxy-estra-1,3,5(10)-trien-7α-yl)-pentyl]-N-(3-phenyl-propyl)-benzamide | 655 |
| 90 | 4-Acetylamino-N-[5-(11β-fluoro-3,17β-dihydroxy-estra-1,3,5(10)-trien-7α-yl)-pentyl]-N-hexyl-benzamide | 621 |
| 91 | 4-Acetylamino-N-[5-(11β-fluoro-3,17β-dihydroxy-estra-1,3,5(10)-trien-7α-yl)-pentyl]-N-octyl-benzamide | 649 |
| 92 | 4-Cyano-N-cyclohexylmethyl-N-[5-(11β-fluoro-3,17β-dihydroxy-estra-1,3,5(10)-trien-7α-yl)-pentyl)-benzamide | 601 |
| 93 | N-Benzyl-4-cyano-N-[5-(11β-fluoro-3,17β-dihydroxy-estra-1,3,5(10)-trien-7α-yl)-pentyl]-benzamide | 595 |
| 94 | 4-Cyano-N-[5-(11β-fluoro-3,17β-dihydroxy-estra-1,3,5(10)-trien-7α-yl)-pentyl]-N-(2-methoxy-ethyl)-benzamide | 563 |
| 95 | 4-Cyano-N-[5-(11β-fluoro-3,17β-dihydroxy-estra-1,3,5(10)-trien-7α-yl)-pentyl]-N-(3-phenyl-propyl)-benzamide | 623 |
| 96 | 4-Cyano-N-[5-(11β-fluoro-3,17β-dihydroxy-estra-1,3,5(10)-trien-7α-yl)-pentyl]-N-hexyl-benzamide | 589 |
| 97 | 4-Cyano-N-[5-(11β-fluoro-3,17β-dihydroxy-estra-1,3,5(10)-trien-7α-yl)-pentyl)-N-octyl-benzamide | 617 |
| 98 | 3-cyclohexyl-N-cyclohexylmethyl-N-[5-(11β-fluoro-3,17β-dihydroxy-estra-1,3,5(10)-trien-7α-yl)-pentyl]-propionamide | 610 |
| 99 | N-Benzyl-3-cyclohexyl-N-[5-(11β-fluoro-3,17β-dihydroxy-estra-1,3,5(10)-trien-7α-yl)-pentyl]-propionamide | 604 |
| 100 | 3-Cyclohexyl-N-[5-(11β-fluoro-3,17β-dihydroxy-estra-1,3,5(10)-trien-7α-yl)-pentyl]-N-(2-methoxy-ethyl)-propionamide | 572 |
| 101 | 3-Cyclohexyl-N-[5-(11β-fluoro-3,17β-dihydroxy-estra-1,3,5(10)-trien-7α-yl)-pentyl]-N-(3-phenyl-propyl)-propionamide | 632 |
| 102 | 3-Cyclohexyl-N-[5-(11β-fluoro-3,17β-dihydroxy-estra-1,3,5(10)-trien-7α-yl)-pentyl]-N-hexyl-propionamide | 598 |
| 103 | 3-Cyclohexyl-N-[5-(11β-fluoro-3,17β-dihydroxy-estra-1,3,5(10)-trien-7α-yl)-pentyl]-N-octyl-propionamide | 626 |
| 104 | N-Cyclohexylmethyl-N-[5-(11β-fluoro-3,17β-dihydroxy-estra-1,3,5(10)-trien-7α-yl)-pentyl]-(3,4-dimethoxyphenyl)-acetamide | 650 |
| 105 | N-Benzyl-N-[5-(11β-fluoro-3,17β-dihydroxy-estra-1,3,5(10)-trien-7α-yl)-pentyl]-(3,4-dimethoxyphenyl)-acetamide | 644 |
| 106 | N-[5-(11β-Fluoro-31 17β-dihydroxy-estra-1,3,5(10)-trien-7α-yl)-pentyl]-N-(2-methoxy-ethyl)-(3,4-dimethoxyphenyl)-acetamide | 612 |
| 107 | N-[5-(11β-Fluoro-3,17β-dihydroxy-estra-1,3,5(10)-trien-7α-yl)-pentyl]-(3,4-dimethoxyphenyl)-N-(3-phenyl-propyl)-acetamide | 672 |
| 108 | N-[5-(11β-Fluoro-3,17β8-dihydroxy-estra-1,3,5(10)-trien-7α-yl)-pentyl]-N-hexyl-(3,4-dimethoxyphenyl)-acetamide | 638 |
| 109 | N-[5-(11β-Fluoro-3,17β-dihydroxy-estra-1,3,5(10)-trien-7α-yl)-pentyl]-(3,4-dimethoxyphenyl)-N-octyl-acetamide | 666 |
| 110 | N-Cyclohexylmethyl-4-ethoxy-N-[5-(11β-fluoro-3,17β-dihydroxy-estra-1,3,5(10)-trien-7α-yl)-pentyl]-benzamide | 620 |
| 111 | N-Benzyl-4-ethoxy-N-[5-(11β-fluoro-3,17β-dihydroxy-estra-1,3,5(10)-trien-7α-yl)-pentyl]-benzamide | 614 |
| 112 | 4-Ethoxy-N-[5-(11β-fluoro-3,17β-dihydroxy-estra-1,3,5(10)-trien-7α-yl)-pentyl]-N-(2-methoxy-ethyl)-benzamide | 582 |
| 113 | 4-Ethoxy-N-[5-(11β-fluoro-3,17β-dihydroxy-estra-1,3,5(10)-trien-7α-yl)-pentyl]-N-(3-phenyl-propyl)-benzamide | 642 |
| 114 | 4-Ethoxy-N-[5-(11β-fluoro-3,17β-dihydroxy-estra-1,3,5(10)-trien-7α-yl)-pentyl]-N-hexyl-benzamide | 608 |
| 115 | 4-Ethoxy-N-[5-(11β-fluoro-3,17β-dihydroxy-estra-1,3,5(10)-trien-7α-yl)-pentyl)-N-octyl-benzamide | 636 |
| 116 | N-Cyclohexylmethyl-N-[5-(11β-fluoro-3,17β-dihydroxy-estra-1,3,5(10)-trien-7α-yl)-pentyl]-dodecanamide | 654 |
| 117 | N-Benzyl-N-[5-(11β-fluoro-3,17β-dihydroxy-estra-1,3,5(10)-trien-7α-yl)-pentyl]-dodecanamide | 648 |
| 118 | N-[5-(11β-Fluoro-3,17β-dihydroxy-estra-1,3,5(10)-trien-7α-yl)-pentyl]-N-(2-methoxy-ethyl)-dodecanamide | 616 |
| 119 | N-[5-(11β-Fluoro-3,17β-dihydroxy-estra-1,3,5(10)-trien-7α-yl)-pentyl]-N-(3-phenyl-propyl)-dodecanamide | 676 |
| 120 | N-[5-(11β-Fluoro-3,17β-dihydroxy-estra-1,3,5(10)-trien-7α-yl)-pentyl]-N-hexyl-dodecanamide | 642 |
| 121 | N-[5-(11β-Fluoro-3,17β-dihydroxy-estra-1,3,5(10)-trien-7α-yl)-pentyl]-N-octyl-dodecanamide | 671 |
| 122 | N-Cyclohexylmethyl-N-[5-(11β-fluoro-3,17β-dihydroxy-estra-1,3,5(10)-trien-7α-yl)-pentyl]-naphth-2-yl-acetamide | 640 |
| 123 | N-Benzyl-N-[5-(11β-fluoro-3,17β-dihydroxy-estra-1,3,5(10)-trien-7α-yl)-pentyl]-naphth-2-yl-acetamide | 634 |
| 124 | N-[5-(11β-Fluoro-3,17β-dihydroxy-estra-1,3,5(10)-trien-7α-yl)-pentyl)-N-(2-methoxy-ethyl)-naphth-2-yl-acetamide | 602 |
| 125 | N-[5-(11β-Fluoro-3,17β-dihydroxy-estra-1,3,5(10)-trien-7α-yl)-pentyl]-naphth-2-yl-N-(3-phenyl-propyl)-acetamide | 662 |
| 126 | N-[5-(11β-Fluoro-3,17β-dihydroxy-estra-1,3,5(10)-trien-7α-yl)-pentyl]-N-hexyl-naphth-2-yl-acetamide | 628 |
| 127 | N-[5-(11β-Fluoro-3,17β-dihydroxy-estra-1,3,5(10)-trien-7α-yl)-pentyl]-naphth-2-yl-N-octyl-acetamide | 656 |
| 128 | N-Cyclohexylmethyl-N-[5-(11β-fluoro-3,17β-dihydroxy-estra-1,3,5(10)-trien-7α-yl)-pentyl]-4-phenyl-butyramide | 618 |

| Example | Compound | MS (CI): [M]⁺ + 1 [m/z] |
|---|---|---|
| 129 | N-Benzyl-N-[5-(11β-fluoro-3,17β-dihydroxy-estra-1,3,5(10)-trien-7α-yl)-pentyl]-4-phenyl-butyramide | 612 |
| 130 | N-[5-(11β-Fluoro-3,17β-dihydroxy-estra-1,3,5(10)-trien-7α-yl)-pentyl]-N-(2-methoxy-ethyl)-4-phenyl-butyramide | 580 |
| 131 | N-[5-(11β-Fluoro-3,17β-dihydroxy-estra-1,3,5(10)-trien-7α-yl)-pentyl]-4-phenyl-N-(3-phenyl-propyl)-butyramide | 640 |
| 132 | N-[5-(11β-Fluoro-3,17β-dihydroxy-estra-1,3,5(10)-trien-7α-yl)-pentyl]-N-hexyl-4-phenyl-butyramide | 606 |
| 133 | N-[5-(11β-Fluoro-3,17β-dihydroxy-estra-1,3,5(10)-trien-7α-yl)-pentyl]-N-octyl-4-phenyl-butyramide | 634 |
| 134 | N-Cyclohexylmethyl-N-[5-(11β-fluoro-3,17β-dihydroxy-estra-1,3,5(10)-trien-7α-yl)-pentyl]-propionamide | 528 |
| 135 | N-Benzyl-N-[5-(11β-fluoro-3,17β-dihydroxy-estra-1,3,5(10)-trien-7α-yl)-pentyl]-propionamide | 522 |
| 136 | N-[5-(11β-Fluoro-3,17β-dihydroxy-estra-1,3,5(10)-trien-7α-yl)-pentyl]-N-(2-methoxy-ethyl)-propionamide | 490 |
| 137 | N-[5-(11β-Fluoro-3,17β13-dihydroxy-estra-1,3,5(10)-trien-7α-yl)-pentyl]-N-(3-phenyl-propyl)-propionamide | 550 |
| 138 | N-[5-(11β-Fluoro-3,17β-dihydroxy-estra-1,3,5(10)-trien-7α-yl)-pentyl]-N-hexyl-propionamide | 516 |
| 139 | N-[5-(11β-Fluoro-3,17β-dihydroxy-estra-1,3,5(10)-trien-7α-yl)-pentyl]-N-octyl-propionamide | 544 |
| 140 | 4-Biphenyl-N-cyclohexylmethyl-N-[5-(11β-fluoro-3,17β-dihydroxy-estra-1,3,5(10)-trien-7α-yl)-pentyl]-acetamide | 666 |
| 141 | 4-Biphenyl-N-benzyl-N-[5-(11β-fluoro-3,17β-dihydroxy-estra-1,3,5(10)-trien-7α-yl)-pentyl]-acetamide | 660 |
| 142 | 4-Biphenyl-N-[5-(11β-fluoro-3,17β-dihydroxy-estra-1,3,5(10)-trien-7α-yl)-pentyl]-N-(2-methoxy-ethyl)-acetamide | 628 |
| 143 | 4-Biphenyl-N-[5-(11β-fluoro-3,17β-dihydroxy-estra-1,3,5(10)-trien-7α-yl)-pentyl]-N-(3-phenyl-propyl)-acetamide | 688 |
| 144 | 4-Biphenyl-N-[5-(11β-fluoro-3,17β-dihydroxy-estra-1,3,5(10)-trien-7α-yl)-pentyl]-N-hexyl-acetamide | 654 |
| 145 | 4-Biphenyl-N-[5-(11β-fluoro-3,17β-dihydroxy-estra-1,3,5(10)-trien-7α-yl)-pentyl]-N-octyl-acetamide | 682 |
| 146 | 4-Acetylamino-N-cyclohexylmethyl-N-[6-(11β-fluoro-3,17β-dihydroxy-estra-1,3,5(10)-trien-7α-yl)-hexyl]-benzamide | 647 |
| 147 | 4-Acetylamino-N-benzyl-N-[6-(11β-fluoro-3,17β-dihydroxy-estra-1,3,5(10)-trien-7α-yl)-hexyl]-benzamide | 641 |
| 148 | 4-Acetylamino-N-[6-(11β-fluoro-3,17β-dihydroxy-estra-1,3,5(10)-trien-7α-yl)-hexyl]-N-(2-methoxy-ethyl)-benzamide | 609 |
| 149 | 4-Acetylamino-N-[6-(11β-fluoro-3,17β-dihydroxy-estra-1,3,5(10)-trien-7α-yl)-hexyl]-N-(3-phenyl-propyl)-benzamide | 669 |
| 150 | 4-Acetylamino-N-[6-(11β-fluoro-3,17β-dihydroxy-estra-1,3,5(10)-trien-7α-yl)-hexyl]-N-hexyl-benzamide | 635 |
| 151 | 4-Acetylamino-N-[6-(11β-fluoro-3,17β-dihydroxy-estra-1,3,5(10)-trien-7α-yl)-hexyl]-N-octyl-benzamide | 663 |
| 152 | 4-Cyano-N-cyclohexylmethyl-N-[6-(11β-fluoro-3,17β-dihydroxy-estra-1,3,5(10)-trien-7α-yl)-hexyl]-benzamide | 615 |
| 153 | N-Benzyl-4-cyano-N-[6-(11β-fluoro-3,17β-dihydroxy-estra-1,3,5(10)-trien-7α-yl)-hexyl]-benzamide | 609 |
| 154 | 4-Cyano-N-[6-(11β-fluoro-3,17β-dihydroxy-estra-1,3,5(10)-trien-7α-yl-hexyl]-N-(2-methoxy-ethyl)-benzamide | 577 |
| 155 | 4-Cyano-N-[6-(11β-fluoro-3,17β-dihydroxy-estra-1,3,5(10)-trien-7α-yl)-hexyl]-N-(3-phenyl-propyl)-benzamide | 637 |
| 156 | 4-Cyano-N-[6-(11β-fluoro-3,17β-dihydroxy-estra-1,3,5(10)-trien-7α-yl)-hexyl]-N-hexyl-benzamide | 603 |
| 157 | 4-Cyano-N-[6-(11β-fluoro-3,17β-dihydroxy-estra-1,3,5(10)-trien-7α-yl)-hexyl]-N-octyl-benzamide | 631 |
| 158 | 3-Cyclohexyl-N-cyclohexylmethyl-N-[6-(11β-fluoro-3,17β-dihydroxy-estra-1,3,5(10)-trien-7α-yl)-hexyl]-propionamide | 624 |
| 159 | N-Benzyl-3-cyclohexyl-N-[6-(11β-fluoro-3,17β-dihydroxy-estra-1,3,5(10)-trien-7α-yl)-hexyl]-propionamide | 618 |
| 160 | 3-Cyclohexyl-N-[6-(11β-fluoro-3,17β-dihydroxy-estra-1,3,5(10)-trien-7α-yl)-hexyl]-N-(2-methoxy-ethyl)-propionamide | 586 |
| 161 | 3-Cyclohexyl-N-[6-(11β-fluoro-3,17β-dihydroxy-estra-1,3,5(10)-trien-7α-yl)-hexyl]-N-(3-phenyl-propyl)-propionamide | 646 |
| 162 | 3-Cyclohexyl-N-[6-(11β-fluoro-3,17β-dihydroxy-estra-1,3,5(10)-trien-7α-yl)-hexyl]-N-hexyl-propionamide | 612 |
| 163 | 3-Cyclohexyl-N-[6-(11β-fluoro-3,17β-dihydroxy-estra-1,3,5(10)-trien-7α-yl)-hexyl]-N-octyl-propionamide | 640 |
| 164 | N-Cyclohexylmethyl-N-[6-(11β-fluoro-3,17β-dihydroxy-estra-1,3,5(10)-trien-7α-yl)-hexyl]-(3,4-dimethoxyphenyl)-acetamide | 664 |
| 165 | N-Benzyl-N-[6-(11β-fluoro-3,17β-dihydroxy-estra-1,3,5(10)-trien-7α-yl)-hexyl]-(3,4-dimethoxyphenyl)-acetamide | 658 |
| 166 | N-[6-(11β-Fluoro-3,17β-dihydroxy-estra-1,3,5(10)-trien-7α-yl)-hexyl]-N-(2-methoxy-ethyl)-(3,4-dimethoxyphenyl)-acetamide | 626 |
| 167 | N-[6-(11β-Fluoro-3,17β-dihydroxy-estra-1,3,5(10)-trien-7α-yl)-hexyl]-(3,dimethoxyphenyl)-N-(3-phenyl-propyl)-acetamide | 686 |
| 168 | N-[6-(11β-Fluoro-3,17β-dihydroxy-estra-1,3,5(10)-trien-7α-yl)-hexyl]-N-hexyl-(3,4-dimethoxyphenyl)-acetamide | 652 |
| 169 | N-[6-(11β-Fluoro-3,17β-dihydroxy-estra-1,3,5(10)-trien-7α-yl)-hexyl]-(3,dimethoxyphenyl)-N-octyl-acetamide | 680 |
| 170 | N-Cyclohexylmethyl-4-ethoxy-N-[6-(11β-fluoro-3,17β-dihydroxy-estra-1,3,5(10)-trien-7α-yl)-hexyl]-benzamide | 634 |
| 171 | N-Benzyl-4-ethoxy-N-[6-(11β-fluoro-3,17β-dihydroxy-estra-1,3,5(10)-trien-7α-yl)-hexyl]-benzamide | 628 |
| 172 | 4-Ethoxy-N-[6-(11β-fluoro-3,17β-dihydroxy-estra-1,3,5(10)-trien-7α-yl)-hexyl]-N-(2-methoxy-ethyl)-benzamide | 596 |
| 173 | 4-Ethoxy-N-[6-(11β-fluoro-3,17β-dihydroxy-estra-1,3,5(10)-trien-7α-yl)-hexyl]-N-(3-phenyl-propyl)-benzamide | 656 |
| 174 | 4-Ethoxy-N-[6-(11β-fluoro-3,17β-dihydroxy-estra-1,3,5(10)-trien-7α-yl)-hexyl]-N-hexyl-benzamide | 622 |
| 175 | 4-Ethoxy-N-[6-(11β-fluoro-3,17β-dihydroxy-estra-1,3,5(10)-trien-7α-yl)-hexyl]-N-octyl-benzamide | 650 |
| 176 | N-Cyclohexylmethyl-N-[6-(11β-fluoro-3,17β-dihydroxy-estra-1,3,5(10)-trien-7α-yl)-hexyl]-dodecanamide | 668 |
| 178 | N-Benzyl-N-[6-(11β-fluoro-3,17β-dihydroxy-estra-1,3,5(10)-trien-7α-yl)-hexyl]-dodecanamide | 662 |

-continued

| Example | Compound | MS (CI): [M]⁺ + 1 [m/z] |
|---|---|---|
| 179 | N-[6-(11β-Fluoro-3,17β-dihydroxy-estra-1,3,5(10)-trien-7α-yl)-hexyl]-N-(2-methoxy-ethyl)-dodecanamide | 630 |
| 180 | N-[6-(11β-Fluoro-3,17β-dihydroxy-estra-1,3,5(10)-trien-7α-yl)-hexyl]-N-(3-phenyl-propyl)-dodecanamide | 690 |
| 181 | N-[6-(11β-Fluoro-3,17β-dihydroxy-estra-1,3,5(10)-trien-7α-yl)-hexyl]-N-hexyl-dodecanamide | 656 |
| 182 | N-[6-(11β-Fluoro-3,17β-dihydroxy-estra-1,3,5(10)-trien-7α-yl)-hexyl]-N-octyl-dodecanamide | 685 |
| 183 | N-Cyclohexylmethyl-N-[6-(11β-fluoro-3,17β-dihydroxy-estra-1,3,5(10)-trien-7α-yl)-hexyl)-naphth-2-yl-acetamide | 654 |
| 184 | N-Benzyl-N-[6-(11β-fluoro-3,17β-dihydroxy-estra-1,3,5(10)-trien-7α-yl)-hexyl]-naphth-2-yl-acetamide | 648 |
| 185 | N-[6-(11β-Fluoro-3,17β-dihydroxy-estra-1,3,5(10)-trien-7α-yl)-hexyl]-N-(2-methoxy-ethyl)-naphth-2-yl-acetamide | 616 |
| 186 | N-[6-(11β-Fluoro-3,17β-dihydroxy-estra-1,3,5(10)-trien-7α-yl)-hexyl]-naphth-2-yl-N-(3-phenyl-propyl)-acetamide | 676 |
| 187 | N-[6-(11β-Fluoro-3,17β-dihydroxy-estra-1,3,5(10)-trien-7α-yl)-hexyl]-N-hexyl-naphth-2-yl-acetamide | 642 |
| 188 | N-[6-(11β-Fluoro-3,17β-dihydroxy-estra-1,3,5(10)-trien-7α-yl)-hexyl]-naphth-2-yl-N-octyl-acetamide | 670 |
| 189 | N-Cyclohexylmethyl-N-[6-(11β-fluoro-3,17β-dihydroxy-estra-1,3,5(10)-trien-7α-yl)-hexyl]-4-phenyl-butyramide | 632 |
| 190 | N-Benzyl-N-[6-(11β-fluoro-3,17β-dihydroxy-estra-1,3,5(10)-trien-7α-yl)-hexyl]-4-phenyl-butyramide | 626 |
| 191 | N-[6-(11β-Fluoro-3,17β-dihydroxy-estra-1,3,5(10)-trien-7α-yl)-hexyl]-N-(2-methoxy-ethyl)-4-phenyl-butyramide | 594 |
| 192 | N-[6-(11β-Fluoro-3,17β-dihydroxy-estra-1,3,5(10)-trien-7α-yl)-hexyl]-4-phenyl-N-(3-phenyl-propyl)-butyramide | 654 |
| 193 | N-[6-(11β-Fluoro-3,17β-dihydroxy-estra-1,3,5(10)-trien-7α-yl)-hexyl]-N-hexyl-4-phenyl-butyramide | 620 |
| 194 | N-[6-(11β-Fluoro-3,17β-dihydroxy-estra-1,3,5(10)-trien-7α-yl)-hexyl]-N-octyl-4-phenyl-butyramide | 648 |
| 195 | N-Cyclohexylmethyl-N-[6-(11β-fluoro-3,17β-dihydroxy-estra-1,3,5(10)-trien-7α-yl)-hexyl]-propionamide | 542 |
| 196 | N-Benzyl-N-[6-(11β-fluoro-3,17β-dihydroxy-estra-1,3,5(10)-trien-7α-yl)-hexyl]-propionamide | 536 |
| 197 | N-[6-(11β-Fluoro-3,17β-dihydroxy-estra-1,3,5(10)-trien-7α-yl)-hexyl]-N-(2-methoxy-ethyl)-propionamide | 504 |
| 198 | N-[6-(11β-Fluoro-3,17β-dihydroxy-estra-1,3,5(10)-trien-7α-yl)-hexyl]-N-(3-phenyl-propyl)-propionamide | 564 |
| 199 | N-[6-(11β-Fluoro-3,17β-dihydroxy-estra-1,3,5(10)-trien-7α-yl)-hexyl]-N-hexyl-propionamide | 530 |
| 200 | N-[6-(11β-Fluoro-3,17β-dihydroxy-estra-1,3,5(10)-trien-7α-yl)-hexyl]-N-octyl-propionamide | 558 |
| 201 | 4-Biphenyl-N-cyclohexylmethyl-N-[6-(11β-fluoro-3,17β-dihydroxy-estra-1,3,5(10)-trien-7α-yl)-hexyl]-acetamide | 680 |
| 202 | 4-Biphenyl-N-benzyl-N-[6-(11β-fluoro-3,17β-dihydroxy-estra-1,3,5(10)-trien-7α-yl)-hexyl]-acetamide | 674 |
| 203 | 4-Biphenyl-N-[6-(11β-fluoro-3,17β-dihydroxy-estra-1,3,5(10)-trien-7α-yl)-hexyl]-N-(2-methoxy-ethyl)-acetamide | 642 |
| 204 | 4-Biphenyl-N-[6-(11β-fluoro-3,17β-dihydroxy-estra-1,3,5(10)-trien-7α-yl)-hexyl]-N-(3-phenyl-propyl)-acetamide | 702 |
| 205 | 4-Biphenyl-N-[6-(11β-fluoro-3,17β-dihydroxy-estra-1,3,5(10)-trien-7α-yl)-hexyl]-N-hexyl-acetamide | 668 |
| 206 | 4-Biphenyl-N-[6-(11β-fluoro-3,17β-dihydroxy-estra-1,3,5(10)-trien-7α-yl)-hexyl]-N-octyl-acetamide | 696 |

What is claimed is:

1. A 11β-Halogen-7α-substituted estratriene of formula I

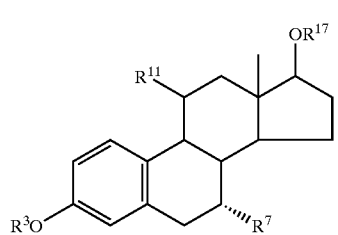

wherein $R^3$ is a hydrogen atom, a hydrocarbon radical with up to 8 carbon atoms, or a radical of partial formula $R^{3'}$—C(O)—, $R^{3'}$ is a hydrogen atom or a hydrocarbon radical with up to 8 carbon atoms or a phenyl radical, $R^{11}$ is a fluorine or chlorine atom, $R^{17}$ is a hydrogen atom or a radical of partial formula $R^{17'}$—C(O)—, $R^{17'}$ is a hydrogen atom or a hydrocarbon radical with up to 8 carbon atoms, $R^7$ is a radical of formula —A—B—Z—$R^{20}$, A is a direct bond, a phenylene radical, or a benzylidene radical, whereby the methylene group is bonded to the 7-carbon atom of the base steroid structure, B is a straight-chain or branched-chain alkylene, alkenylene or alkinylene group with 3 to 14 carbon atoms, and Z is —$NR^{21}$—, —$SO_x$, or —$NR^{31}$, when Z is —$NR^{21}$—, $R^{21}$ is a $C_1$–$C_3$ alkyl group, $R^{20}$ is a hydrogen atom, a straight-chain or branched-chain alkyl, alkenyl or alkinyl group with up to 10 carbon atoms or one of groupings: —D—$C_nF_{2n+1}$, —L—CH=CF—$C_pF_{2p+1}$, —D—O—$(CH_2)_q$-aryl, —D—O—$(CH_2)_r$—$C_nF_{2n+1}$, or $R^{20}$ and $R^{21}$ with the nitrogen atom to which they are bonded form a saturated or unsaturated heterocycle with 5 or 6 chain links, which optionally contains one or two additional heteroatoms, selected from nitrogen, oxygen and sulfur, and optionally is substituted, D is a straight-chain or branched-chain alkylene, alkenylene or alkinylene group with up to 8 carbon atoms n is an integer from 1 to 8, L is a straight-chain or branched-chain alkylene, alkenylene or alkinylene group with 2 to 7 carbon atoms, p is an integer from 2 to 7, q is 0, 1, 2 or 3,
aryl stands for a phenyl radical, 1- or 2-naphthyl radical or a heteroaryl radical that is optionally substituted in one or two places,
r is an integer from 1 to 5, or
when Z is —$SO_x$
  x is for 0, 1 or 2,
  $R^{20}$ is a straight-chain or branched-chain alkyl, alkenyl or alkinyl group with up to 10 carbon atoms, or one of groupings: —D—$C_nF_{2n+1}$, —L—CH=CF—$C_pF_{2p+1}$, —D—O—$(CH_2)_q$-aryl, —D—O—$(CH_2)_r$—$C_nF_{2n+1}$,
  D is a straight-chain or branched-chain alkylene, alkenylene or alkinylene group with up to 8 carbon atoms
  n is an integer from 1 to 8,
  L is a straight-chain or branched-chain alkylene, alkenylene or alkinylene group with 2 to 7 carbon atoms,
  p is an integer from 2 to 7,
  q is 0, 1, 2 or 3,
  aryl stands for a phenyl radical, 1- or 2-naphthyl radical or a heteroaryl radical optionally substituted in one or two places, and
  r stands for an integer from 1 to 5,
when Z is —$NR^{31}$,
  $R^{20}$ is a straight-chain or branched-chain alkyl, alkenyl or alkinyl radical with up to 14 carbon atoms, which can be interrupted and/or partially fluorinated by one to three heteroatoms —O— and —S— and groupings —$NR^{32}$—,
  $R^{32}$ is a hydrogen atom or a $C_1$–$C_3$ alkyl radical, an aryl or heteroaryl radical that is optionally substituted in one or two places, a $C_3$–$C_{10}$ cycloalkyl radical that is optionally substituted in one or two places, a $C_4$–$C_{15}$ cycloalkylalkyl radical that is optionally substituted in one or two places, a $C_7$–$C_{20}$ aralkyl radical that is optionally substituted in one or two places, a heteroaryl-$C_1$–$C_6$ alkyl radical that is optionally substituted in one or two places or an optionally substituted aminoalkyl radical,
  $R^{31}$ is a radical of formula —C(O)$R^{33}$ or —$CH_2$—$R^{33}$, and
  $R^{33}$ is a straight-chain or branched-chain, alkyl, alkenyl or alkinyl radical with up to 14 carbon atoms, which can be interrupted and/or partially fluorinated by one to three heteroatoms —O— and —S— and groupings —$NR^{32}$—, in which $R^{32}$ is a hydrogen atom or a $C_1$–$C_3$ alkyl radical, an aryl or heteroaryl radical that is optionally substituted in one or two places, a $C_3$–$C_{10}$ cycloalkyl radical that is optionally substituted in one or two places, a $C_4$–$C_{15}$ cycloalkylalkyl radical that is optionally substituted in one or two places, a $C_7$–$C_{20}$ aralkyl radical that is optionally substituted in one or two places, a heteroaryl-$C_1$–$C_6$ alkyl radical that is optionally substituted in one or two places, an optionally substituted aminoalkyl radical or a biphenylene radical,
excluding the compounds:
  11β-fluoro-7α-{5-[N-methyl-N-3-(4,4,5,5,5-pentafluoropentylthio)-propylamino]-pentyl}-estra-1,3,5(10)-triene-3,17β-diol
  11β-fluoro-7α-{5-[2-(4,4,5,5,5-pentafluoropentylthio)-pyrrolidin-1-yl]-pentyl}-estra-1,3,5(10)-triene-3,17β-diol
  11β-fluoro-7α-{6-[N-methyl-N-3-(4,4,5,5,5-pentafluoropentylthio)-propylamino]-hexyl}-estra-1,3,5(10)-triene-3,17β-diol
  11β-fluoro-7α-{5-[(2S)-2-(4-trifluoromethylphenyl-thiomethyl)-pyrrolidin-1-yl]-pentyl}-estra-1,3,5(10)-triene-3,17β-diol
  11β-fluoro-7α-{5-[(2S)-2-(4,4,5,5,5-pentafluoropentyl-thiomethyl)-pyrrolidin-1-yl]-pentyl)-estra-1,3,5(10)-triene-3,17β-diol
  11β-fluoro-7α-{5-[(2S)-2-(4,4,5,5,5-pentafluoropentane-sulfinylmethyl)-pyrrolidin-1-yl]-pentyl}-estra-1,3,5(10)-triene-3,17β-diol
  11β-fluoro-7α-{5-[(2S)-2-(4,4,5,5,5-pentafluoropentane-sulfonylmethyl)-pyrrolidin-1-yl]-pentyl}-estra-1,3,5(10)-triene-3,17β-diol.

2. A 11β-Halogen-7α-substituted estratriene according to claim 1, in which $R^3$ is a hydrogen atom.

3. A 11β-Halogen-7α-substituted estratriene according to claim 1, in which $R^3$ is a benzoyl radical.

4. A 11β-Halogen-7α-substituted estratriene according to claim 1, in which $R^{11}$ is a fluorine atom.

5. A 11β-Halogen-7α-substituted estratriene according to claim 1, in which $R^{17}$ is a hydrogen atom.

6. A 11β-Halogen-7α-substituted estratriene according to claim 1, in which A is a direct bond.

7. A 11β-Halogen-7α-substituted estratriene according to claim 6, in which $R^7$ is a radical of formula —$(CH_2)_s$—Z—$R^{20}$,
  s is an integer from 3 to 8,
  Z is —$NR^{21}$,
  $R^{21}$ stands for a $C_1$–$C_3$ alkyl group,
  $R^{20}$ means a hydrogen atom, a $C_1$–$C_9$ alkyl group, or one of the groupings:
    —$(CH_2)_m$—$C_nF_{2n+1}$, whereby m and n, independently of one another, in each case is an integer from 1 to 8,
    —$(CH_2)_o$—CH=CF—$C_pF_{2p+1}$, whereby o is 1, 2 or 3 and p is an integer from 2 to 7,
    —$(CH_2)_m$—O—$(CH_2)_q$-aryl, whereby m has the already indicated meaning, q is 0, 1, 2 or 3 and aryl stands for a phenyl or heteroaryl radical that is optionally substituted in one or two places, or
    —$(CH_2)_m$—O—$(CH_2)_r$—$C_nF_{2n+1}$, whereby m and n have the already indicated meanings and r stands for an integer from 1 to 5.

8. A 11β-Halogen-7α-substituted estratriene according to claim 6, in which $R^7$ is
a radical of formula —$(CH_2)_s$—Z—$R^{20}$,
  s is an integer from 3 to 8,
  Z stands for —$NR^{21}$,
  $R^{20}$ is a hydrogen atom, a straight-chain or branched-chain alkyl, alkenyl or alkinyl group with up to 10 carbon atoms or one of groupings: —D—$C_nF_{2n+1}$, —L—CH=CF—$C_pF_{2p+1}$, —D—O—$(CH_2)_q$-aryl, —D—O—$(CH_2)_r$—$C_nF_{2n+1}$,
  $R^{21}$ stands for a $C_1$–$C_3$ alkyl group, or
  $R^{20}$ and $R^{21}$ with the nitrogen atom, to which they are bonded, form a saturated or unsaturated heterocycle with 5 or 6 chain links, which optionally contains one or two additional heteroatoms, selected from nitrogen, oxygen and sulfur, and optionally is substituted.

9. A 11β-Halogen-7α-substituted estratriene according to claim 6, in which $R^7$ is
a radical of formula —$(CH_2)_s$—Z—$R^{20}$,
  s is an integer from 3 to 8,
  Z stands for —$SO_x$—,
  x stands for 0, 1 or 2,
  $R^{20}$ means —$(CH_2)_m$—O—$(CH_2)_r$—$C_nF_{2n+1}$, whereby m and n have the already indicated meanings and r stands for an integer from 1 to 5.

10. A 11β-Halogen-7α-substituted estratriene according to claim 1, in which $R^7$ is selected from the group of the following side chains.

11. A compound of claim 14, wherein said compound is selected from

11β-Fluoro-7α-{5-[methyl-(8,8,9,9,9-pentafluoro-nonyl)-amino]-pentyl}-estra-1,3,5(10)-triene-3,17β-diol;

11β-Fluoro-7α-{5-[methyl-nonyl-amino]-pentyl}-estra-1,3,5(10)-triene-3,17β-diol;

11β-Fluoro-7α-{5-[methyl-(9,9,10,10,10-pentafluoro-decyl)-amino]-pentyl}-estra-1,3,5(10)-triene-3,17β-diol;

11β-Fluoro-7α-{6-[methyl-(8,8,9,9,9-pentafluoro-nonyl)-amino]-hexyl}-estra-1,3,5(10)-triene-3,17β-diol;

11β-Fluoro-7α-{6-[methyl-(9,9,10,10,10-pentafluoro-decyl)-amino]-hexyl}-estra-1,3,5(10)-triene-3,17β-diol;

11β-Fluoro-7α-(5-(methyl-amino)-pentyl)-estra-1,3,5(10)-triene-3,17β-diol;

11β-Fluoro-7α-(5-pyrrolidin-1-yl-pentyl)-estra-1,3,5(10)-triene-3,17β-diol;

11β-Fluoro-7α-{5-[methyl-(4,4,5,5,5-pentafluoro-pentyl)-amino]-pentyl}-estra-1,3,5(10)-triene-3,17β-diol;

11β-Fluoro-7α-{5-[methyl-(4,4,5,5,6,6,7,7,8,8,9,9,9-tridecafluoro-nonyl)-amino]-pentyl}-estra-1,3,5(10)-triene-3,17β-diol;

11β-Fluoro-7α-{5-[(4,4,5,5,6,6,7,7.8,8,9,9,10,10,11,11,11-heptadecafluor-undecyl)-methyl-amino]-pentyl}-estra-1,3,5(10)-triene-3,17β-diol;

11β-Fluoro-7α-{5-[methyl-(3,3,4,4,5,5,6,6,6-nonafluoro-hexyl)-amino]-pentyl}-estra-1,3,5(10)-triene-3,17β-diol;

11β-Fluoro-7α-{5-[methyl-(7,7,8,8,8-pentafluor-octyl)-amino]-pentyl}-estra-1,3,5(10)-triene-3,17β-diol;

11β-Fluoro-7α-{6-[methyl-(7,7,8,8,8-pentafluor-octyl)-amino]-hexyl}-estra-1,3,5(10)-triene-3,17β-diol;

11β-Fluoro-7α-{5-(methyl-(7,7,8,8,9,9,10,10,10-nonafluoro-decyl)-amino]-pentyl}-estra-1,3,5(10)-triene-3,17β-diol;

11β-Fluoro-7α-{5-[methyl-(7,7,8,8,9,9,10,10,11,11,12,12,12-tridecafluoro-dodecyl)-amino]-pentyl}-estra-1,3.5(10)-triene-3,17β-diol;

11β-Fluoro-7α-{5-[(7,7,8,8,9,9,10,10,11,11,12,12,13,13,14,14,14-heptadecafluoro-tetradecyl)-methyl-amino]-pentyl}-estra-1,3,5(10)-triene-3,17β-diol;

11β-Fluoro-7α-{5-[(3,4,4,5,5,5-hexafluoro-pent-2-enyl)-methyl-amino]-pentyl}-estra-1,3,5(10)-triene-3,17β-diol;

7α-{5-[(3,4,4,5,5,6,6,7,7,8,8-Dodecafluor-oct-2-enyl)-methyl-amino]-pentyl}-11β-fluor-estra-1,3,5(10)-triene-3,17β-diol;

11β-Fluoro-7α-{5-[(3,4,4,5,5,6,6,7,7,8,8,9,9,10,10,10-hexadecafluoro-dec-2-enyl)-methyl-amino]-pentyl}-estra-1,3,5(10)-triene-3,17β-diol;

11β-Fluoro-7α-{5-[methyl-(3-phenoxy-propyl)-amino]-pentyl}-estra-1,3,5(10)-triene-3,17β-diol;

7α-{5-[(3-Benzyloxy-propyl)-methyl-amino]-pentyl}-11β-fluor-estra-1,3,5(10)-triene-3,17β-diol;

11β-Fluoro-7α-{5-[N-methyl-N-3-(4,4,5,5,5-pentafluoropentyloxy)-propylamino]-pentyl}-estra-1,3,5(10)-triene-3,17β-diol;

11β-Fluoro-7α-[9-(4,4,5,5,5-pentafluoropentylsulfinyl)-nonyl]-estra-1,3,5(10)-triene-3,17β-diol;

N-[4-(11β-Fluoro-3,17-dihydroxy-estra-1,3,5(10)-trien-7α-yl)-butyl]-N-pentyl-benzamide;

4-Acetylamino-N-cyclohexylmethyl-N-[4-(11β-fluoro-3,17β-dihydroxy-estra-1,3,5(10)-trien-7α-yl)-butyl]-benzamide;

4-Acetylamino-N-benzyl-N-[4-(11β-fluoro-3,17β-dihydroxy-estra-1,3,5(10)-trien-7α-yl)-butyl]-benzamide;

4-Acetylamino-N-[4-(11β-fluoro-3,17β-dihydroxy-estra-1,3,5(10)-trien-7α-yl)-butyl]-N-(2-methoxy-ethyl)-benzamide;

4-Acetylamino-N-[4-(11β-fluoro-3,17β-dihydroxy-estra-1,3,5(10)-trien-7α-yl)-butyl]-N-(3-phenyl-propyl)-benzamide;

4-Acetylamino-N-[4-(11β-fluoro-3,17β-dihydroxy-estra-1,3,5(10)-trien-7α-yl)-butyl]-N-hexyl-benzamide;

4-Acetylamino-N-[4-(11β-fluoro-3,17β-dihydroxy-estra-1,3,5(10)-trien-7α-yl)-butyl]-N-octyl-benzamide;

4-Cyano-N-cyclohexylmethyl-N-[4-(11β-fluoro-3,17β-dihydroxy-estra-1,3,5(10)-trien-7α-yl)-butyl]-benzamide;

N-Benzyl-4-cyano-N-[4-(11β-fluoro-3,17β-dihydroxy-estra-1,3,5(10)-trien-7α-yl)-butyl]-benzamide;

4-Cyano-N-[4-(11β-fluoro-3,17β-dihydroxy-estra-1,3,5(10)-trien-7α-yl)-butyl]-N-(2-methoxy-ethyl)-benzamide;

4-Cyano-N-[4-(11β-fluoro-3,17β-dihydroxy-estra-1,3,5(10)-trien-7-yl)-butyl]-N-(3-phenyl-propyl)-benzamide;

4-Cyano-N-[4-(1-fluoro-3,17β-dihydroxy-estra-1,3,5(10)-trien-7α-yl)-butyl]-N-hexyl-benzamide;

4-Cyano-N-[4-(11β-fluoro-3,17β-dihydroxy-estra-1,3,5(10)-trien-7α-yl)-butyl]-N-octyl-benzamide;

3-Cyclohexyl-N-cyclohexylmethyl-N-[4-(11β-fluoro-3,17β-dihydroxy-estra-1,3,5(1,0)-trien-7α-yl)-butyl]-propionamide;

N-Benzyl-3-cyclohexyl-N-[4-(11β-fluoro-3,17β-dihydroxy-estra-1,3,5(10)-trien-7α-yl)-butyl]-propionamide;

3-Cyclohexyl-N-[4-(11β-fluoro-3,17β-dihydroxy-estra-1,3,5(10)-trien-7α-yl)-butyl]-N-(2-methoxy-ethyl)-propionamide;

3-Cyclohexyl-N-[4-(11β-fluoro-3,17β-dihydroxy-estra-1,3,5,(10)-trien-7α-yl)-butyl]-N-(3-phenyl-propyl)-propionamide;

3-Cyclohexyl-N-[4-(11β-fluoro-3,17β-dihydroxy-estra-1,3,5(10)-trien-7α-yl)-butyl]-N-hexyl-propionamide;

3-Cyclohexyl-N-[4-(11β-fluoro-3,17β-dihydroxy-estra-1,3,5(10)-trien-7α-yl)-butyl]-N-octyl-propionamide;

N-Cyclohexylmethyl-N-[4-(11β-fluoro-3,17β-dihydroxy-estra-1,3,5(10)-trien-7α-yl)-butyl]-(3,4-dimethoxyphenyl)-acetamide;

N-Benzyl-N-[4-(11β-fluoro-3,17β-dihydroxy-estra-1,3,5(10)-trien-7α-yl)-butyl]-(3,4-dimethoxyphenyl)-acetamide;

N-[4-(11β-Fluoro-3,17β-dihydroxy-estra-1,3,5(10)-trien-7α-yl)-butyl]-N-(2-methoxy-ethyl)-(3,4-dimethoxyphenyl)-acetamide;

N-[4-(11β-Fluoro-3,17β-dihydroxy-estra-1,3,5(10)-trien-7α-yl)-butyl]-(3,4-dimethoxyphenyl)-N-(3-phenyl-propyl)-acetamide;

N-[4-(11β-Fluoro-3,17β-dihydroxy-estra-1,3,5(10)-trien-7α-yl)-butyl]-N-hexyl-(3,4-dimethoxyphenyl)-acetamide;

N-[4-(11β-Fluoro-3,17β-dihydroxy-estra-1,3,5(10)-trien-7α-yl)-butyl]-(3,4-dimethoxyphenyl)-N-octyl-acetamide;

N-Cyclohexylmethyl-4-ethoxy-N-[4-(11β-fluoro-3,17β-dihydroxy-estra-1,3,5(10)-trien-7α-yl)-butyl]-benzamide;

N-Benzyl-4-ethoxy-N-[4-(11β-fluoro-3,17β-dihydroxy-estra-1,3,5-trien-7α-yl)-butyl]-benzamide;

4-Ethoxy-N-[4-(11β-fluoro-3,17β-dihydroxy-estra-1,3,5(10)-trien-7α-yl)-butyl]-N-(2-methoxy-ethyl)-benzamide;

4-Ethoxy-N-[4-(11β-fluoro-3,17β-dihydroxy-estra-1,3,5(10)-trien-7α-yl)-butyl]-N-(3-phenyl-propyl)-benzamide;

4-Ethoxy-N-[4-(11β-fluoro-3,17β-dihydroxy-estra-1,3,5(10)-trien-7α-yl)-butyl]-N-hexyl-benzamide;

4-Ethoxy-N-[4-(11β-fluoro-3,17β-dihydroxy-estra-1,3,5(10)-trien-7α-yl)-butyl]-N-octyl-benzamide;

N-Cyclohexylmethyl-N-[4-(11β-fluoro-3,17β-dihydroxy-estra-1,3,5(10)-trien-7α-yl)-butyl]-dodecanamide;

N-Benzyl-N-[4-(11β-fluoro-3,17β-dihydroxy-estra-1,3,5(10)-trien-7α-yl)-butyl]-dodecanamide;

N-[4-(11β-Fluoro-3,17β-dihydroxy-estra-1,3,5(10)-trien-7α-yl)-butyl]-N-(2-methoxy-ethyl)-dodecanamide;

N-[4-(11β-fluoro-3,17β-dihydroxy-estra-1,3,5(10)-trien-7α-yl)-butyl]-N-(3-phenyl-propyl)-dodecanamide;

N-[4-(11β-Fluoro-3,17β-dihydroxy-estra-1,3,5(10)-trien-7α-yll)-butl]-N-hexyl-dodecanamide;

N-[4-(11β-Fluoro-3,17β-dihydroxy-estra-1,3,5(10)-trien-7α-yl)-butyl]-N-octyl-dodecanamide;

N-Cyclohexylmethyl-N-[4-(11β-fluoro-3,17β-dihydroxy-estra-1,3,5(10)-trien-7α-yl)-butyl]-naphth-2-yl-acetamide;

N-Benzyl-N-[4-(11β-fluoro-3,17β-dihydroxy-estra-1,3,5(10)-trien-7α-yl)-butyl]-naphth-2-yl-acetamide;

N-[4-(11β-Fluoro-3,17β-dihydroxy-estra-1,3,5(10)-trien-7α-yl)-butyl]-N-(2-methoxy-ethyl)-naphth-2-yl-acetamide;

N-[4-(11β-Fluoro-3,17β-dihydroxy-estra-1,3,5(10)-trien-7α-yl)-butyl]-naphth-2-yl-N-(3-phenyl-propyl)-acetamide;

N-[4-(11β-Fluoro-3,17β-dihydroxy-estra-1,3,5(10)-trien-7α-yl)-butyl]-N-hexyl-naphth-2-yl-acetamide;

N-[4-(11β-Fluoro-3,17β-dihydroxy-estra-1,3,5(10)-trien-7α-yl)-butyl]-naphth-2-yl-N-octyl-acetamide;

N-Cyclohexylmethyl-N-[4-(11β-fluoro-3,17β-dihydroxy-estra-1,3,5(10)-trien-7α-yl)-butyl]-4-phenyl-butyramide;

N-Benzyl-N-[4-(11β-fluoro-3,17β-dihydroxy-estra-1,3,5(10)-trien-7α-yl)-butyl]-4-phenyl-butyramide;

N-[4-(11β-Fluoro-3,17β-dihydroxy-estra-1,3,5(10)-trien-7α-yl)-butyl]-N-(2-methoxy-ethyl)-4-phenyl-butyramide;

N-[4-(11β-Fluoro-3,17β-dihydroxy-estra-1,3,5(10)-trien-7α-yl)-butyl]-4-phenyl-N-(3-phenyl-propyl)-butyramide;

N-[4-(11β-Fluoro-3,17β-dihydroxy-estra-1,3,5(10)-trien-7α-yl)-butyl]-N-hexyl-4-phenyl-butyramide;

N-[4-(11β-Fluoro-3,17β-dihydroxy-estra-1,3,5(10)-trien-7α-yl)-butyl]-N-octyl-4-phenyl-butyramide;

N-Cyclohexylmethyl-N-[4-(11β-fluoro-3,17β-dihydroxy-estra-1,3,5(10)-trien-7α-yl)-butyl]-propionamide;

N-Benzyl-N-[4-(11β-fluoro-3,17β-dihydroxy-estra-1,3,5(10)-trien-7α-yl)-butyl]-propionamide;

N-[4-(11β-Fluoro-3,17β-dihydroxy-estra-1,3,5(10)-trien-7α-yl)-butyl]-N-(2-methoxy-ethyl)-propionamide;

N-[4-(11β-Fluoro-3,17β-dihydroxy-estra-1,3,5(10)-trien-7α-yl)-butyl]-N-(3-phenyl-propyl)-propionamide;

N-[4-(11β-Fluoro-3,17β-dihydroxy-estra-1,3,5(10)-trien-7α-yl)-butyl]-N-hexyl-propionamide;

N-[4-(11β-Fluoro-3,17β-dihydroxy-estra-1,3,5(10)-trien-7α-yl)-butyl]-N-octyl-propionamide;

4-Biphenyl-N-cyclohexylmethyl-N-[4-(11β-fluoro-3,17β-dihydroxy-estra-1,3,5(10)-trien-7α-yl)-butyl]-acetamide;

4-Biphenyl-N-benzyl-N-[4-(11β-fluoro-3,17β-dihydroxy-estra-1,3,5(10)-trien-7α-yl)-butyl]-acetamide;

4-Biphenyl-N-[4-(11β-fluoro-3,17β-dihydroxy-estra-1,3,5(10)-trien-7α-yl)-butyl]-N-(2-methoxy-ethyl)-acetamide;

4-Biphenyl-N-[4-(11β-fluoro-3,17β-dihydroxy-estra-1,3,5(10)-trien-7α-yl)-butyl]-N-(3-phenyl-propyl)-acetamide;

4-Biphenyl-N-[4-(11β-fluoro-3,17β-dihydroxy-estra-1,3,5(10)-trien-7α-yl)-butyl]-N-hexyl-acetamide;

4-Biphenyl-N-[4-(11β-fluoro-3,17β-dihydroxy-estra-1,3,5(10)-trien-7α-yl)-butyl]-N-octyl-acetamide;

4-Acetylamino-N-cyclohexylmethyl-N-[5-(11β-fluoro-3,17β-dihydroxy-estra-1,3,5(10)-trien-7α-yl)-pentyl]-benzamide;

4-Acetylamino-N-benzyl-N-[5-(11β-fluoro-3,17β-dihydroxy-estra-1,3,5(10)-trien-7α-yl)-pentyl]-benzamide;

4-Acetylamino-N-[5-(11β-fluoro-3,17β-dihydroxy-estra-1,3,5(10)-trien-7α-yl)-pentyl]-N-(2-methoxy-ethyl)-benzamide;

4-Acetylamino-N-[5-(11β-fluoro-3,17β-dihydroxy-estra-1,3,5(10)-trien-7α-yl)-pentyl]-N-(3-phenyl-propyl)-benzamide;

4-Acetylamino-N-[5-(11β-fluoro-3,17β-dihydroxy-estra-1,3,5(10)-trien-7α-yl)-pentyl]-N-hexyl-benzamide;

4-Acetylamino-N-[5-(11β-fluoro-3,17β-dihydroxy-estra-1,3,5(10)-trien-7α-yl)-pentyl]-N-octyl-benzamide;

4-Cyano-N-cyclohexylmethyl-N-[5-(11β-fluoro-3,17β-dihydroxy-estra-1,3,5(10)-trien-7α-yl)-pentyl]-benzamide;

N-Benzyl-4-cyano-N-[5-(11β-fluoro-3,17β-dihydroxy-estra-1,3,5(10)-trien-7α-yl)-pentyl]-benzamide;

4-Cyano-N-[5-(11β-fluoro-3,17β-dihydroxy-estra-1,3,5(10)-trien-7α-yl)-pentyl]-N-(2-methoxy-ethyl)-benzamide;

4-Cyano-N-[5-(11β-fluoro-3,17β-dihydroxy-estra-1,3,5(10)-trien-7α-yl)-pentyl]-N-(3-phenyl-propyl)-benzamide;

4-Cyano-N-[5-(11β-fluoro-3,17β-dihydroxy-estra-1,3,5(10)-trien-7α-yl)-pentyl]-N-hexyl-benzamide;

4-Cyano-N-[5-(11β-fluoro-3,17β-dihydroxy-estra-1,3,5(10)-trien-7α-yl)-pentyl]-N-octyl-benzamide;

3-Cyclohexyl-N-cyclohexylmethyl-N-[5-(11β-fluoro-3,17β-dihydroxy-estra-1,3,5(10)-trien-7α-yl)-pentyl]-propionamide;

N-Benzyl-3-cyclohexyl-N-[5-(11β-fluoro-3,17β-dihydroxy-estra-1,3,5(10)-trien-7α-yl)-pentyl]-propionamide;

3-Cyclohexyl-N-[5-(11β-fluoro-3,17β-dihydroxy-estra-1,3,5(10)-trien-7α-yl)-pentyl]-N-(2-methoxy-ethyl)-propionamide;

3-Cyclohexyl-N-[5-(11β-fluoro-3,17β-dihydroxy-estra-1,3,5(10)-trien-7α-yl)-pentyl]-N-(3-phenyl-propyl)-propionamide;

3-Cyclohexyl-N-[5-(11β-fluoro-3,17β-dihydroxy-estra-1,3,5(10)-trien-7α-yl)-pentyl]-N-hexyl-propionamide;

3-Cyclohexyl-N-[5-(11β-fluoro-3,17β-dihydroxy-estra-1,3,5(10)-trien-7α-yl)-pentyl]-N-octyl-propionamide;

N-Cyclohexylmethyl-N-[5-(11β-fluoro-3,17β-dihydroxy-estra-1,3,5(10)-trien-7α-yl)-pentyl]-(3,4-dimethoxyphenyl)-acetamide;

N-Benzyl-N-[5-(11β-fluoro-3,17β-dihydroxy-estra-1,3,5(10)-trien-7α-yl)-pentyl]-(3,4-dimethoxyphenyl)-acetamide;

N-[5-(11β-Fluoro-3,17β-dihydroxy-estra-1,3,5(10)-trien-7α-yl)-pentyl]-N-(2-methoxy-ethyl)-(3,4-dimethoxyphenyl)-acetamide;

N-[5-(11β-Fluoro-3,17β-dihydroxy-estra-1,3,5(10)-trien-7α-yl)-pentyl]-(3,4-dimethoxyphenyl)-N-(3-phenyl-propyl)-acetamide;

N-[5-(11β-Fluoro-3,17β-dihydroxy-estra-1,3,5(10)-trien-7α-yl)-pentyl]-N-hexyl-(3,4-dimethoxyphenyl)-acetamide;

N-[5-(11β-Fluoro-3,17β-dihydroxy-estra-1,3,5(10)-trien-7α-yl)-pentyl]-(3,4-dimethoxyphenyl)-N-octyl-acetamide;

N-Cyclohexylmethyl-4-ethoxy-N-[5-(11β-fluoro-3,17β-dihydroxy-estra-1,3,5(10)-trien-7α-yl)-pentyl]-benzamide;

N-Benzyl-4-ethoxy-N-[5-(11β-fluoro-3,17β-dihydroxy-estra-1,3,5(10)-trien-7α-yl)-pentyl]-benzamide;

4-Ethoxy-N-[5-(11β-fluoro-3,17β-dihydroxy-estra-1,3,5(10)-trien-7α-yl)-pentyl]-N-(2-methoxy-ethyl)-benzamide;

4-Ethoxy-N-[5-(11β-fluoro-3,17β-dihydroxy-estra-1,3,5(10)-trien-7α-yl)-pentyl]-N-(3-phenyl-propyl)-benzamide;

4-Ethoxy-N-[5-(11β-fluoro-3,17β-dihydroxy-estra-1,3,5(10)-trien-7α-yl)-pentyl]-N-hexyl-benzamide;

4-Ethoxy-N-[5-(11β-fluoro-3,17β-dihydroxy-estra-1,3,5(10)-trien-7α-yl)-pentyl]-N-octyl-benzamide;

N-Cyclohexylmethyl-N-[5-(11β-fluoro-3,17β-dihydroxy-estra-1 35(10)-trien-7α-yl)-pentyl]-dodecanamide;

N-Benzyl-N-[5-(11β-fluoro-3,17β-dihydroxy-estra-1,3,5(10)-trien-7α-yl)-pentyl]-dodecanamide;

N-[5-(11β-Fluoro-3,17β-dihydroxy-estra-1,3,5(10)-trien-7α-yl)-pentyl]-N-(2-methoxy-ethyl)-dodecanamide;

N-[5-(11β-Fluoro-3,17β-dihydroxy-estra-1,3,5(10)-trien-7α-yl)-pentyl]-N-(3-phenyl-propyl)-dodecanamide;

N-[5-(11β-Fluoro-3,17β-dihydroxy-estra-1,3,5(10)-trien-7α-yl)-pentyl]-N-hexyl-dodecanamide;

N-[5-(11β-Fluoro-3,17β-dihydroxy-estra-1,3,5(10)-trien-7α-yl)-pentyl]-N-octyl-dodecanamide;

N-Cyclohexylmethyl-N-[5-(11β-fluoro-3,17β-dihydroxy-estra-1,3,5(10)-trien-7α-yl)-pentyl]-naphth-2-yl-acetamide;

N-Benzyl-N-[5-(11β-fluoro-3,17β-dihydroxy-estra-13,5(10)-trien-7α-yl)-pentyl]-naphth-2-yl-acetamide;

N-[5-(11β-Fluoro-3,17β-dihydroxy-estra-1,3,5(10)-trien-7α-yl)-pentyl]-N-(2-methoxy-ethyl)-naphth-2-yl-acetamide;

N-[5-(11β-Fluoro-3,17β-dihydroxy-estra-1,3,5(10)-trien-7α-yl)-pentyl]-naphth-2-yl-N-(3-phenyl-propyl)-acetamide;

N-[5-(11β-Fluoro-3,17β-dihydroxy-estra-1,3,5(10)-trien-7α-yl)-pentyl]-N-hexyl-naphth-2-yl-acetamide;

N-[5-(11β-Fluoro-3,17β-dihydroxy-estra-1,3,5(10)-trien-7α-yl)-pentyl]-naphth-2-yl-N-octyl-acetamide;

N-Cyclohexylmethyl-N-[5-(11β-fluoro-3,17β-dihydroxy-estra-1,3,5(10)-trien-7α-yl)-pentyl]-4-phenyl-butyramide;

N-Benzyl-N-[5-(11β-fluoro-3,17β-dihydroxy-estra-1,3,5(10)-trien-7α-yl)-pentyl]-4-phenyl-butyramide;

N-[5-(11β-Fluoro-3,17β-dihydroxy-estra-1,3,5(10)-trien-7α-yl)-pentyl]-N-(2-methoxy-ethyl)-4-phenyl-butyramide;

N-[5-(11β-Fluoro-3,17β-dihydroxy-estra-1,3,5(10)-trien-7α-yl)-pentyl]-4-phenyl-N-(3-phenyl-propyl)-butyramide, N-[5-(11β-Fluoro-3,17β-dihydroxy-estra-1,3,5(10)-trien-7α-yl)-pentyl]-N-hexyl-4-phenyl-butyramide;

N-[5-(11β-Fluoro-3,17β-dihydroxy-estra-1,3,5(10)-trien-7α-yl)-pentyl]-N-octyl-4-phenyl-butyramide;

N-Cyclohexylmethyl-N-[5-(11β-fluoro-3,17β-dihydroxy-estra-1,3,5(10)-trien-7α-yl)-pentyl]-propionamide;

N-Benzyl-N-[5-(11β-fluoro-3,17β-dihydroxy-estra-1,3,5(10)-trien-7α-yl)-pentyl]-propionamide;

N-[5-(11β-Fluoro-3,17β-dihydroxy-estra-1,3,5(10)-trien-7α-yl)-pentyl]-N-(2-methoxy-ethyl)-propionamide;

N-[5-(11β-Fluoro-3,17β-dihydroxy-estra-1,3,5(10)-trien-7α-yl)-pentyl]-N-(3-phenyl-propyl)-propionamide;

N-[5-(11β-Fluoro-3,17β-dihydroxy-estra-1,3,5(10)-trien-7α-yl)-pentyl]-N-hexyl-propionamide;

N-[5-(11β-Fluoro-3,17β-dihydroxy-estra-1,3,5(10)-trien-7α-yl)-pentyl]-N-octyl-propionamide;

4-Biphenyl-N-cyclohexylmethyl-N-[5-(11β-fluoro-3,17β-dihydroxy-estra-1,3,5(10)-trien-7α-yl)-pentyl]-acetamide;

4-Biphenyl-N-benzyl-N-[5-(11β-fluoro-3,17β-dihydroxy-estra-1,3,5(10)-trien-7α-yl)-pentyl]-acetamide;

4-Biphenyl-N-[5-(11β-fluoro-3,17β-dihydroxy-estra-1,3,5(10)-trien-7α-yl)-pentyl]-N-(2-methoxy-ethyl)-acetamide;

4-Biphenyl-N-[5-(11β-fluoro-3,17β-dihydroxy-estra-1,3,5(10)-trien-7α-yl)-pentyl]-N-(3-phenyl-propyl)-acetamide;

4-Biphenyl-N-[5-(11β-fluoro-3,17β-dihydroxy-estra-1,3,5(10)-trien-7α-yl)-pentyl]-N-hexyl-acetamide;

4-Biphenyl-N-[5-(11β-fluoro-3,17β-dihydroxy-estra-1,3,5(10)-trien-7α-yl)-pentyl]-N-octyl-acetamide;

4-Acetylamino-N-cyclohexylmethyl-N-[6-(11β-fluoro-3,17β-dihydroxy-estra-1,3,5(10)-trien-7α-yl)-hexyl]-benzamide;

4-Acetylamino-N-benzyl-N-[6-(11β-fluoro-3,17β-dihydroxy-estra-1,3,5(10)-trien-7α-yl)-hexyl]-benzamide;

4-Acetylamino-N-[6-(11β-fluoro-3,17β-dihydroxy-estra-1,3,5(10)-trien-7α-yl)-hexyl]-N-(2-methoxy-ethyl)-benzamide;

4-Acetylamino-N-[6-(11β-fluoro-3,17β-dihydroxy-estra-1,3,5(10)-trien-7α-yl)-hexyl]-N-(3-phenyl-propyl)-benzamide;

4-Acetylamino-N-[6-(11β-fluoro-3,17β-dihydroxy-estra-1,3,5(10)-trien-7α-yl)-hexyl]-N-hexyl-benzamide;

4-Acetylamino-N-[6-(11β-fluoro-3,17β-dihydroxy-estra-1,3,5(10)-trien-7α-yl)-hexyl]-N-octyl-benzamide;

4-Cyano-N-cyclohexylmethyl-N-[6-(11β-fluoro-3,17β-dihydroxy-estra-1,3,5(10)-trien-7α-yl)-hexyl]-benzamide;

N-Benzyl4-cyano-N-[6-(11β-fluoro-3,17β-dihydroxy-estra-1,3,5(10)-trien-7α-yl)-hexyl]-benzamide;

4-Cyano-N-[6-(11β-fluoro-3,17β-dihydroxy-estra-1,3,5(10)-trien-7α-yl)-hexyl]-N-(2-methoxy-ethyl)-benzamide;

4-Cyano-N-[6-(11β-fluoro-3,17β-dihydroxy-estra-1,3,5(10)-trien-7α-yl)-hexyl]-N-(3-phenyl-propyl)-benzamide;

4-Cyano-N-[6-(11β-fluoro-3,17β-dihydroxy-estra-1,3,5(10)-trien-7α-yl)-hexyl]-N-hexyl-benzamide;

4-Cyano-N-[6-(11β-fluoro-3,17β-dihydroxy-estra-1,3,5(10)-trien-7α-yl)-hexyl]-N-octyl-benzamide;

3-Cyclohexyl-N-cyclohexylmethyl-N-[6-(11β-fluoro-3,17β-dihydroxy-estra-1,3,5(10)-trien-7α-yl)-hexyl]-propionamide;

N-Benzyl-3-cyclohexyl-N-[6-(11β-fluoro-3,17β-dihydroxy-estra-1,3,5(10)-trien-7α-yl)-hexyl]-propionamide;

3-Cyclohexyl-N-[6-(11β-fluoro-3,17β-dihydroxy-estra-1,3,5(10)-trien-7α-yl)-hexyl]-N-(2-methoxy-ethyl)-propionamide;

3-Cyclohexyl-N-[6-(11β-fluoro-3,17β-dihydroxy-estra-1,3,5(10)-trien-7α-yl)-hexyl]-N-(3-phenyl-propyl)-propionamide;

3-Cyclohexyl-N-[6-(11β-fluoro-3,17β-dihydroxy-estra-1,3,5(10)-trien-7α-yl)-hexyl]-N-hexyl-propionamide;

3-Cyclohexyl-N-[6-(11β-fluoro-3,17β-dihydroxy-estra-1,3,5(10)-trien-7α-yl)-hexyl]-N-octyl-propionamide;

N-Cyclohexylmethyl-N-[6-(11β-fluoro-3,17β-dihydroxy-estra-1,3,5(10)-trien-7α-yl)-hexyl]-(3,4-dimethoxyphenyl)-acetamide;

N-Benzyl-N-[6-(11β-fluoro-3,17β-dihydroxy-estra-1,3,5(10)-trien-7α-yl)-hexyl]-(3,4-dimethoxyphenyl)-acetamide;

N-[6-(11β-Fluoro-3,17β-dihydroxy-estra-1,3,5(10)-trien-7α-yl)-hexyl]-N-(2-methoxy-ethyl)-(3,4-dimethoxyphenyl)-acetamide;

N-[6-(11β-Fluoro-3,17β-dihydroxy-estra-1,3,5(10)-trien-7α-yl)-hexyl]-(3,4-dimethox)yphenyl)-N-(3-phenyl-propyl)-acetamide;

N-[6-(11β-Fluoro-3,17β-dihydroxy-estra-1,3,5(10)-trien-7α-yl)-hexyl]-N-hexyl-(3,4-dimethoxyphenyl)-acetamide;

N-[6-(11β-Fluoro-3,17β-dihydroxy-estra-1,3,5(10)-trien-7α-yl)-hexyl]-(3,4-dimethoxyphenyl)-N-octyl-acetamide;

N-Cyclohexylmethyl-4-ethoxy-N-[6-(11β-fluoro-3,17β-dihydroxy-estra-1,3,5(10)-trien-7α-yl)-hexyl]-benzamide;

N-Benzyl-4-ethoxy-N-[6-(11β-fluoro-3,17β-dihydroxy-estra-1,3,5(10)-trien-7α-yl)-hexyl]-benzamide;

4-Ethoxy-N-[6-(11β-fluoro-3,17β-dihydroxy-estra-1,3,5(10)-trien-7α-yl)-hexyl]-N-(2-methoxy-ethyl)-benzamide;

4-Ethoxy-N-[6-(11β-fluoro-3,17β-dihydroxy-estra-1,3,5(10)-trien-7α-yl)-hexyl]-N-(3-phenyl-propyl)-benzamide;

4-Ethoxy-N-[6-(11β-fluoro-3,17β-dihydroxy-estra-1,3,5(10)-trien-7α-yl)-hexyl]-N-hexyl-benzamide;

4-Ethoxy-N-[6-(11β-fluoro-3,17β-dihydroxy-estra-1,3,5(10)-trien-7α-yl)-hexyl]-N-octyl-benzamide;

N-Cyclohexylmethyl-N-[6-(11β-fluoro-3,17β-dihydroxy-estra-1,3,5(10)-trien-7α-yl)-hexyl]-dodecanamide;

N-Benzyl-N-[6-(11β-fluoro-3,17β-dihydroxy-estra-1,3,5(10)-trien-7α-yl)-hexyl]-dodecanamide;

N-[6-(11β-Fluoro-3,17β-dihydroxy-estra-1,3,5(10)-trien-7α-yl)-hexyl]-N-(2-methoxy-ethyl)-dodecanamide;

N-[6-(11β-Fluoro-3,17β-dihydroxy-estra-1,3,5(10)-trien-7α-yl)-hexyl]-N-(3-phenyl-propyl)-dodecanamide;

N-[6-(11β-Fuoro-3,17β-dihydroxy-estra-1,3,5(10)-trien-7α-yl)-hexyl]-N-hexyl-dodecanamide;

N-[6-(11β-Fluoro-3,17β-dihydroxy-estra-1,3,5(10)-trien-7α-yl)-hexyl]-N-octyl-dodecanamide;

N-Cyclohexylmethyl-N-[6-(11β-fluoro-3,17β-dihydroxy-estra-1,3,5(10)-trien-7α-yl)-hexyl]-naphth-2-yl-acetamide;

N-Benzyl-N-[6-(11β-fluoro-3,17β-dihydroxy-estra-1,3,5(10)-trien-7α-yl)-hexyl]-naphth-2-yl-acetamide;

N-[6-(11β-Fluoro-3,17β-dihydroxy-estra-1,3,5(10)-trien-7α-yl)-hexyl]-N-(2-methoxy-ethyl)-naphth-2-yl-acetamide;

N-[6-(11β-Fluoro-3,17β-dihydroxy-estra-1,3,5(10)-trien-7α-yl)-hexyl]-naphth-2-yl-N-(3-phenyl-propyl)-acetamide;

N-[6-(11β-Fluoro-3,17β-dihydroxy-estra-1,3,5(10)-trien-7α-yl)-hexyl]-N-hexyl-naphth-2-yl-acetamide;

N-[6-(11β-Fluoro-3,17β-dihydroxy-estra-1,3,5(10)-trien-7α-yl)-hexyl]-naphth-2-yl-N-octyl-acetamide;

N-Cyclohexylmethyl-N-[6-(11β-fluoro-3,17β-dihydroxy-estra-1,3,5(10)-trien-7α-yl)-hexyl]-4-phenyl-butyramide;

N-Benzyl-N-[6-(11β-fluoro-3,17β-dihydroxy-estra-1,3,5(10)-trien-7α-yl)-hexyl]-4-phenyl-butyramide;

N-[6-(11β-Fluoro-3,17β-dihydroxy-estra-1,3,5(10)-trien-7α-yl)-hexyl]-N-(2-methoxy-ethyl)-4-phenyl-butyramide;

N-[6-(11β-Fluoro-3,17β-dihydroxy-estra-1,3,5 (10)-trien-7α-y)-hexyl]-4-phenyl-N-(3-phenyl-propyl)-butyramide;

N-[6-(11β-Fluoro-3,17β-dihydroxy-estra-1,3,5(10)-trien-7α-yl)-hexyl]-N-hexyl-4-phenyl-butyramide;

N-[6-(11β-Fluoro-3,17β-dihydroxy-estra-1,3,5(0)-trien-7α-yl)-hexyl]-N-octyl-4-phenyl-butyramide;

9-N-Cyclohexylmethyl-N-[6-(11β-fluoro-3,17β-dihydroxy-estra-1,3,5(10)-trien-7α-yl)-hexyl]-propionamide;

N-Benzyl-N-[6-(11β-fluoro-3,17β-dihydroxy-estra-1,3,5(10)-trien-7α-yl)-hexyl]-propionamide;

N-[6-(11β-Fluoro-3,17β-dihydroxy-estra-1,3,5(10)-trien-7α-yl)-hexyl]-N-(2-methoxy-ethyl)-propionamide;

N-[6-(11β-Fluoro-3,17β-dihydroxy-estra-1,3,5(10)-trien-7α-yl)-hexyl]-N-(3-phenyl-propyl)-propionamide;

N-[6-(11β-Fluoro-3,17β-dihydroxy-estra-1,3,5(10)-trien-7α-yl)-hexyl]-N-hexyl-propionamide;

N-[6-(11β-Fluoro-3,17β-dihydroxy-estra-1,3,5(10)-trien-7α-yl)-hexyl]-N-octyl-propionamide;

4-Biphenyl-N-cyclohexylmethyl-N-[6-(11β-fluoro-3, 17β-dihydroxy-estra-1,3,5(10)-trien-7α-yl)-hexyl]-acetamide;

4-Biphenyl-N-benzyl-N-[6-(11β-fluoro-3,17β-dihydroxy-estra-1,3,5(10)-trien-7α-yl)-hexyl]-acetamide;

4-Biphenyl-N-[6-(11β-fluoro-3,17β-dihydroxy-estra-1,3,5(10)-trien-7α-yl)-hexyl]-N-(2-methoxy-ethyl)-acetamide;

4-Biphenyl-N-[6-(11β-fluoro-3,17β-dihydroxy-estra-1,3,5(10)-trien-7α-yl)-hexyl]-N-(3-phenyl-propyl)-acetamide;

4-Biphenyl-N-[6-(11β-fluoro-3,17β-dihydroxy-estra-1,3,5(10)-trien-7α-yl)-hexyl]-N-hexyl-acetamide;

4-Biphenyl-N-[6-(11β-fluoro-3,17β-dihydroxy-estra-1,3,5(10)-trien-7α-yl)-hexyl]-N-octyl-acetamide;

11β-Fluoro-7α-(5-[methyl-(2-p-tolyl-ethyl)-amino]-pentyl}-estra-1,3,5(10)-triene-3,17β-diol;

7α-(5-{[2-(4-Ethoxy-phenyl)-ethyl]-methyl-amino}-pentyl)-11β-fluor-estra-1,3,5(10)-triene-3,17β-diol;

11β-Fluoro-7α-{5-[methyl-(3-phenyl-propyl)-amino]-pentyl}-estra-1,3,5(10)-triene-3,17β-diol;

11β-Fluoro-7α-{5-[methyl-(3-pyridin-3-yl-propyl)-amino]-pentyl}-estra-1,3,5(10)-triene-3,17β-diol;

11β-Fluoro-7α-{5-[methyl-(3-β-tolyl-propyl)-amino]-pentyl}-estra-1,3,5(10)-triene-3,17β-diol;

7α-(5-{[3-(4-Chloro-phenyl)-propyl]-methyl-aminol}-pentyl)-11β-fluor-estra-1,3,5(10)-triene-3,17β-diol;

7α-(5-{[3-(4-Ethoxy-phenyl)-propyl]-methyl-amino}-pentyl)-11β-fluor-estra-1,3,5(10)-triene-3,17β-diol; and 11β-Fluoro-7α-{5-[methyl-(4-methyl-pentyl)-amino]-pentyl}-estra-1,3,5(10)-triene-3,17β-diol.

12. A process for the preparation of a pharmaceutical composition comprising combining a compound according to claim 1 with a pharmaceutically compatible vehicle.

13. A pharmaceutical composition comprising at least one compound according to claim 1 and a pharmaceutically compatible vehicle.

14. A 11β-Halogen-7α-substituted estratriene according to claim 1, in which $R^3$ is H or benzoyl, $R^{11}$ is a fluorine atom, and $R^{17}$ is a hydrogen atom.

15. A 11β-Halogen-7α-substituted estratriene according to claim 14, in which A is a direct bond.

16. A 11β-Halogen-7α-substituted estratriene according to claim 15, in which
$R^7$ is a radical of formula —$(CH_2)_s$—Z—$R^{20}$;
s is an integer from 3 to 8;
Z is —$NR^{21}$;
$R^{21}$ stands for a $C_1$–$C_3$ alkyl group; and
$R^{20}$ means a hydrogen atom, a $C_1$–$C_9$ alkyl group, or one of the groupings:

—$(CH_2)_m$—$C_nF_{2n+1}$, whereby m and n, independently of one another, in each case is an integer from 1 to 8, —$(CH_2)_o$—CH=CF—$C_pF_{2p+1}$, wherein o is 1, 2 or 3 and p is an integer from 2 to 7, —$(CH_2)_m$—O—$(CH_2)_q$-aryl, wherein m has the already indicated meaning, q is 0, 1, 2 or 3 and arvl stands for a phenyl or heteroaryl radical that is optionally substituted in one or two places, or —$(CH_2)_m$—O—$(CH_2)_r$—$C_nF_{2n+1}$, whereby m and n have the already indicated meanings and r stands for an integer from 1 to 5.

17. A 11β-Halogen-7α-substituted estratriene according to claim 15, in which
$R^7$ is a radical of formula —$(CH_2)_s$—Z—$R^{20}$;
s is an integer from 3 to 8;
Z stands for —$NR^{21}$;
$R^{20}$ is a hydrogen atom, a straight-chain or branched-chain alkyl, alkenyl or alkinyl group with up to 10 carbon atoms or one of groupings: —D—$C_nF_{2n+1}$, —L—CH=CF—$C_pF_{2p+1}$, —D—O—$(CH_2)_q$-aryl, —D—O—$(CH_2)_r$—$C_nF_{2n+1}$; and
$R^{21}$ stands for a $C_1$–$C_3$ alkyl group; or
$R^{20}$ and $R^{21}$ with the nitrogen atom, to which they are bonded, form a saturated or unsaturated heterocycle with 5 or 6 chain links, which optionally contains one or two additional heteroatoms, selected from nitrogen, oxygen and sulfur, and optionally is substituted.

18. A 11β-Halogen-7α-substituted estratriene according to claim 15, in which
$R^7$ is a radical of formula —$(CH_2)_s$—Z—$R^{20}$;
s is an integer from 3 to 8;
Z stands for —$SO_x$—;
x stands for 0, 1 or 2; and
$R^{20}$ is —$(CH_2)_m$—O—$(CH_2)_r$—$C_nF_{2n+1}$, wherein m and n have the already indicated meanings and r stands for an integer from 1 to 5.

19. A method of treating a patient suffering from an estrogen dependent-disease comprising administering to said patient an effective amount of a compound according to claim 1.

20. A method of treating a patient suffering from endometriosis or endometrial carcinoma comprising administering to said patient an effective amount of a compound according to claim 1.

21. A method of treating male hair loss, diffuse alopecia, apolecia due to chemotherapy, or alopecia due to hirsutism comprising administering to a patient in need thereof an effective amount of a compound according to claim 1.

22. In a pharmaceutical preparation for male birth control, the improvement wherein said preparation contains a compound according to claim 1.

23. In a pharmaceutical preparation for female birth control, the improvement wherein said preparation contains a compound according to claim 1.

24. A method of treating a patient suffering from osteoporosis comprising administering to said patient an effective amount of a compound according to claim 1.

25. In a method of hormone replacement therapy in a pre-, peri- or post-menopausal patient, the improvement comprising administering to said patient an effective amount of a compound according to claim 1.

26. A compound according to claim 1, wherein A is a direct bond, B is a straight-chain or branched-chain alkylene, Z is $NR^{31}$, and $R^{20}$ is H.

27. A method according to claim 19, wherein said estrogen dependent-disease is breast cancer.

* * * * *

UNITED STATES PATENT AND TRADEMARK OFFICE
CERTIFICATE OF CORRECTION

PATENT NO. : 6,780,855 B2
APPLICATION NO. : 09/380413
DATED : August 24, 2004
INVENTOR(S) : Rolf Bohlmann et al.

It is certified that error appears in the above-identified patent and that said Letters Patent is hereby corrected as shown below:

Column 44, line 38, reads "$R^{17}$" should read -- $R^{17'}$ --
Column 44, line 51, reads "$F_{2+1}$," should read -- $F_{2n+1}$ --

Column 45, line 10, reads "$F_{2+1}$", should read -- $F_{2n+1}$ --
Column 45, line 11, reads "aryl, -D" should read -- aryl, or -D --
Column 45, line 15, after "atoms" insert -- , --

Column 46, line 5, reads "pentyl)-estra" should read -- pentyl}-estra --
Column 46, line 6, reads "3,170-diol" should read -- 3,17β-diol --

Column 47, line 3, insert --
$-(CH_2)_5N(CH_3)(CH_2)_3C_2F_5$
$-(CH_2)_5N(CH_3)(CH_2)_6C_2F_5$
$-(CH_2)_5N(CH_3)(CH_2)_7C_2F_5$
$-(CH_2)_5N(CH_3)(CH_2)_8C_2F_5$
$-(CH_2)_6N(CH_3)(CH_2)_6C_2F_5$
$-(CH_2)_6N(CH_3)(CH_2)_7C_2F_5$
$-(CH_2)_6N(CH_3)(CH_2)_8C_2F_5$
$-(CH_2)_5N(CH_3)(CH_2)_2C_4F_9$
$-(CH_2)_5N(CH_3)(CH_2)_3C_6F_{13}$
$-(CH_2)_5N(CH_3)(CH_2)_3C_8F_{17}$
$-(CH_2)_5N(CH_3)(CH_2)_6C_4F_9$
$-(CH_2)_5N(CH_3)(CH_2)_6C_6F_{13}$
$-(CH_2)_5N(CH_3)(CH_2)_6C_8F_{17}$
$-(CH_2)_5N(CH_3)H$
$-(CH_2)_5N(CH_3)(CH_2)_9H$
$-(CH_2)_5N(CH_3)CH_2CH=CF-C_2F_5$
$-(CH_2)_5N(CH_3)CH_2CH=CF-C_3F_7$
$-(CH_2)_5N(CH_3)CH_2CH=CF-C_5F_{11}$
$-(CH_2)_5N(CH_3)CH_2CH=CF-C_7F_{15}$
$-(CH_2)_5-$ 1-Pyrrolidinyl
$-(CH_2)_5N(CH_3)(CH_2)_3OPhenyl$
$-(CH_2)_5N(CH_3)(CH_2)_3OBenzyl$
$-(CH_2)_5N(CH_3)(CH_2)_3O(CH_2)_3C_2F_5$
$-(CH_2)_9S(CH_2)_3C_2F_5$
$-(CH_2)_9SO(CH_2)_3C_2F_5$
$-(CH_2)_9SO_2(CH_2)_3C_2F_5$
$-(CH_2)_5N(CH_3)(CH_2)_3CH(CH_3)_2$
$-(CH_2)_5N(CH_3)(CH_2)_3$-Pyridyl

UNITED STATES PATENT AND TRADEMARK OFFICE
CERTIFICATE OF CORRECTION

PATENT NO. : 6,780,855 B2
APPLICATION NO. : 09/380413
DATED : August 24, 2004
INVENTOR(S) : Rolf Bohlmann et al.

It is certified that error appears in the above-identified patent and that said Letters Patent is hereby corrected as shown below:

Column 47, line 3 (cont''d)
  $-(CH_2)_5N(CH_3)(CH_2)_3$-Phenyl
  $-(CH_2)_5N(CH_3)(CH_2)_2$-p-Tolyl
  $-(CH_2)_5N(CH_3)(CH_2)_2$-p-Ethoxyphenyl
  $-(CH_2)_5N(CH_3)(CH_2)_3$-p-Tolyl
  $-(CH_2)_5N(CH_3)(CH_2)_3$-p-Chlorphenyl
  $-(CH_2)_5N(CH_3)(CH_2)_3$-O-$CH_2$-Phenyl
  $-(CH_2)_5N(CH_3)(CH_2)_2$-O-p-Br-Phenyl
  $-(CH_2)_5N(CH_3)(CH_2)_2$-O-p-$CF_3$-Phenyl --.

Column 47, line 4 reads "of claim 14," should read --of claim 1, --
Column 47, line 21 reads "(5-[methyl" should read" -- (5-{[methyl --
Column 47, line 31 reads "4,4,5,5,6,6,7,7." should read --4,4,5,5,6,6,7,7, --
Column 47, line 32 reads "fluor" should read --fluoro --
Column 47, line 38 reads "fluor" should read --fluoro --
Column 47, line 40 reads "fluor" should read --fluoro --
Column 47, line 47 reads "3.5(10)" should read --3,5(10) --
Column 47, line 55 reads "fluor" should read --fluoro --
Column 47, line 56 reads "fluor" should read --fluoro --
Column 47, line 56 reads "-amino]" should read --amino} --
Column 48, line 32 reads "7-yl)" should read -- 7α-yl) --
Column 48, line 34 reads "(1-fluoro" should read --11β-fluoro --

Column 48, line 40, reads "1,3,5(1,0)" should read -- 1,3,5(10) --
Column 49, line 34, reads "7α-yll)-butl]" should read -- 7α-yl)-butyl] --

Column 51, line 22, reads "pent)yl]" should read -- pentyl] --
Column 51, line 25, reads "dimethox)yphenyl" should read -- dimethoxyphenyl --
Column 51, line 50, reads "1 35(10)" should read -- 1,3,5(10) --
Column 51, line 66, reads "13,5" should read -- 1,3,5 --
Column 53, line 11, reads "N-Benzyl4" should read -- N-Benzyl-4 --
Column 53, line 52, reads "dimethox)yphenyl" should read -- dimethoxyphenyl --

Column 54, line 18, reads "N-[6-(11β-Fuoro" should read -- N-[6-(11β-Fluoro --
Column 54, line 48, reads "trien-7α-y)" should read -- trien-7α-yl) --
Column 54, line 52, reads "1,3,5(0)" should read -- 1,3,5(10) --

UNITED STATES PATENT AND TRADEMARK OFFICE
CERTIFICATE OF CORRECTION

PATENT NO. : 6,780,855 B2
APPLICATION NO. : 09/380413
DATED : August 24, 2004
INVENTOR(S) : Rolf Bohlmann et al.

It is certified that error appears in the above-identified patent and that said Letters Patent is hereby corrected as shown below:

Column 55, line 17, reads "11β-Fluoro-7α-(5-[methyl-(2-p-tolyl-ethyl)-amino]- ;" should read -- 11β-Fluoro-7α-(5-{methyl-(2-p-tolyl-ethyl)-amino]- --

Column 55, line 20, reads " pentyl)-11β-fluor-estra-1,3,5(10)-triene-3,17β-diol;" should read -- pentyl)-11β-fluoro-estra-1,3,5(10)-triene-3,17β-diol; --

Column 55, line 25, reads "11β-Fluoro-7α-{5-[methyl-(3-β-tolyl-propyl)-amino]-" should read -- 11β-Fluoro-7α-{5-[methyl-(3-p-tolyl-propyl)-amino]- --

Column 55, line 27, reads "7α-(5-{[3-(4-Chloro-phenyl)-propyl]-methyl-amino}-" should read -- 7α-(5-{[3-(4-Chloro-phenyl)-propyl]-methyl-amino)- --

Column 55, line 28 reads "pentyl)-11β-fluor-estra-1,3,5(10)-triene-3,17β-diol;" should read -- pentyl)-11β-fluoro-estra-1,3,5(10)-triene-3,17β-diol; --

Column 55, line 30, reads "-pentyl)-11β-fluor-estra-1,3,5(10)-triene-3,17β-diol; and" should read -- -pentyl)-11β-fluoro-estra-1,3,5(10)-triene-3,17β-diol; and --

Column 55, line 61, reads "and arvl" should read -- and aryl --

Column 56, line 26, reads "-(CH$_{2)m}$" should read -- –(CH$_2$)$_m$ --

Signed and Sealed this

Seventeenth Day of April, 2007

JON W. DUDAS
*Director of the United States Patent and Trademark Office*